(12) United States Patent
Delettre et al.

(10) Patent No.: US 8,461,175 B2
(45) Date of Patent: Jun. 11, 2013

(54) 1-PYRAZOLO[4,3-C]ISOQUINOLINE DERIVATIVES, PREPARATION THEREOF AND THERAPEUTIC USE THEREOF

(75) Inventors: Georges Delettre, Paris (FR); Stéphanie Deprets, Paris (FR); Frank Halley, Paris (FR); Laurent Schio, Paris (FR); Fabienne Thompson, Paris (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 13/265,981

(22) PCT Filed: Apr. 22, 2010

(86) PCT No.: PCT/FR2010/050773
§ 371 (c)(1),
(2), (4) Date: Jan. 13, 2012

(87) PCT Pub. No.: WO2010/122272
PCT Pub. Date: Oct. 28, 2010

(65) Prior Publication Data
US 2012/0115898 A1 May 10, 2012

(30) Foreign Application Priority Data
Apr. 24, 2009 (FR) ...................................... 09 01995

(51) Int. Cl.
C07D 471/04 (2006.01)
A61K 31/4745 (2006.01)
A61P 35/00 (2006.01)

(52) U.S. Cl.
USPC .................. 514/293; 546/82; 546/84; 564/80

(58) Field of Classification Search
None
See application file for complete search history.

(56) References Cited

U.S. PATENT DOCUMENTS
2004/0097541 A1 5/2004 Flohr et al.
2007/0032515 A1 2/2007 Anand et al.

FOREIGN PATENT DOCUMENTS
GB 2 185 255 A 7/1987
WO WO 2007/060198 A1 5/2007

OTHER PUBLICATIONS
International Search Report dated Jul. 23, 2010 issued in PCT/FR2010/050773.
International Preliminary Report on Patentability dated Nov. 1, 2011 issued in PCT/FR2010/050773.

Primary Examiner — Sreeni Padmanabhan
Assistant Examiner — Irina Neagu
(74) Attorney, Agent, or Firm — Scully, Scott, Murphy & Presser, P.C.

(57) ABSTRACT

The invention relates to a compound of formula (I), where: $R_1$ is a phenyl group optionally substituted by one or more halogen atoms; $R_2$ is: a hydrogen atom or a halogen atom or a cyano group; a —C(=O)Y group where Y is a hydrogen atom, or a —NH$_2$ or —OR$_3$ group; a —C(=S)NH$_2$ group; a —C(=NH)NH—OH group; a —CH$_2$OH or —CH$_2$F group; a —CH=N—OH group; a —CH=CH$_2$ or —C≡C—R$_3$ group; a H or H R$_1$ group being a hydrogen or (C$_1$-C$_4$)alkyl group; R$_3$ is a hydrogen atom or (C$_1$-C$_4$)alkyl group; and R$_4$ is a —NH$_2$, (C$_1$-C$_4$)alkyl, (C$_1$-C$_4$)fluoroalkyl or (C$_3$-C$_7$)cycloalkyl group.

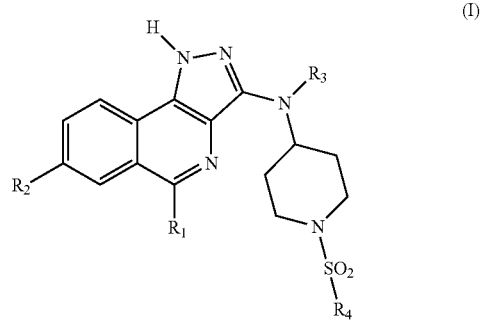

(I)

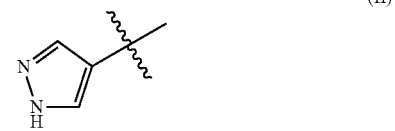

(II)

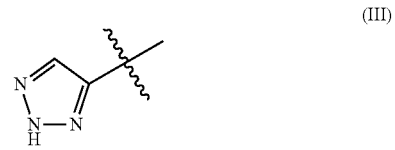

(III)

13 Claims, No Drawings

1-PYRAZOLO[4,3-C]ISOQUINOLINE DERIVATIVES, PREPARATION THEREOF AND THERAPEUTIC USE THEREOF

The present invention relates to 1H-pyrazolo[4,3-c]isoquinoline derivatives and to their application in therapeutics, particularly as anticancer agents. The invention also relates to the process for preparing these compounds of the invention and to some of the reaction intermediates of said process.

DESCRIPTION OF THE INVENTION

Definitions Used

In the context of the present invention the meanings of certain terms are as follows:
  halogen atom (Hal): a fluorine, chlorine, bromine or iodine atom;
  alkyl group: a saturated aliphatic hydrocarbon group comprising from 1 to 6 carbon atoms (advantageously from 1 to 4 carbon atoms) which is linear or branched is obtained by removing a hydrogen atom from an alkane. Examples include the groups methyl, ethyl, propyl, isopropyl, butyl, isobutyl or tert-butyl;
  alkoxy group: an —O-alkyl group, where the alkyl group is as defined above;
  fluoroalkyl group: an alkyl group comprising one or more fluorine atoms in place of one or more hydrogen atoms;
  cycloalkyl group: a cyclic alkyl group comprising between 3 and 7 carbon atoms, all of which form part of the cyclic structure. Examples include the groups cyclopropyl, cyclobutyl, cyclopentyl or cyclohexyl;
  protective group: a group intended to protect a chemical function from unwanted chemical reactions, which is introduced in a protection step and which is released in a subsequent step. Examples of protective groups will be found in T. W. Greene et al. "*Protective Groups in Organic Synthesis*", 3$^{rd}$ edition, 1999. Wiley-Interscience or in J. F. W. McOmie "*Protective Groups in Organic Chemistry*", Plenum Press, 1973. Examples of protective groups include tert-butyl carbamate (BOC) or the [2-(trimethylsilyl)ethoxy]methyl (SEM) group.

In a 1$^{st}$ aspect the present invention provides a compound of formula (I):

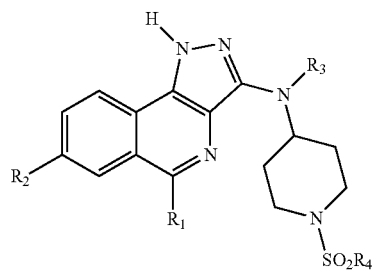

$R_1$ represents a phenyl group which is optionally substituted by one or more halogen atoms. It is more particularly the 2,6-difluorophenyl group.

$R_2$ represents:
  a hydrogen or halogen atom or a cyano group;
  a group —C(=O)Y in which Y represents a hydrogen atom or a group —NH$_2$ or —OR$_a$;
  a group —C(=S)NH$_2$;
  a group —C(=NH)NH—OH;
  a group —CH$_2$OH or —CH$_2$F;
  a group —CH=N—OH;
  a group —CH=CH$_2$ or —C≡C—R$_a$;
  a group

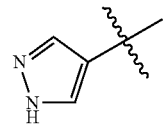

(4-pyrazolyl) or

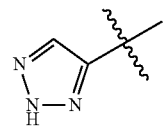

(3-triazolyl);
where $R_a$ represents a hydrogen atom or a (C$_1$-C$_4$)alkyl group. More particularly, $R_a$ represents a hydrogen atom. $R_2$ may be selected more particularly from the groups $R_2$ exemplified in Table I.

$R_3$ represents a hydrogen atom or a (C$_1$-C$_4$)alkyl group. More particularly, $R_3$ represents a hydrogen atom.

$R_4$ represents an —NH$_2$, (C$_1$-C$_4$)alkyl, (C$_1$-C$_4$)fluoroalkyl or (C$_3$-C$_7$)cycloalkyl group. $R_4$ may be selected more particularly from the groups $R_4$ exemplified in Table I.

Distinguished among the compounds of formula (I) is the subgroup of compounds of formula (II):

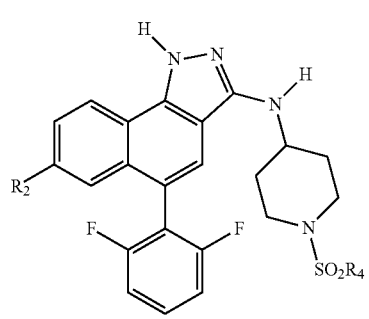

in which $R_2$ and $R_4$ are as defined above.

The compounds of the invention include more particularly the compounds of Table I.

The compounds of the invention may exist in the form of bases or acid addition salts. These salts are advantageously prepared with pharmaceutically acceptable acids, although the salts of other acids, which are usable, for example, for purifying or isolating the compounds, also form part of the invention. The compounds may also, where appropriate, comprise one or more asymmetric carbon atoms. In that case they may exist in the form of enantiomers or diastereoisomers. These enantiomers and diastereoisomers and also mixtures thereof form part of the invention.

In a 2$^{nd}$ aspect the invention provides a process for preparing the compounds of the invention and also some of the reaction intermediates involved in said process.

Preparation of Compounds of Formula (I)

The compounds of formula (I) are prepared in a number of steps starting from $P_1$ and $P_2$ in accordance with Scheme 1:

Scheme 1

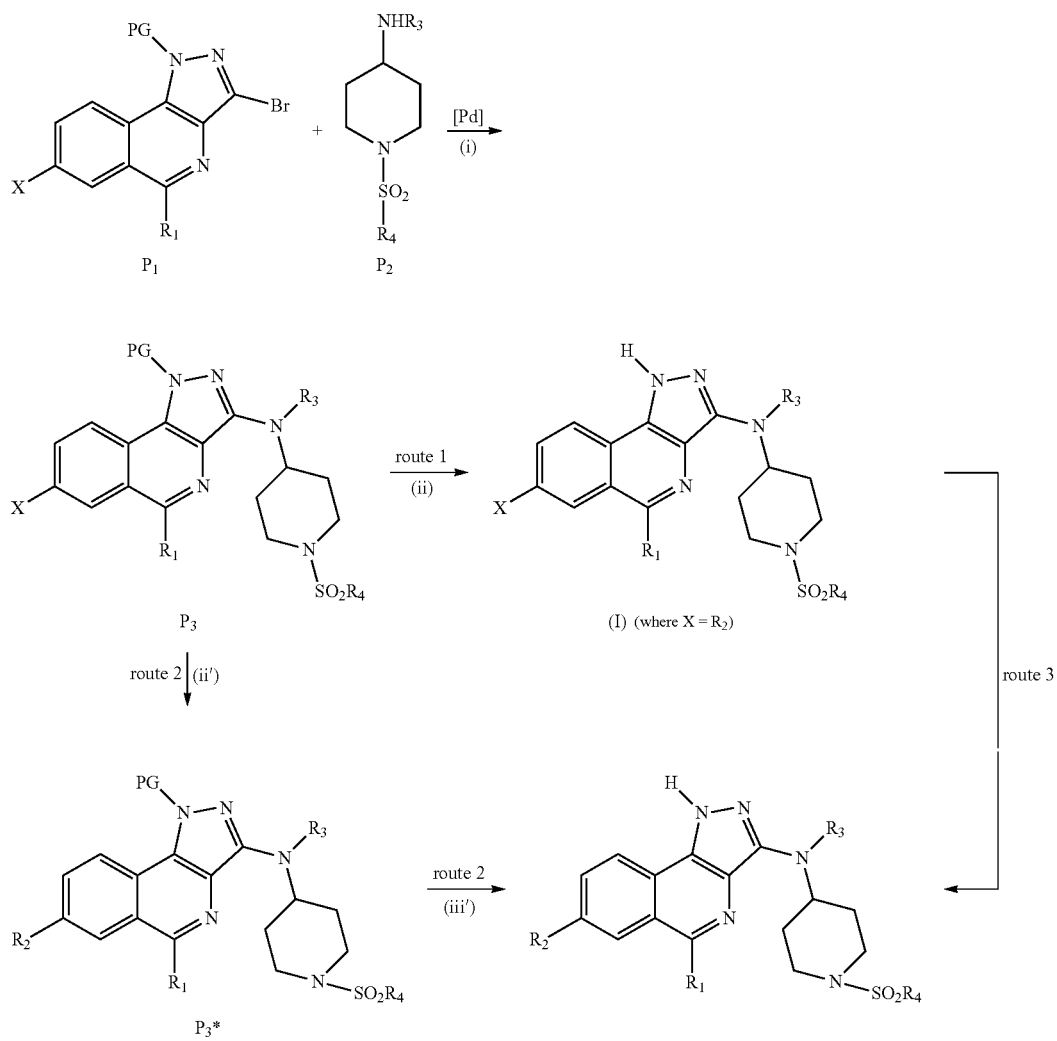

X = —CN, —CHO, —CH=CH$_2$, —H,
—F, —CC—SiMe$_3$, —COOR$_a$, pyrazolyl

Step (i) includes a Büchwald-Hartwig coupling between $P_1$ and $P_2$, leading to $P_3$.

PG denotes a protective group for the NH function of the pyrazole ring and X represents one of the following groups: —CN, —CHO, —CH=CH$_2$, —H, —F, —C≡C—SiMe$_3$, —COOR$_a$ or

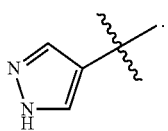

This type of coupling is performed in the presence of a palladium complex (in the (0) or (II) oxidation state, optionally prepared in situ). Use may be made, for example, of Pd(PPh$_3$)$_4$, PdCl$_2$(PPh$_3$)$_2$, Pd(OAc)$_2$ or PdCl$_2$(dppf), Pd$_2$(dba)$_3$ or a mixture of Pd(OAc)$_2$ and 9,9-dimethyl-4,5-bis (diphenylphosphino)xanthene. The complexes most frequently used are palladium(0) complexes. The coupling is favoured in the presence of a base, which may be, for example, K$_2$CO$_3$, NaHCO$_3$, Et$_3$N, K$_3$PO$_4$, Ba(OH)$_2$, NaOH, KF, CsF, Cs$_2$CO$_3$, etc. The coupling may be carried out in a polar solvent such as, for example, 1,4-dioxane. Examples of palladium-based catalytic systems will be found in the following: Guram, A.; Rennels, R.; Buchwald, S. ACIEE 1995, 34, 1348; Louie, J.; Hartwig, J. Tet. Lett. 1995, 3609; Wolfe, J.; Wagaw, S.; Buchwald, S. J. Am. Chem. Soc. 1996, 118, 7215; Driver, M.; Hartwig, J. J. Am. Chem. Soc. 1996, 118, 7217; Hamann, B.; Hartwig, J. J. Am. Chem. Soc. 1998, 120, 7369; Kawatsura, M.; Hartwig, J. J. Am. Chem. Soc. 1999, 121, 1473.

Where the substituent X represents one of the substituents $R_2$ defined above, the compound of formula (I) is obtained after deprotection of the protective group PG in step (ii) of route 1. The deprotection conditions are dependent on the nature of PG and are known to a person skilled in the art (see, for example, T. W. Greene et al. "*Protective Groups in Organic Synthesis*", 3rd edition, 1999). For example, in the case of SEM ([8-(trimethylsilyl)ethoxy]methyl), deprotection is performed in the presence of an acid such as trifluoroacetic acid (TFA) or hydrochloric acid.

Where the substituent X does not represent one of the substituents $R_2$, one or more chemical reactions known to a person skilled in the art are used to convert the substituent X to substituent $R_2$. According to route 2, $P_3$ is converted to $P_3^*$ in step (ii'), then the compound of formula (I) is obtained after deprotection of PG in step (iii'). According to alternative route 3, the conversion takes place directly on a compound of formula (I).

Examples of conversions X ⇨ $R_2$ will be found below:
- X=—CN ⇨ $R_2$=—C(=O)NH$_2$ (step 2—example 4 and example 14) or C(=O)OH: hydrolysis of the nitrile function, by means for example of sodium hydroxide;
- X=—CN ⇨ $R_2$=—C(=S)NH$_2$ (example 9): this reaction may take place by means of ammonium sulphide in methanol with microwaves (see Synlett 2004, 14, 2615-2617);
- X=—CN ⇨ $R_2$=—C(=O)H: this reduction may take place in the presence of diisobutylaluminium hydride (step 1—example 23);
- X=—C(=O)H ⇨ $R_2$=—CH=N—OH: conversion of the aldehyde function to oxime function in the presence of NH$_2$OH (example 20);
- X=—C(=O)H ⇨ $R_2$=—CH$_2$OH (example 3): reduction of the aldehyde function by means of an agent which reduces the aldehyde function—by means, for example, of NaBH$_4$;
- X=—C≡C—SiMe$_3$ ⇨ $R_2$=—C≡CH (step 4—example 7): reaction capable of taking place in the presence of tetrabutylammonium fluoride;
- X=—C(=O)H ⇨ CH$_2$OH ⇨ $R_2$=—CH$_2$F (step 1—example 17): the fluorination is performed by means of diethylaminosulphur trifluoride (DAST) (cf. A. H. Fauq, "N,N-Diethylaminosulfur Trifluoride" in *Encyclopedia of Reagents for Organic Synthesis*, Ed: L. Paquette 2004, J. Wiley & Sons, New York.);

X = —C≡C—SiMe$_3$ ⇨ —C≡CH ⇨

$R_2$ = 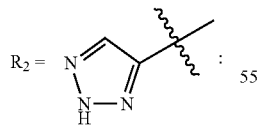 :

Huisgen cycloaddition reaction between the alkyne function and trimethylsilyl azide N$_3$SiMe$_3$, allowing preparation of the 1,2,3-triazole ring.

Preparation of Compounds $P_1$

The compounds $P_1$ for which X represents —H, -Hal, —COOH or —CN are obtained according to Scheme 2 by bromination of $P_4$ in basic medium, followed by protection with the protective group PG. The bromination takes place, for example, by means of the bromine in the presence of KOH in a polar solvent such as DMF. The SEM group, introduced by SEM-Cl in the presence of a base such as, for example, diisopropylethylamine (DIPEA), or the SO$_2$NMe$_2$ group (see example 1) introduced by Cl—SO$_2$NMe$_2$, are examples of protective groups which can be used.

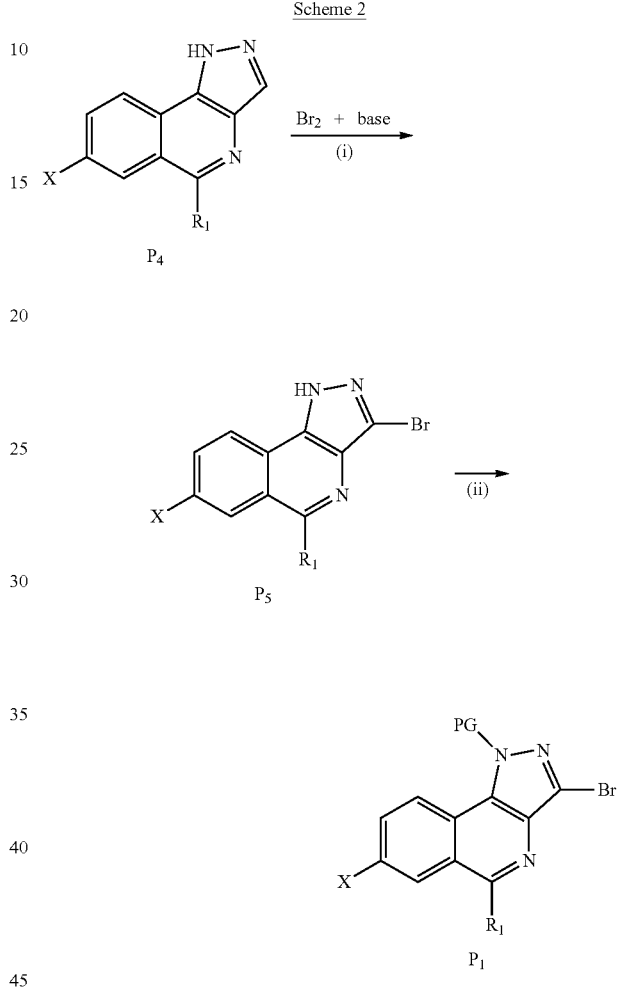

Scheme 2

The compounds $P_1$ for which X represents —CHO, —CH=CH$_2$, —C≡C—SiMe$_3$ or

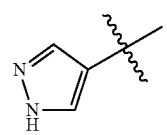

are obtained in one or more steps, starting from the compound $P_5$ or $P_1$ above for which X represents —I and A represents a hydrogen atom ($P_5$) or PG ($P_1$) (Scheme 3):

Scheme 3

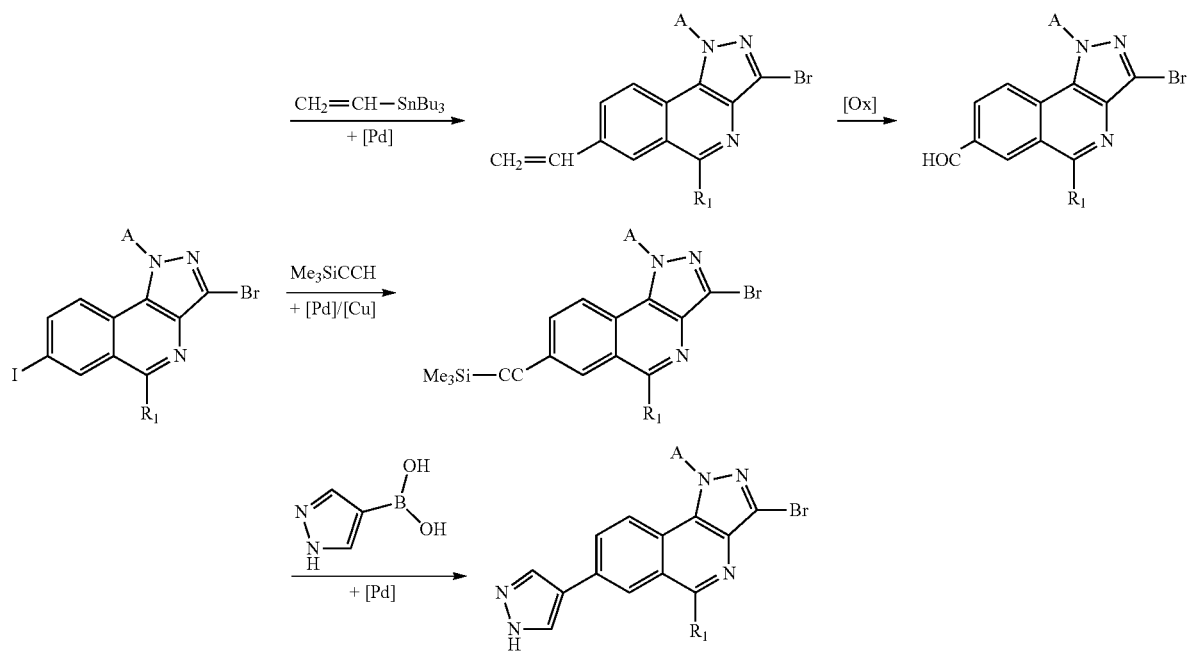

The reactions detailed in Scheme 3 are as follows:
for X=—CH=CH$_2$: Stifle reaction using —CH=CH—SnBu$_3$ and a palladium(0) complex;
for X=—CHO: oxidation reaction using, for example, osmium tetroxide;
for X=—C≡C—SiMe$_3$: Sonogashira reaction in the presence of HC≡C—SiMe$_3$ and a palladium(0) or (II) complex and a copper salt (for further details of this reaction see Chem. Rev. 2007, 107(3), 374-922; cf. also step 2—example 7);
for X = 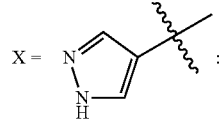 [SMILES: *c1cn[nH]c1] :

Suzuki coupling with 4-pyrazoleboronic acid in the presence of a palladium(0) or (II) complex and a base (it is possible to use the corresponding pinacol ester).

The compounds P$_1$ for which X represents —COO(C$_1$-C$_4$) alkyl are themselves obtained by esterification of the corresponding compounds P$_1$ for which X=—COOH.

Preparation of Compounds P$_4$

The compounds P$_4$ for which X represents —H or -Hal are obtained starting from P$_6$ (Scheme 4) which either is a commercial product (for example X=I, CAS No. 31827-94-8) or is prepared by bromination of the corresponding acetophenone in acidic medium (cf. step 1—example 1):

Scheme 4

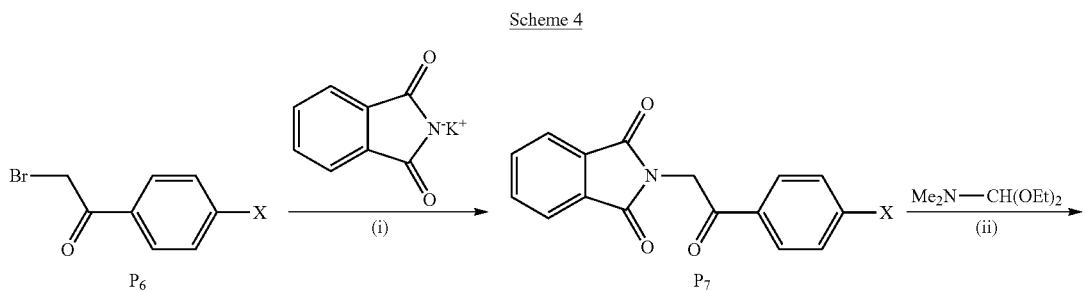

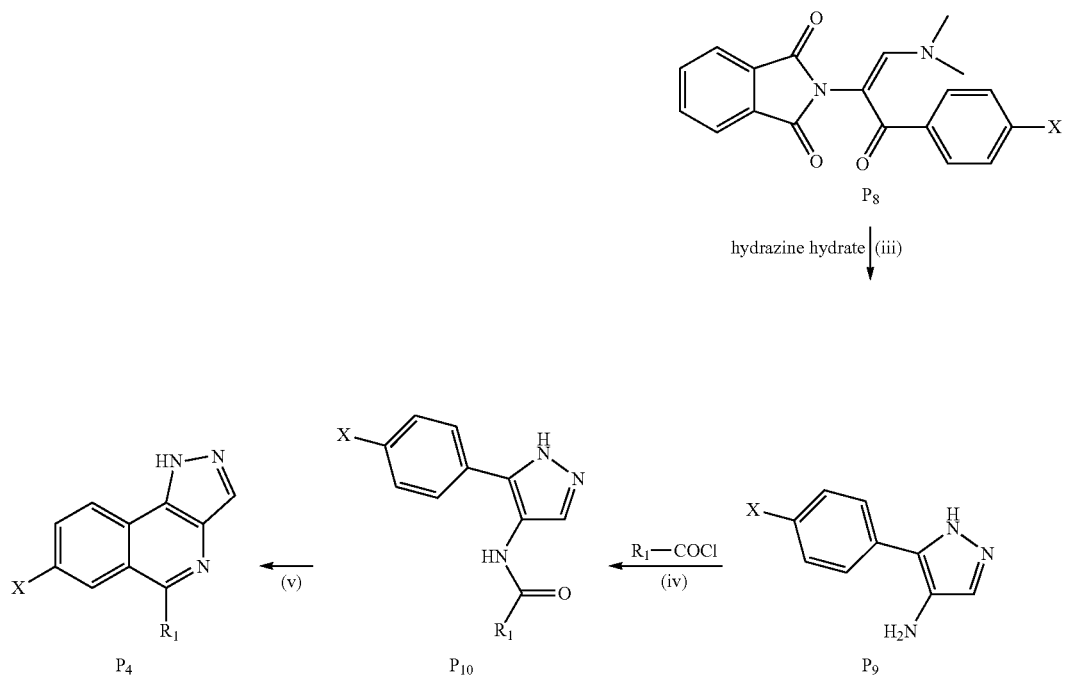

step (i); reaction of $P_6$ with potassium phthalimide, leading to $P_7$. The reaction may be carried out in a polar solvent such as DMF (cf. step 2—example 1 or step 1—example 6);

step (ii): reaction of $P_7$ with N,N-dimethylformamide diethyl acetal, leading to $P_g$. The reaction may be carried out directly in N,N-dimethylformamide diethyl acetal at reflux (cf. step 1—example 3);

step (iii): reaction of $P_g$ with hydrazine hydrate, leading to $P_9$. The reaction may be carried out in a polar solvent such as ethanol (cf. step 4—example 1 or step 3—example 6);

step (iv): acylation reaction of $P_9$ with the acid chloride $R_1COCl$, leading to $P_{10}$. The reaction may be carried out in a chlorinated solvent such as DCM in the presence of a nucleophilic catalyst such as a pyridine;

step (v): Bischler-Napieralski cyclization reaction of $P_{10}$, leading to $P_4$. The reaction may be carried out in the presence of $P_2O_5$ and phenylphosphine acid dichloride at temperature >100° C. (cf. step 6—example 1 or step 5—example 6). It is also possible to use $POCl_3$.

The compounds $P_4$ for which X represents —CN are obtained by cyanation of the corresponding protected compounds $P_4$ for which X represents —I. Use is made, for example, of $Zn(CN)_2$ and a palladium(0) complex (Rosenmund-Braun reaction: see Chem. Rev. 1951, 49, 392).

Preparation of $P_2$ $P_2$ may be prepared according to Scheme 5 (cf. also WO 2003082871 steps 1-4—example 4, pp. 34-36), starting from the aminopiperidine protected on the amine function:

Scheme 5

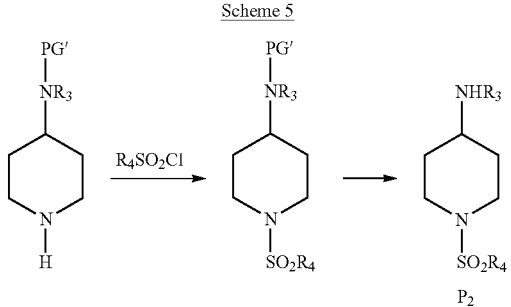

PG' represents a protective group for the amine function. This is, advantageously, BOC (tert-butoxycarbonyl).

The invention hence also provides a process for preparing a compound of formula:

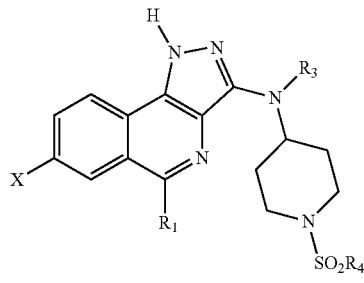

in which $R_1$, $R_3$ and $R_4$ are as defined above and X represents a hydrogen or fluorine atom, a group cyano, —C(=O)H, —CH=CH$_2$, —C≡C—SiMe$_3$, —COOR$_a$, where R$_a$ represents a hydrogen atom or a (C$_1$-C$_4$)alkyl group, or the group

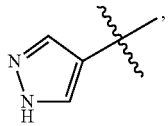

comprising:
(i) coupling the compounds P$_1$ and P$_2$ defined in Scheme 1 in the presence of a palladium complex and, optionally, of a base,
(ii) deprotecting the product obtained in the preceding step (i).

The invention additionally provides a process for preparing a compound of formula:

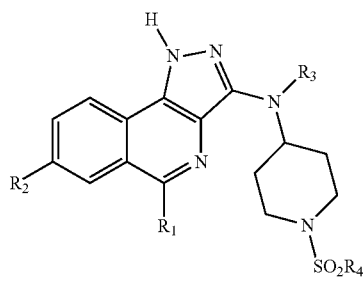

(I)

in which $R_1$, $R_3$ and $R_4$ are as defined above and $R_2$ represents one of the following groups: —C(=O)NH$_2$, —C(=S)NH$_2$, —C(=O)H, —CH=N—OH, —CH$_2$OH, —CH$_2$F, —C≡CH or

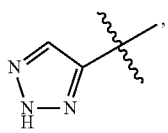

starting from the compound of formula:

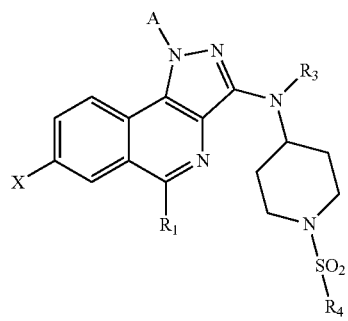

in which X represents a —CN, —CHO, —CH$_2$OH, —C≡CH or —C≡C—SiMe$_3$ group and A represents a hydrogen atom or a protective group PG, comprising:
(i)
hydrolysing the group X=—CN to group $R_2$=—C(=O)NH$_2$ or —C(=O)OH;
converting the group X=—CN to group $R_2$=—C(=S)NH$_2$ in the presence of ammonium sulphide with microwaves;
reducing the group X=—CN to group $R_2$=—C(=O)H;
converting the group X=—C(=O)H to group $R_2$=—CH=N—OH in the presence of NH$_2$OH;
reducing the group X=—C(=O)H to group $R_2$=—CH$_2$OH;
converting the group X=—C≡C—SiMe$_3$ to group $R_2$=—C≡CH;
fluorinating the group X=—CH$_2$OH to group $R_2$=—CH$_2$F;
converting the group X=—C≡CH to group

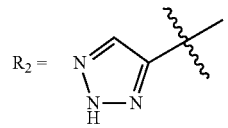 [SMILES: *c1cn[nH]n1]

by cycloaddition in the presence of trimethylsilyl azide N$_3$SiMe$_3$;
(ii) where appropriate, deprotecting the product obtained in the preceding step (i).

The compounds of formula (I) may also be prepared starting from P$_1$ and P'$_2$ according to Scheme 6:

Scheme 6

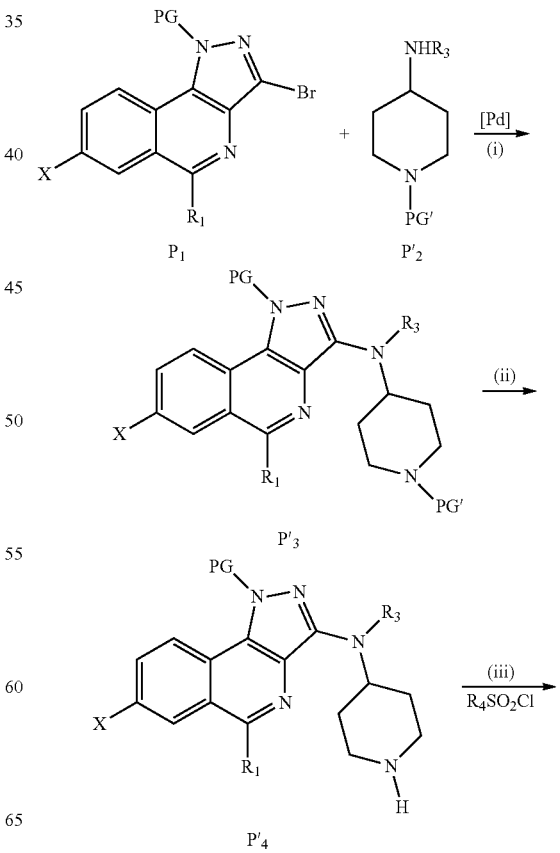

-continued

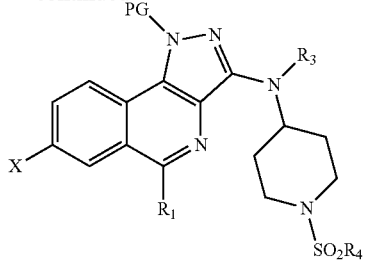

P'₅

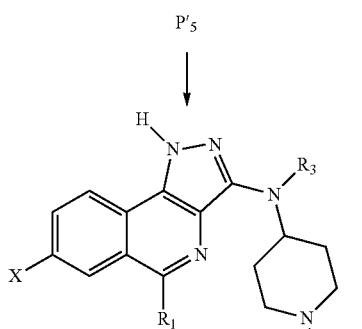

X = —CN, —CHO, —CH=CH₂, —H, —F, —CC—SiMe₃, —COORa, pyrazolyl

Step (i) involves a Büchwald-Hartwig coupling between $P_1$ and $P'_2$, leading to $P'_3$. PG denotes a protective group for the NH function of the pyrazole ring. PG' represents a protective group for the amine function, and X represents one of the following groups: —CN, —CHO, —CH=CH₂, —H, —F, —C≡C—SiMe₃, —COOR$_a$ or

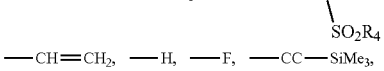

In step (ii), the amine function is deprotected to give $P'_4$, which then reacts in step (iii) with $R_4SO_2Cl$ to give $P'_5$. The NH function of the pyrazole ring is then deprotected to give the compound of formula (I).

The invention hence also provides a process for preparing a compound of formula:

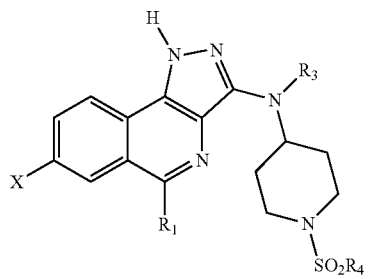

in which $R_1$, $R_3$ and $R_4$ are as defined above and X represents a hydrogen or fluorine atom, a group cyano, —C(=O)H, —CH=CH₂, —C≡C—SiMe₃, —COOR$_a$, where R$_a$ represents a hydrogen atom or a (C₁-C₄)alkyl group, or the group

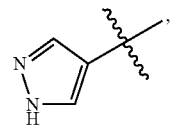 [SMILES: *c1cn[nH]c1]

comprising:
(i') reacting the compound $P'_4$ of formula:

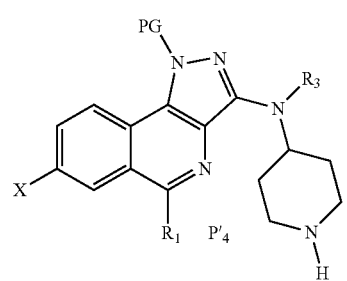

with $R_4SO_2Cl$,
(ii') deprotecting the product obtained in the preceding step (i).

The invention also provides the compounds of formula (Scheme 1)

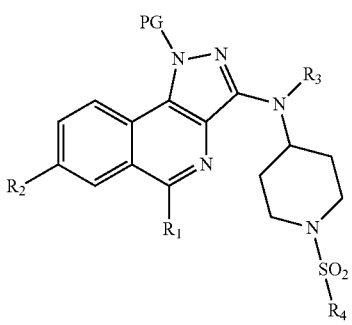

or of formula (Scheme 6)

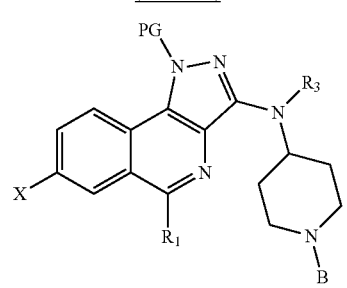

in which:
$R_1$, $R_2$, $R_3$ and $R_4$ are as defined above;
X represents a hydrogen or fluorine atom, a group cyano, —C(=O)H, —CH=CH₂, —C≡CH, —COOR$_a$, where R$_a$ represents a hydrogen atom or (C₁-C₄)alkyl group, or the group

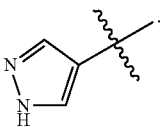 [SMILES: *c1cn[nH]c1]

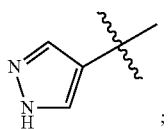

PG represents a protective group for the NH function of the pyrazole group;

B represents a hydrogen atom or a protective group PG' for the amine function.

PG represents more particularly SEM or $SO_2NMe_2$; and PG', BOC.

In a 3$^{rd}$ aspect, the invention provides a pharmaceutical composition comprising a compound as defined above in combination with a pharmaceutically acceptable excipient. The excipient is selected, according to the pharmaceutical form and desired mode of administration, from the customary excipients, which are known to a person skilled in the art.

In a 4$^{th}$ aspect, the invention provides a medicament which comprises a compound as defined above, and also the use of a compound as defined above for preparing a medicament. The compound may be administered in combination with one or more other anticancer agents. This treatment may be administered simultaneously, separately or else sequentially. The treatment will be adapted by the practitioner in accordance with the disease and the tumour to be treated.

In a 5$^{th}$ aspect, the invention also provides a method of treating the pathologies indicated above, which comprises administering to a patient an effective dose of a compound according to the invention or one of its pharmaceutically acceptable salts or hydrates or solvates.

EXAMPLES

The examples which follow illustrate the preparation of some compounds in accordance with the invention.

LC-MS-DAD-ELSD Analysis

Column: Atlantis T3; 3.0×50 mm; particle size 3 μm; Waters 186003721eluent flow rate=0.8 ml/min; oven temperature: LC=35° C.; DAD wavelength 200-400 nm gradient in 7 min using a mixture A (water/formic acid 0.1%) and acetonitrile B: 0 min (95% A; 5% B); 5 min (5% A; 95% B); 5.5 min (5% A; 95% B); 6.5 min (95% A; 5% B); 7 min (95% A; 5% B).

$^1$H NMR Analysis

The $^1$H NMR spectra were obtained on a Bruker 400 MHz instrument in DMSO-d6. The chemical shifts are given in ppm.

Preparation of the Compounds of Table I

Example 1

5-(2,6-difluorophenyl)-3-{[1-(methylsulphonyl)piperidin-4-yl]amino}-1H-pyrazolo[4,3-c]isoquinoline-7-carboxamide Step 1: A 1 l three-necked flask is charged with 50 g of 4-iodoacetophenone in 500 ml of glacial acetic acid. Added dropwise then at room temperature (RT) are 10.4 ml of bromine. The reaction mixture is stirred at RT for 2 h and then evaporated under reduced pressure (RP). The crude product is taken up three times with around 200 ml of toluene, then once with 200 ml of methylene chloride (DCM), and concentrated each time under reduced pressure (RP) in order to remove all traces of acetic acid and bromine. The orange solid obtained is dried under vacuum in a desiccator at RT. This gives 66 g of 2-bromo-1-(4-iodophenyl)ethanone in the form of an orange solid, which is used as it is in the following step. Mass spectrum (MS) (E/I): m/z=404 (M+); $^1$H NMR: 4.90 (s, 2 H); 7.74

Step 2: A 500 ml round-bottomed flask is charged with 66 g of 2-bromo-1-(4-iodophenyl)ethanone in 140 ml of DMF and 38 g of potassium phthalimide. The mixture is stirred at RT for 4 h and the precipitate formed is filtered off on a glass frit and washed with 3 times 50 ml of isopropyl ether. Drying under RP gives 80 g of 2-[2-(4-iodophenyl)-2-oxoethyl]isoindole-1,3-dione in the form of a white solid, which is used as it is in the following step. MS (E/I): m/z=391 (M+); $^1$H NMR: 5.21 (s, 2H); 7.84 (d, J=8.5 Hz, 2H); from 7.88 to 7.98 (m, 4H); 8.00 (d, J=8.5 Hz, 2H). m.p. (Kofler): 230° C.

Step 3: A 500 ml round-bottomed flask is charged with 81.6 g of 2-[2-(4-iodophenyl)-2-oxoethyl]isoindole-1,3-dione in 134 ml of N,N-dimethylformamide diethyl acetal. The reaction mixture is heated at reflux for 5 h and then cooled with an ice bath to 0° C. The precipitate formed is filtered off with suction on a glass frit and then washed with twice 50 ml of isopropyl ether, followed by two clarifying washes (washing of the cake without stirring) with 50 ml of isopropyl ether. Drying under RP gives 79 g of a mixture of the E and Z isomers of 2-[2-dimethylamino-1-(4-iodobenzoyl)-vinyl]isoindole-1,3-dione in the form of an orange-yellow solid. MS (E/I): m/z=446 (M+); $^1$H NMR: 2.92 (broad m, 6H); 7.22 (d, J=8.5 Hz, 2H); 7.49 (broad s, 1H); 7.80 (d, J=8.5 Hz, 2H); 7.92 (m, 4H); m.p. (Kofler): 226° C.

Step 4: A 1 l round-bottomed flask is charged at RT with 78.3 g of a mixture of the E and Z isomers of 2-[2-dimethylamino-1-(4-iodobenzoyl)vinyl]isoindole-1,3-dione in 535 ml of ethanol. A brown suspension is obtained which is admixed with 21 ml of hydrazine hydrate. The suspension is heated at reflux. After 30 min of heating, the mixture is observed to thicken and take on a lemon yellow colour. This suspension is stirred at reflux for 4 h 30 min and then the mixture is taken to RT. The suspension is filtered with suction on a frit and the precipitate is washed with twice 100 ml of ethanol. This gives a filtrate which after evaporation gives 46 g of a yellow solid 1, leaving the original precipitate 2, which is dried at 40° C. under RP to give 39 g of a cream-coloured powder. 1 is stirred for 15 min in 300 ml of AcOEt. The mixture is filtered, and this operation is repeated 13 times, using 150 ml of AcOEt each time. The various filtrates are combined and concentrated under RP. This gives 24.3 g of a golden yellow-coloured solid. 2 is taken up in 300 ml of AcOEt. The mixture is filtered and the operation is repeated 7 times, using 150 ml of AcOEt each time. The various filtrates are combined and concentrated under RP. This gives 7.3 g of a lemon yellow-coloured solid. The two batches are combined to give 31.6 g of 3-(4-iodophenyl)-1H-pyrazol-4-ylamine (orange solid). MS (E/I): m/z=285 (M+); $^1$H NMR: 4.04 (broad s, 2H); 7.15 (s, 1H); 7.57 (broad d, J=8.5 Hz, 2H); 7.72 (d, J=8.5 Hz, 2H); 12.35 (broad m, 1H).

Step 5: A 2 l round-bottomed flask is charged with 31.5 g of 3-(4-iodophenyl)-1H-pyrazol-4-ylamine in 425 ml of DCM and 278 ml of pyridine. The mixture is cooled to 0° C. with an ice bath and 13.9 ml of the chloride of 2,6-difluorobenzoic acid are added. The temperature is allowed to return gradually to RT over 3 h. Following evaporation of the solvent under RP, water is added to the crude reaction product, and the aqueous phase is then extracted with AcOEt. The organic extracts are combined, washed with saturated NaCl solution and dried over $MgSO_4$. The AcOEt is then evaporated under vacuum to give 49.2 g of a mixture of 2,6-difluoro-N-[5-(4-iodophenyl)-1H-pyrazol-4-yl]benzamide and N-[1-(2,6-difluoro-benzoyl)-5-(4-iodophenyl)-1H-pyrazol-4-yl]-2,6-difluorobenzamide in the form of an orange foam, which is used as it is.

The crude reaction product is treated to give solely the expected product: in a 3 l round-bottomed flask, 49.2 g of the mixture of 2,6-difluoro-N-[5-(4-iodophenyl)-1H-pyrazol-4-yl]benzamide and N-[1-(2,6-difluoro-benzoyl)-5-(4-iodophenyl)-1H-pyrazol-4-yl]-2,6-difluorobenzamide are dissolved, at RT and under argon, in 950 ml of ethanol and 470 ml of THF, and then 385 ml of 5N aqueous sodium hydroxide solution are added. After 1 h of stirring at RT, the mixture is poured into 1025 ml of 2N hydrochloric acid. It is extracted with AcOEt and the organic phases are washed with saturated NaCl solution, dried over MgSO$_4$ and then concentrated under RP. This gives a crude product, which is suspended in 570 ml of DCM and stirred at reflux of the DCM for 15 min. After cooling with an ice bath, the precipitate is filtered off with suction and washed with twice 30 ml of ice-cold DCM. This gives 258 g of 2,6-difluoro-N-[5-(4-iodophenyl)-1H-pyrazol-4-yl]benzamide (cream solid). MS (E/I): m/z=425 (M+); $^1$H NMR: from 7.15 to 7.25 (m, 2H); 7.51 (d, J=8.5 Hz, 2H); 7.57 (m, 1H); 7.79 (d, J=8.5 Hz, 2H); 7.93 (broad m, 1H); 10.2 (s, 1H); 13.3 (broad m, 1H); m.p. (Kofler bench): 204° C.

Step 6: A 500 ml round-bottomed flask equipped with a magnetic stirrer and with a septum having a top-mounted argon intake is charged with 9.2 g of 2,6-difluoro-N-[5-(4-iodophenyl)-1H-pyrazol-4-yl]benzamide, 168 ml of phenylphosphine acid dichloride and 46.3 g of phosphorus pentoxide. After 23 h at 165° C., the mixture is cooled to RT and then poured into a mixture of 260 ml of water and 400 g of ice. The temperature rises to 40° C. Neutralization is carried out by slow addition of 930 ml of 3M sodium carbonate solution and then 110 ml of 28% aqueous ammonia. Extraction is carried out with once 1150 ml and 2 times 550 ml of AcOEt. The organic extracts are combined, washed with saturated NaCl solution and dried over MgSO$_4$, and then concentrated under RP. The solid obtained is stirred in 220 ml of DCM at reflux for 15 min, cooled using an ice bath, and then filtered and washed with 2 times 28 ml of ice-cold DCM. Drying under vacuum at 40° C. gives 7.4 g of 5-(2,6-difluorophenyl)-7-iodo-1H-pyrazolo[4,3-c]isoquinoline (cream solid). MS (E/I): m/z=407 (M+); $^1$H NMR: 7.39 (t, J=8.0H, 2H); 7.71 (m, 1H); 7.99 (broad s, 1H); 8.33 (m, 2H); 8.45 (broad s, 1H); 14.35 (broad s, 1H); m.p. (Kofler bench)=260° C.

Step 7: A 1000 ml round-bottomed flask is charged under argon with 7.4 g of 5-(2,6-difluorophenyl)-7-iodo-1H-pyrazolo[4,3-c]isoquinoline in 190 ml of tetrahydrofuran and 20 ml of dimethylformamide (DMF); after cooling to 0° C. using an ice bath, 1 g of NaH (50% in suspension in liquid petrolatum) is added and the mixture is stirred at 0° C. for 30 min and then admixed at the same temperature with 2.7 ml of dimethylsulphamoyl chloride. After 1 h at RT, the crude product is poured into saturated NH$_4$Cl solution. The aqueous phase is extracted with 3 times 300 ml of AcOEt. The organic extracts are combined, dried over MgSO$_4$ and then concentrated under RP. Purification by flash chromatography on silica gel (40-63 μm), eluting with a DCM/methanol mixture (98/02 by vol.), gives 9 g of a mixture of the positional regioisomers 5-(2,6-difluorophenyl)-7-iodopyrazolo[4,3-c]isoquinoline-1-sulphonic acid dimethylamide and 5-(2,6-difluorophenyl)-7-iodopyrazolo[4,3-c]isoquinoline-2-sulphonic acid dimethylamide in the form of a solid. MS (E/I): m/z=514 (M+); $^1$H NMR: 3.02 (s, 6H); 7.40 (t, J=8.0 Hz, 2H); 7.74 (m, 1H); 7.92 (broad s, 1H); 8.32 (dd, J=1.5 and 8.5 Hz, 1H); 8.39 (d, J=8.5 Hz, 1H); 9.31 (s, 1H); m.p.=224° C.

Step 8: A 500 ml round-bottomed flask equipped with a magnetic stirrer and with a condenser having a top-mounted argon intake is charged with 5.4 g of the solid obtained in step 7 in 100 ml of DMF. After argon has been bubbled through the reaction mixture for 10 min, 1.6 g of zinc cyanide and 0.28 g of Pd(PPh$_3$)$_4$ are added and the mixture is heated with stirring at 130° C. for 1 h 30 min. The crude reaction product is poured into 100 volumes of water, the aqueous phase is extracted with 3 times 400 ml of AcOEt and then the organic extracts are combined, dried over MgSO$_4$ and concentrated under RP. The residue obtained is pasted in diisopropyl oxide, filtered and dried in a desiccator at 35° C. This gives 3.3 g of a mixture of the regioisomers of 7-cyano-5-(2,6-difluorophenyl)pyrazolo[4,3-c]isoquinoline-1-sulphonic acid dimethylamide (cream solid). MS (E/I): m/z=413 (M+); $^1$H NMR: 3.03 (s, 6H); 7.39 (t, J=8.0 Hz, 2H); 7.75 (m, 1H); 8.24 (broad s, 1H); 8.38 (dd, J=1.5 and 8.5 Hz, 1H); 8.76 (d, J=8.5 Hz, 1H); 9.41 (s, 1H); m.p.: 231° C. (Kofler bench).

Step 9: A 250 ml round-bottomed flask is charged with 4 g of a mixture of the regioisomers of 7-cyano-5-(2,6-difluorophenyl)pyrazolo[4,3-c]isoquinoline-1-sulphonic acid dimethylamide in 160 ml of DCM. After cooling to 0° C. using an ice bath, 108 ml of TFA are added and the mixture is stirred at RT for 6 h. The mixture is concentrated under RP and the solid obtained is taken up in 600 ml of water, and 50 ml of 0.75 M ammonia solution are added. The aqueous phase is extracted with 3 times 150 ml of AcOEt. The organic extracts are combined, washed with saturated NaCl solution and then dried over MgSO$_4$. Concentration of the AcOEt under RP gives 2.6 g of 5-(2,6-difluorophenyl)-1H-pyrazolo[4,3-c]isoquinoline-7-carbonitrile (beige solid). MS (E/I): m/z=306 (M+); $^1$H NMR: 7.38 (t, J=8.0 Hz, 2H); 7.72 (m, 1H); 8.24 (broad s, 1H); 8.34 (dd, J=1.5 and 8.5 Hz, 1H); 8.59 (s, 1H); 8.70 (d, J=8.5 Hz, 1H); 14.5 (very broad m, 1H).

Step 10: A 250 ml round-bottomed flask equipped with a magnetic stirrer and with a septum having a top-mounted argon intake is charged with 2.6 g of 5-(2,6-difluorophenyl)-1H-pyrazolo[4,3-c]isoquinoline-7-carbonitrile in 85 ml of DMF, 0.87 ml of bromine and 1.5 g of KOH. After 1 h of stirring at RT, the mixture is poured into ice-water. The aqueous phase is extracted with 3 times 150 ml of AcOEt. The organic extracts are combined, washed with saturated NaCl solution, dried over MgSO$_4$ and evaporated under RP. This gives 3.3 g of 3-bromo-5-(2,6-difluorophenyl)-1H-pyrazolo[4,3-c]isoquinoline-7-carbonitrile, which is used as it is for the following step (light yellow solid). MS (E/I): m/z=385 (M+); $^1$H NMR: 7.39 (t, J=8.0 Hz, 2H); 7.75 (m, 1H); 8.34 (broad s, 1H); 8.41 (dd, J=1.5 and 8.5 Hz, 1H); 8.68 (d, J=8.5 Hz, 1H); 14.85 (broad m, 1H).

Step 11: A 250 ml round-bottomed flask equipped with a magnetic stirrer and with a septum having a top-mounted argon intake is charged with 3.3 g of 3-bromo-5-(2,6-difluorophenyl)-1H-pyrazolo[4,3-c]isoquinoline-7-carbonitrile in 85 ml of DMF, 10.6 ml of N,N-diisopropylethylamine and 3.2 ml of 2-(trimethylsilyl)ethoxymethyl chloride. After 5 h at RT, the mixture is poured into 8 volumes of ice-water. The aqueous phase is extracted with 3 times 200 ml of AcOEt, and the organic extracts are combined, washed with saturated NaCl solution, dried over MgSO$_4$ and concentrated under RP. Purification is carried out by flash chromatography on silica gel (40-63 μm), eluting with a mixture of DCM and methanol (99.5/0.5 by vol.), to give on one hand 2.1 g of 3-bromo-5-(2,6-difluorophenyl)-1-{[2-(trimethylsilyl)ethoxy]methyl}-1H-pyrazolo[4,3-c]isoquinoline-7-carbonitrile in the form of a white solid. MS (E/I): m/z=515 (M+); $^1$H NMR: −0.12 (s, 9H); 0.87 (t, J=8.0 Hz, 2H); 3.65 (t, J=8.0 Hz, 2H); 6.17 (s, 2H); 7.40 (t, J=8.0 Hz, 2H); 7.77 (m, 1H); 8.41 (broad s, 1H); 8.47 (dd, J=1.5 and 8.5 Hz, 1H); 8.77 (d, J=8.5 Hz, 1H). And, on the other hand, 1.2 g of 3-bromo-5-(2,6-difluorophenyl)-2-{[2-(trimethylsilyl)ethoxy]methyl}-2H-pyrazolo[4,3-c]isoquinoline-7-carbonitrile (white solid). MS (E/I): m/z=515

(M+); $^1$H NMR: −0.05 (s, 9H); 0.90 (t, J=8.0 Hz, 2H); 3.73 (t, J=8.0 Hz, 2H); 5.92 (s, 2H); 7.38 (t, J=8.0 Hz, 2H); 7.76 (m, 1H); 8.24 (broad s, 1H); 8.34 (dd, J=1.5 and 8.5 Hz, 1H); 8.69 (d, J=8.5 Hz, 1H).

Step 12: A 150 ml round-bottomed flask equipped with a magnetic stirrer and with a septum having a top-mounted argon intake is charged with 1 g of 3-bromo-5-(2,6-difluorophenyl)-1-{[2-(trimethylsilyl)ethoxy]methyl}-1H-pyrazolo[4,3-c]isoquinoline-7-carbonitrile in 27 ml of 1-4-dioxane. After argon has been bubbled through the reaction mixture for 10 min, 692 mg of 1-methanesulphonyl-piperidin-4-ylamine, 4 g of caesium carbonate, 135 mg of 9,9-dimethyl-4,5-bis(diphenylphosphino)xanthene and 43 mg of palladium(II) acetate are added. The reaction mixture is heated at reflux for 4 h. After cooling, the mixture is poured into water, extracted with AcOEt, washed with saturated NaCl solution, dried over MgSO$_4$, filtered and concentrated under RP. Purification is carried out by flash chromatography on silica gel (40-63 µm), eluting with a mixture of DCM and AcOEt (85/15 by vol.), to give 1 g of 5-(2,6-difluorophenyl)-3-{[1-(methylsulphonyl)piperidin-4-yl]amino}-1-{[2-(trimethylsilyl)ethoxy]methyl}-1H-pyrazolo[4,3-c]isoquinoline-7-carbonitrile (yellow solid), MS (E/I): m/z=596 (M+); $^1$H NMR: −0.05 (s, 9H); 0.89 (t, J=8.0 Hz, 2H); 1.61 (m, 2H); 2.11 (m, 2H); 2.74 (m, 2H); 2.85 (s, 3H); 3.59 (m, 2H); 3.68 (t, J=8.0 Hz, 2H); 4.46 (m, 1H); 5.69 (s, 2H); 6.70 (d, J=8.0 Hz, 1H); 7.34 (t, J=8.0 Hz, 2H); 7.68 (m, 1H); 7.97 (broad s, 1H); 8.14 (dd, J=1.5 and 8.5 Hz, 1H); 8.48 (d, J=8.5 Hz, 1H).

Step 13; A 250 ml round-bottomed flask equipped with a magnetic stirrer and with a septum having a top-mounted argon intake is charged with 1 g of 5-(2,6-difluorophenyl)-3-{[1-(methylsulphonyl)piperidin-4-yl]amino}-1-{[2-(trimethylsilyl)ethoxy]methyl}-1H-pyrazolo[4,3-c]isoquinoline-7-carbonitrile in 96 ml of DCM. After cooling to 0° C. using an ice bath, 10.7 ml of TFA are added and the mixture is stirred at RT for 20 h. The reaction mixture is concentrated under RP and the solid obtained is taken up in 100 ml of water and extracted with three times 100 ml of AcOEt, dried over MgSO$_4$, filtered and concentrated under RP. This gives 992 mg of 5-(2,6-difluorophenyl)-3-{[1-(methylsulphonyl)piperidin-4-yl]amino}-1H-pyrazolo[4,3-c]isoquinoline-7-carbonitrile trifluoroacetate, which is used as it is in the following step. MS (E/I): m/z=482 (M+).

Step 14: A 250 ml round-bottomed flask equipped with a magnetic stirrer and with a septum having a top-mounted argon intake is charged with 992 mg of 5-(2,6-difluorophenyl)-3-{[1-(methylsulphonyl)piperidin-4-yl]amino}-1H-pyrazolo[4,3-c]isoquinoline-7-carbonitrile trifluoroacetate, 63 ml of ethanol, 30 ml of THF and 10 ml of 9.3N sodium hydroxide. After 3 h at reflux, the mixture is cooled and poured into 250 ml of a 1M aqueous solution of potassium dihydrogen phosphate. The mixture is extracted with AcOEt, washed with saturated aqueous NaCl solution, dried over MgSO$_4$, filtered and concentrated to dryness under RP. The crude solid is dissolved in 20 ml of DMF, and then 1 g of benzotriazol-1-yloxytris(dimethylamino)phosphonium hexafluoride (BOP), 323 mg of 1-hydroxybenzotriazole (HOBT), 170 mg of ammonium chloride and 1 ml of N,N-diisopropylethylamine (DIPEA) are added. After 2 h of stirring at RT, the reaction mixture is poured into water, extracted with AcOEt, washed with a 1M aqueous solution of potassium dihydrogen phosphate and then with saturated aqueous NaCl solution. Drying over MgSO$_4$, filtering and concentration under RP are followed by purification by flash chromatography on silica gel (40-63 µm), eluting with a mixture of DCM, methanol and 4N methanolic ammonia (90/10/1 by vol.), to give 321 mg of 5-(2,6-difluorophenyl)-3-{[1-(methylsulphonyl)piperidin-4-yl]amino}-1H-pyrazolo[4,3-c]isoquinoline-7-carboxamide (lemon yellow solid). MS (E/I): m/z=500 (M+); $^1$H NMR: 1.68 (m, 2H); 2.11 (m, 2H); 2.88 (s, 3H); 2.90 (m, 2H); 3.56 (m, 2H); 3.80 (m, 1H); 6.09 (d, J=8.0 Hz, 1H); 7.33 (t, J=8.0 Hz, 2H); 7.57 (broad s, 1H); 7.69 (m, 1H); 8.17 (broad s, 1H); 8.23 (broad s, 1H); 8.36 (broad d, J=8.5 Hz, 1H); 8.45 (d, J=8.5 Hz, 1H); 12.85 (s, 1H).

Example 2

5-(2,6-difluorophenyl)-3-{[1-(methylsulphonyl)piperidin-4-yl]amino}-1H-pyrazolo[4,3-c]isoquinoline-7-carbaldehyde oxime Step 1: A 250 ml round-bottomed flask equipped with a septum having a top-mounted argon intake is charged with 2.4 g of 5-(2,6-difluorophenyl)-7-iodo-1H-pyrazolo[4,3-c]isoquinoline, prepared in step 6 of example 1, in 80 ml of DMF, 0.80 ml of bromine and 1.4 g of KOH. After 1 h at RT, the mixture is poured into iced water. The organic phase is extracted with 3 times 150 ml of AcOEt. The organic extracts are combined, washed with saturated NaCl solution, dried over MgSO$_4$ and evaporated under RP. This gives 2.23 g of 3-bromo-5-(2,6-difluorophenyl)-7-iodo-1H-pyrazolo[4,3-c]isoquinoline (cream solid), which is used as it is for the following step. MS (E/I): m/z=486 (M+).

Step 2: A 250 ml round-bottomed flask equipped with a magnetic stirrer and with a septum having a top-mounted argon intake is charged with 2.22 g of 3-bromo-5-(2,6-difluorophenyl)-7-iodo-1H-pyrazolo[4,3-c]isoquinoline in 11 ml of DMF. After argon has been bubbled through the mixture for 10 min, 1.47 ml of tributylvinylstannane and 481 mg of bis(triphenylphosphene)palladium(II) dichloride are added. The mixture is heated at 100° C. for 1 h and then after cooling is evaporated to dryness under vacuum. This gives an oil which is taken up in 350 ml of AcOEt and 300 ml of 20% aqueous KF solution. The mixture is stirred at RT for 30 min and then the suspension is filtered on a glass frit bearing a bed of Clarcel Flo. The organic phase is extracted with AcOEt and then washed with saturated aqueous NaCl solution, dried over MgSO$_4$ and evaporated to dryness under RP. This gives 3.1 g of a crude product, which is purified by chromatography on silica gel (20-45 µm), eluting with a mixture of DCM and methanol (95/5 by vol.), to give 1.44 g of 3-bromo-5-(2,6-difluorophenyl)-7-vinyl-1H-pyrazolo[4,3-c]isoquinoline (light yellow solid). MS (E/I): m/z=386 (M+); $^1$H NMR: 5.43 (d, J=11.2 Hz, 1H); 6.00 (d, J=17.6 Hz, 1H); 6.92 (dd, J=17.6, 11.2 Hz, 1H); 7.37 (t, J=7.9 Hz, 2H); 7.65 (broad s, 1H); 7.73 (m, 1H); 8.33 (dd, J=8.8, 1.5 Hz, 1H); 8.51 (d, J=8.8 Hz, 1H); 14.59 (broad m, 1H).

Step 3: A 150 ml round-bottomed flask equipped with a magnetic stirrer and with a septum having a top-mounted argon intake is charged with 1 g of 3-bromo-5-(2,6-difluorophenyl)-7-vinyl-1H-pyrazolo[4,3-c]isoquinoline in 13 ml of THF and then 7 ml of water, 13 ml of tert-butanol, 0.79 ml of a solution of osmium tetroxide at 2.5% in 2-methyl-2-propanol, and 17 g of sodium periodate are added. The mixture is stirred at RT for 3 h and then poured into water, extracted with AcOEt, washed with saturated NaCl solution, dried over MgSO$_4$, filtered and concentrated under RP. This gives 1.047 g of a crude product, which is purified by chromatography on silica gel (20-45 µm), eluting with a mixture of DCM and methanol (95/5 by vol.), to give 686 mg of 3-bromo-5-(2,6-difluorophenyl)-1H-pyrazolo[4,3-c]isoquinoline-7-carbaldehyde (cream solid). MS (E/I): m/z=388 (M+); $^1$H NMR: 7.41 (d, J=7.9 Hz, 2H); 7.77 (m, 1H); 8.34

(broad s, 1H); 8.47 (dd, J=8.5, 1.2 Hz, 1H); 8.69 (d, J=8.5 Hz, 1H); 10.15 (s, 1H); 14.89 (broad m, 1H).

Step 4: A 150 ml round-bottomed flask equipped with a magnetic stirrer and with a septum having a top-mounted argon intake is charged with 780 mg of 3-bromo-5-(2,6-difluorophenyl)-1H-pyrazolo[4,3-c]isoquinoline-7-carbaldehyde in 20 ml of DMF, 2.5 ml of diisopropylethylamine and 0.75 ml of 2-(trimethylsilyl)ethoxymethyl chloride. The mixture is stirred at RT for 24 h and then poured into water, extracted with AcOEt, washed with saturated NaCl solution, dried over $MgSO_4$, filtered and concentrated under RP. This gives 1.18 g of a crude product, which is purified by chromatography on silica gel (20-45 µm), eluting with a mixture of DCM and methanol (99.5/0.5 by vol.), to give on one hand 545 mg of 3-bromo-5-(2,6-difluorophenyl)-1-(2-trimethylsilanylethoxymethyl)-1H-pyrazolo[4,3-c]isoquinoline-7-carbaldehyde in the form of a cream solid: MS (E/I): m/z=388 (M+); $^1$H NMR: −0.13 (s, 9H); 0.86 (t, J=7.8 Hz, 2H); 3.66 (t, J=7.8 Hz, 2H); 618 (s, 2H); 7.43 (t, J=7.9 Hz, 2H); 7.79 (m, 1H); 8.39 (broad s, 1H) 8.48 (dd, J=8.3, 1.5 Hz, 1H) 8.80 (d, J=8.3 Hz, 1H) 10.17 (s, 1H), and on the other hand 354 mg of 3-bromo-5-(2,6-difluorophenyl)-2-(2-trimethylsilanylethoxymethyl)-2H-pyrazolo[4,3-c]isoquinoline-7-carbaldehyde (cream solid). MS (E/I): m/z=388 (M+); $^1$H NMR: −0.08 (s, 9H); 0.90 (t, J=8.0 Hz, 2H); 3.73 (t, J=8.0 Hz, 2H); 5.91 (s, 2H); 7.41 (t, J=7.8 Hz, 2H); 7.77 (m, 1H); 8.22 (broad s, 1H) 8.42 (dd, J=8.3, 1.5 Hz, 1H) 8.72 (d, J=8.3 Hz, 1H) 10.13 (s, 1H).

Step 5: A 50 ml round-bottomed flask equipped with a magnetic stirrer and with a septum having a top-mounted argon intake is charged with 348.4 mg of 3-bromo-5-(2,6-difluorophenyl)-2-(2-trimethylsilanylethoxymethyl)-2H-pyrazolo[4,3-c]isoquinoline-7-carbaldehyde in 12.5 ml of 1,4-dioxane. After argon has been bubbled through for 10 min, the initial charge is admixed with 320 mg of 1-methanesulphonylpiperidin-4-ylamine, 1.1 g of caesium carbonate, 62 mg of 9,9-dimethyl-4.5° bis(diphenylphosphino)xanthene and 20 mg of palladium(II) acetate. The mixture is heated at reflux for 4 h. After cooling, the mixture is poured into water, extracted with AcOEt, washed with saturated NaCl solution, dried over $MgSO_4$, filtered and concentrated under RP. It is purified by flash chromatography on silica gel (20-45 µm), eluting with a mixture of DCM and AcOEt (85/15 by vol.), to give 217 mg of 5-(2,6-difluorophenyl)-3-{[1-(methylsulphonyl)piperidin-4-yl]amino}-1-{[2-(trimethylsilyl)ethoxy]methyl}-1H-pyrazolo[4,3-c]isoquinoline-7-carbaldehyde (yellow solid). MS (E/I): m/z=615 (M+); $^1$H NMR: 0.05 (s, 9H); 0.89 (t, J=8.1 Hz, 2H); 1.62 (m, 2H); 2.12 (m, 2H); 2.75 (m, 2H); 2.85 (s, 3H); 3.59 (m, 2H); 3.67 (t, J=8.1 Hz, 2H); 4.46 (m, 1H); 5.68 (s, 2H); 6.63 (d, J=8.3 Hz, 1H); 7.37 (broad t, J=7.8 Hz, 2H); 7.68 (m, 1H); 8.06 (broad s, 1H); 8.25 (dd, J=8.4, 1.7 Hz, 1H); 8.52 (d, J=8.4 Hz, 1H); 10.08 (s, 1H).

Step 6: A 100 ml round-bottomed flask equipped with a magnetic stirrer and with a septum having a top-mounted argon intake is charged with 211 mg of 5-(2,6-difluorophenyl)-3-{[1-(methylsulphonyl)piperidin-4-yl]amino}-1-{[2-(trimethylsilyl)ethoxy]methyl}-1H-pyrazolo[4,3-c]isoquinoline-7-carbaldehyde in 8.5 ml of pyridine, 36 mg of hydroxylamine hydrochloride are added, and the mixture is stirred at RT for 64 h. It is concentrated under RP and the solid obtained is taken up in AcOEt, washed with a 1M aqueous solution of potassium phosphate and then with saturated aqueous NaCl solution, dried over $MgSO_4$, filtered and concentrated under RP. Purification is carried out by flash chromatography on silica gel (20-45 µm), eluting with a mixture of DCM and AcOEt (75/25 by vol.), to give 184 mg of 5-(2,6-difluorophenyl)-3-{[1-(methylsulphonyl)piperidin-4-yl]amino}-1-{[2-(trimethylsilyl)ethoxy]methyl}-1H-pyrazolo[4,3-c]isoquinoline-7-carbaldehyde oxime (yellow solid). MS (E/I): m/z=630 (M+); $^1$H NMR: 0.04 (s, 9H); 0.89 (m, 2H); 1.61 (m, 2H); 2.11 (m, 2H); 2.74 (m, 2H); 2.85 (s, 3H); 3.58 (m, 2H); 3.67 (m, 2H); 4.46 (m, 1H); 5.65 (s, 2H); 6.50 (d, J=8.3 Hz, 1H); 7.33 (broad t, J=8.1 Hz, 2H); 7.65 (m, 1H); 7.72 (broad s, 1H); 8.01 (dd, J=8.4, 17 Hz, 1H); 8.27 (s, 1H); 8.35 (d, J=8.4 Hz, 1H); 11.39 (s, 1H).

Step 7: A 50 ml round-bottomed flask equipped with a septum having a top-mounted argon intake is charged with 180 mg of 5-(2,6-difluorophenyl)-3-{[1-(methylsulphonyl)piperidin-4-yl]amino}-1-{[2-(trimethylsilyl)ethoxy]methyl}-1H-pyrazolo[4,3-c]isoquinoline-7-carbaldehyde oxime in 15 ml of DCM. After cooling to 0° C. using an ice bath, 1.8 ml of TFA are added and the mixture is stirred at RT for 6 h. The mixture is concentrated under RP and the solid obtained is taken up in 50 ml of water and 2 ml of 0.75M aqueous ammonia solution. It is extracted with AcOEt, washed with saturated NaCl solution, dried over $MgSO_4$, filtered and concentrated under RP. Chromatography on silica gel (20-45 µm), eluting with a mixture of DCM and methanol (92.5/7.5 by vol.), gives 63 mg of 5-(2,6-difluorophenyl)-3-{[1-(methylsulphonyl)piperidin-4-yl]amino}-1H-pyrazolo[4,3-c]isoquinoline-7-carbaldehyde oxime (lemon yellow solid). MS (E/I): m/z=500 (M+); $^1$H NMR: 1.67 (m, 2H); 2.11 (m, 2H); 2.87 (s, 3H); 2.89 (m, 2H); 3.56 (m, 2H); 3.79 (m, 1H); 6.06 (d, J=7.8 Hz, 1H); 7.32 (broad t, J=7.6 Hz, 2H); 7.67 (m, 1H); 7.84 (broad s, 1H); 8.14 (broad d, J=8.5 Hz, 1H); 8.30 (s, 1H); 8.41 (d, J=8.5 Hz, 1H); 11.43 (s, 1H); 12.81 (s, 1H).

Example 3

5-(2,6-difluorophenyl)-3-{[1-(methylsulphonyl)piperidin-4-yl]amino}-1H-pyrazolo[4,3-c]isoquinolin-7-yl]methanol Step 1: A 250 ml round-bottomed flask equipped with a magnetic stirrer and with a septum having a top-mounted argon intake is charged with 45 mg of 5-(2,6-difluorophenyl)-3-{[1-(methylsulphonyl)piperidin-4-yl]amino}-1-{[2-(trimethylsilyl)ethoxy]methyl}-1H-pyrazolo[4,3-c]isoquinoline-7-carbaldehyde, prepared in step 5 of example 2, in 1.5 ml of THF and 1.5 ml of methanol. After cooling to 0° C. using an ice bath, 5.5 mg of $NaBH_4$ are added and the mixture is stirred for 30 min. Then 1.5 ml of acetone are added and the mixture is poured into saturated aqueous sodium bicarbonate solution. It is extracted with AcOEt, washed with saturated NaCl solution, dried over $MgSO_4$, filtered and concentrated under RP. This gives 46 mg of [5-(2,6-difluorophenyl)-3-{[1-(methylsulphonyl)piperidin-4-yl]amino}-1-{[2-(trimethylsilyl)ethoxy]methyl}-1H-pyrazolo[4,3-c]isoquinolin-7-yl]methanol, which is used as it is for the following step. MS (E/I): m/z=617 (M+).

Step 2; A 30 ml round-bottomed flask equipped with a magnetic stirrer and with a septum having a top-mounted argon intake is charged with 46 mg of [5-(2,6-difluorophenyl)-3-{[1-(methylsulphonyl)piperidin-4-yl]amino}-1-{[2-(trimethylsilyl)ethoxy]methyl}-1H-pyrazolo[4,3-c]isoquinolin-7-yl]methanol in 4 ml of DCM. After cooling to 0° C. using an ice bath, 0.45 ml of TFA are added and the mixture is stirred at RT for 2 h. It is concentrated under RP and the solid obtained is taken up in 25 ml of water and 0.75 ml of a 0.75M aqueous ammonia solution. It is extracted with AcOEt, washed with saturated NaCl solution, dried over $MgSO_4$, filtered and concentrated under RP. Chromatography on silica gel (20-45 µm), eluting with a mixture of DCM and methanol (92.5/7.5 by vol.), gives 13 mg of [5-(2,6-difluorophenyl)-3-{[1-(methylsulphonyl)piperidin-4-yl]amino}-1H-pyrazolo[4,3-c]isoquinolin-7-yl]methanol (yellow solid). MS (E/I): m/z=487 (M+); $^1$H NMR: 1.67 (m, 2H); 2.11 (m, 2H); 2.87 (s, 3H); 2.90 (m, 2H); 3.56 (m, 2H); 3.79 (m, 1H); 4.63 (d,. J=57 Hz, 2H); 5.34 (t, J=5.7 Hz, 1H); 5.98 (d, J=7.8 Hz, 1H); 7.31 (m, 2H); 7.59 (broad s, 1H); 7.66 (m, 1H); 7.83 (broad d, J=8.3 Hz, 1H); 8.35 (d, J=8.3, 1H); 12.68 (s, 1H).

Example 4

5-(2,6-difluorophenyl)-3-{[1-(trifluoromethanesulphonyl)piperidin-4-yl]amino}-1H-pyrazolo[4,3-c]isoquinoline-7-carboxamide Step 1: The procedure is as in example 1, step 12. A 50 ml round-bottomed flask equipped with a magnetic stirrer and with a septum having a top-mounted argon intake is charged with 200 mg of 3-bromo-5-(2,6-difluorophenyl)-1-{[2-(trimethylsilyl)ethoxy]methyl}-1H-pyrazolo[4,3-c]isoquinoline-7-carbonitrile in 4 ml of 1,4-dioxane. After argon has been bubbled through for 10 min, 269 mg of 1-trifluoromethanesulphonylpiperidin-4-ylamine trifluoroacetate, 543 mg of caesium carbonate, 22 mg of 9,9-dimethyl-4,5-bis(diphenylphosphino)xanthene and 8.7 mg of palladium(II) acetate are added. The mixture is heated at reflux for 2 h. After cooling, the mixture is poured into water, extracted with AcOEt, washed with saturated NaCl solution, dried over MgSO$_4$, filtered and concentrated under RP. It is purified by flash chromatography on silica gel (15-40 µm), eluting with a mixture of AcOEt and heptane (40/60 by vol.), to give 272 mg of 5-(2,6-difluorophenyl)-3-{[1-(trifluoromethanesulphonyl)piperidin-4-yl]amino}-1-{[2-(trimethylsilyl)ethoxy]methyl}-1H-pyrazolo[4,3-c]isoquinoline-7-carbonitrile (pale yellow solid). MS (E/I): m/z=666 (M+).

Synthesis of 1,1-dimethylethyl (1-trifluoromethanesulphonylpiperidin-4-yl)carbamate A 150 ml round-bottomed flask equipped with a magnetic stirrer is charged under argon with 2 g of 4-N-boc-aminopiperidine in 35 ml of DCM, 82 mg of 4-dimethylaminopyridine (DMAP) and 1.86 ml of triethylamine. After cooling to 0° C. using an ice bath, 1.6 ml of trifluoromethanesulphonyl chloride are added dropwise. The mixture is stirred at 0° C. for 30 min and then at RT for 1 h. It is poured into 100 ml of saturated aqueous sodium bicarbonate solution. It is extracted with AcOEt, washed with saturated aqueous NaCl solution, dried over MgSO$_4$, filtered and concentrated to dryness under RP. Chromatography on silica gel (15-40 µm), eluting with a mixture of DCM and methanol (98/02 by vol.), gives 1.5 g of 1,1-dimethylethyl (1-trifluoromethanesulphonylpiperidin-4-yl)carbamate (cream solid). MS (E/I): m/z=232 (M+).

A 150 ml round-bottomed flask is charged with 1.37 g of 1,1-dimethylethyl (1-trifluoromethanesulphonylpiperidin-4-yl)carbamate in 30 ml of DCM. 3 ml of TFA are added and the mixture is stirred at RT for 1 h. It is concentrated under RP and the solid obtained is taken up in 30 ml of water and 2 ml of 0.75M aqueous ammonia solution. The product is extracted with AcOEt, dried over MgSO$_4$, filtered and concentrated under RP. This gives 1.2 g of 1-trifluoromethanesulphonylpiperidin-4-ylamine trifluoroacetate (off-white solid). MS (E/I): m/z=346 (M+).

Step 2; A 30 ml round-bottomed flask equipped with a magnetic stirrer and with a septum having a top-mounted argon intake is charged with 272 mg of 5-(2,6-difluorophenyl)-3-{[1-(trifluoromethanesulphonyl)piperidin-4-yl]amino}-1-{[2-(trimethylsilyl)ethoxy]methyl}-1H-pyrazolo[4,3-c]isoquinoline-7-carbonitrile, 10 ml of ethanol, 5 ml of THF and 0.611 ml of 9.3N NaOH. After 2 h of reflux, the mixture is cooled, and 50 ml of a 1M aqueous solution of potassium dihydrogen phosphate are poured in. The product is extracted with AcOEt, washed with saturated aqueous NaCl solution, dried over MgSO$_4$, filtered and concentrated to dryness under RP. The crude solid obtained is dissolved in 4 ml of DMF and than 275 mg of benzotriazol-1-yloxytris(dimethylamino)phosphonium hexafluoride (BOP), 84 mg of 1-hydroxybenzotriazole (HOBT), 44 mg of ammonium chloride and 2 ml of N,N-diisopropylethylamine (DIPEA) are added. After 3 h at RT, the mixture is poured into water, extracted with AcOEt, and washed with saturated aqueous NaCl solution. Drying of MgSO$_4$, filtering and concentration under RP give 300 mg of 5-(2,6-difluorophenyl)-3-{[1-(trifluoromethanesulphonyl)piperidin-4-yl]amino}-1-{[2-(trimethylsilyl)ethoxy]methyl}-1H-pyrazolo[4,3-c]isoquinoline-7-carboxamide. MS (E/I): m/z=684 (M+).

Step 3: A 50 ml round-bottom flask equipped with a magnetic stirrer and with a septum having a top-mounted argon intake is charged with 300 mg of 5-(2,6-difluorophenyl)-3-{[1-(trifluoromethanesulphonyl)piperidin-4-yl]amino}-1-{[2-(trimethylsilyl)ethoxy]methyl}-1H-pyrazolo[4,3-c]isoquinoline-7-carboxamide in 8 ml of DCM. 3 ml of TFA are added and the mixture is stirred at RT for 2 h. It is concentrated under RP and the solid obtained is taken up in 30 ml of water and 2 ml of 0.75M aqueous ammonia solution. The product is extracted with AcOEt, dried over MgSO$_4$, filtered and concentrated under RP. Chromatography on silica gel (15-40 µm), eluting with AcOEt, gives 30 mg of 5-(2,6-difluorophenyl)-3-{[1-(trifluoromethanesulphonyl)piperidin-4-yl]amino}-1H-pyrazolo[4,3-c]isoquinoline-7-carboxamide (pale yellow solid). MS (E/I): m/z=554 (M+); $^1$H NMR: 1.69 (m, 2H); 2.17 (m, 2H); 3.38 (m, 2H); 3.83 (m, 2H); 3.93 (m, 1H); 6.24 (m, 1H); 7.33 (t, J=8.0 Hz, 2H); 7.58 (broad s, 1H); 7.69 (m, 1H); 8.17 (broad s, 1H); 8.23 (broad s, 1H); 8.36 (broad d, J=8.5 Hz, 1H); 8.44 (d, J=8.5 Hz, 1H); 12.9 (broad s, 1H).

Example 5

5-(2,6-difluorophenyl)-3-{[1-(methylsulphonyl)piperidin-4-yl]amino}-7-vinyl-1H-pyrazolo[4,3-c]isoquinoline Step 1: A 250 ml round-bottomed flask equipped with a magnetic stirrer and with a septum having a top-mounted argon intake is charged with 380 mg of 3-bromo-5-(2,6-difluorophenyl)-7-vinyl-1H-pyrazolo[4,3-c]isoquinoline, as prepared in step 2 of example 2, in 10 ml of DMF, 1.2 ml of diisopropylethylamine and 0.37 ml of 2-(trimethylsilyl)ethoxymethyl chloride. The mixture is stirred at RT for 24 h and then poured into water, extracted with AcOEt, washed with saturated NaCl solution, dried over MgSO$_4$, filtered and concentrated under RP. This gives 548 mg of crude product, which is purified by chromatography on silica gel (20-45 µm), eluting with a mixture of DCM and methanol (99.5/0.5 by vol.), to give on one hand 198 mg of 3-bromo-5-(2,6-difluorophenyl)-1-(2' trimethylsilanylethoxymethyl)-7-vinyl-1H-pyrazolo[4,3-c]isoquinoline, in the form of a cream solid, and on the other hand 194 mg of 3-bromo-5-(2,6-difluorophenyl)-2-(2-trimethylsilanylethoxymethyl)-7-vinyl-2H-pyrazolo[4,3-c]isoquinoline (cream solid). MS (E/I): m/z=516 (M+); $^1$H NMR: 0.05 (s, 9 H); 0.92 (t, J=7.8 Hz, 2 H); 3.73 (t, J=7.8 Hz, 2 H); 5.39 (d, J=11.1 Hz, 1 H); 5.87 (s, 2 H); 5.94 (d, J=17.7

Hz, 1 H) 6.90 (dd, J=17.7, 11.1 Hz, 1 H) 7.39 (t, J=7.8 Hz, 2 H) 7.57 (broad s, 1 H) 7.73 (m, 1 H) 8.21 (dd, J=8.5, 1.5 Hz, 1 H) 8.51 (d, J=8.5 Hz, 1 H).

Step 2: A 30 ml round-bottomed flask equipped with a magnetic stirrer and with a septum having a top-mounted argon intake is charged with 189 mg of 3-bromo-5-(2,6-difluorophenyl)-2-(2-trimethylsilanylethoxymethyl)-7-vinyl-2H-pyrazolo[4,3-c]isoquinoline in 5 ml of 1,4-dioxane. After argon has been bubbled through for 10 min, 130 mg of 1-methanesulphonylpiperidin-4-ylamine, 453 mg of caesium carbonate, 25 mg of 9,9-dimethyl-4,5-bis(diphenylphosphino)xanthene and 8 mg of palladium(II) acetate are added. The mixture is heated at reflux for 4 h. After cooling, the mixture is poured into water, extracted with AcOEt, washed with saturated NaCl solution, dried over $MgSO_4$, filtered and concentrated under RP. It is purified by flash chromatography on silica gel (15-40 µm), eluting with a mixture of DCM and AcOEt (85/15 by vol.), to give 96 mg of 5-(2,6-difluorophenyl)-3-{[1-(methylsulphonyl)piperidin-4-yl]amino}-2-{[2-(trimethylsilyl)ethoxy]methyl}-7-vinyl-2H-pyrazolo[4,3-c]isoquinoline (yellow solid). MS (E/I): m/z=613 (M+); $^1$H NMR: 0.04 (s, 9 H) 0.89 (t, J=8.3 Hz, 2 H) 1.60 (m, 2 H) 2.10 (m, 2 H) 2.74 (m, 2 H) 2.84 (s, 3 H) 3.58 (m, 2 H) 3.66 (t, J=8.3 Hz, 2 H) 4.44 (m, 1 H) 5.33 (d, J=11.0 Hz, 1 H) 5.64 (s, 2 H) 5.87 (d, J=17.7 Hz, 1 H) 6.47 (d, J=7.8 Hz, 1 H) 6.83 (dd, J=17.7, 11.0 Hz, 1 H) 7.33 (t, J=7.8 Hz, 2 H) 7.42 (broad s, 1 H) 7.64 (m, 1 H) 8.02 (dd, J=8.3, 1.5 Hz, 1 H) 8.31 (d, J=8.3 Hz, 1 H).

Step 3; A 30 ml round-bottomed flask equipped with a magnetic stirrer and with a septum having a top-mounted argon intake is charged with 92 mg of 5-(2,6-difluorophenyl)-3-{1-(methylsulphonyl)piperidin-4-yl]amino}-2-{[2-(trimethylsilyl)ethoxy]methyl}-7-vinyl-2H-pyrazolo[4,3-c]isoquinoline in 8 ml of DCM. After cooling to 0° C. using an ice bath, 0.9 ml of TFA are added and the mixture is stirred at RT for 2 h. The mixture is concentrated under RP and the solid obtained is taken up in 30 ml of water and 1.5 ml of 0.75M aqueous ammonia solution. The product is extracted with AcOEt, dried over $MgSO_4$, filtered and concentrated under RP. It is purified by flash chromatography on silica gel (15-40 µm), eluting with a DCM/methanol mixture (95/05 by vol.). This gives 14 mg of 5-(2,6-difluorophenyl)-3-{[1-(methylsulphonyl)piperidin-4-yl]amino}-7-vinyl-2H-pyrazolo[4,3-c]isoquinoline (yellow solid). MS (E/I): m/z=483 (M+); $^1$H NMR: 1.67 (m, 2 H) 2.11 (m, 2 H) 2.87 (s, 3 H) 2.90 (m, 2 H) 3.56 (m, 2 H) 3.79 (m, 1 H) 5.37 (d, J=11.2 Hz, 1 H) 5.94 (d, J=17.6 Hz, 1 H) 6.01 (broad d, J=8.3 Hz, 1 H) 6.87 (dd. J=17.6, 11.2 Hz, 1 H) 7.32 (t, J=7.8 Hz, 2 H) 7.53 (broad s, 1 H) 7.67 (m, 1 H) 8.17 (broad d, J=8.8 Hz, 1 H) 8.39 (d, J=8.8 Hz, 1 H) 12.73 (s, 1 H).

Example 6

5-(2,6-difluorophenyl)-7-fluoro-3-{[1-(methylsulphonyl)piperidin-4-yl]amino}-1H-pyrazolo[4,3-c]isoquinoline Step 1: A 50 ml round-bottomed flask equipped with a magnetic stirrer and with a septum having a top-mounted argon intake is charged with 4.2 g of 2-bromo-1-(4-fluorophenyl)ethanone in 10 ml of DMF and 3.6 g of potassium phthalimide. The mixture is stirred at RT for 4 h and the precipitate formed is filtered off on a glass frit and washed with 3 times 50 ml of isopropyl ether. This, after drying under RP, gives 5 g of 2-[2-(4-fluorophenyl)-2-oxoethyl]isoindole-1,3-dione (white solid), which is used as it is in the following step. Melting point (Kofler): 140° C.; MS (E/I): m/z=283 (M+); $^1$H NMR: 5.25 (s, 2 H) 7.44 (t, J=9.0 Hz, 2 H) 7.85-8.00 (m, 4 H) 8.19 (dd, J=9.8, 5.4 Hz, 2 H).

Step 2: A 100 ml round-bottomed flask equipped with a septum having a top-mounted argon intake and with a magnetic stirrer is charged with 5 g of 2-[2-(4-fluorophenyl)-2-oxoethyl]isoindole-1,3-dione in 25 ml of N,N-dimethylformamide diethyl acetal. The mixture is heated at reflux for 15 h and then cooled using an ice bath to 0° C. The precipitate formed is filtered off with suction on a glass frit, washed with two times 50 ml of isopropyl ether, and then two clarifying washes are carried out (washing of the cake without stirring) with 50 ml of isopropyl ether. Drying under RP gives 4.5 g of a mixture of the E and Z isomers of 2-[2-dimethylamino-1-(4-fluorobenzoyl)-vinyl]isoindole-1,3-dione (orange-yellow solid). m.p. (Kofler): 228° C.; MS (E/I): m/z=338 (M+); $^1$H NMR: 2.94 (broad m, 6H) 7.25 (t, J=9.0 Hz, 2 H) 7.46-7.57 (m, 3 H) 7.86-8.00 (m, 4H).

Step 3: A 1 l round-bottomed flask equipped with an effective magnetic stirrer and with a condenser having a top-mounted argon intake is charged at RT with 4.5 g of 2-[2-dimethylamino-1-(4-fluorobenzoyl)vinyl]isoindole-1,3-dione in 30 ml of ethanol. This gives a brown suspension, which is admixed with 1.62 ml of hydrazine hydrate in 20 ml of ethanol. The suspension is heated to reflux. After 30 min of heating, the mixture may be observed to thicken and take on a lemon yellow colour. This suspension is stirred at reflux for 3 h and then the mixture is brought to RT. The insolubles are filtered off on a frit and washed with 2×20 ml of isopropyl ether. The filtrate is concentrated to dryness to give 6 g of a beige solid. The crude mixture is admixed with 50 ml of water and 20 ml of 2M hydrochloric acid. 50 ml of AcOEt are added and the insolubles are filtered off. The aqueous phase is separated off and taken up in 3×15 ml of AcOEt. The aqueous phase is basified by addition of 2M sodium hydroxide to a pH of 11 and then extracted with 3×20 ml of ethyl acetate. The organic phase is washed with water until a neutral pH is obtained. It is extracted with AcOEt, dried over $MgSO_4$, filtered and concentrated to dryness. This gives 1.93 g of 3-(4-fluorophenyl)-1H-pyrazol-4-ylamine (mauvish oil). MS (E/I): m/z=177 (M+); $^1$H NMR: For this batch, a mixture of tautomers is observed, and all of the absorptions are broad, with: 3.69-4.15 (m, 2 H) 7.09-7.34 (m, 3 H) 7.51-8.08 (m, 2H) 12.10-12.50 (m, 1 H).

Step 4: A round-bottomed flask equipped with a magnetic stirrer and with a septum having a top-mounted argon intake is charged with 1.93 g of 3-(4-fluorophenyl)-1H-pyrazol-4-ylamine in 20 ml of DCM and 15 ml of pyridine. The mixture is cooled to 0° C. using an ice bath, and 1.7 ml of 2,6-difluorobenzoic chloride are added. The temperature is allowed to climb gradually to room temperature over 3 h. Following evaporation of the solvent under RP, water is added to the crude reaction mixture and then the aqueous phase is extracted with AcOEt. The organic extracts are combined, washed with saturated NaCl solution and dried over $MgSO_4$. The AcOEt is then evaporated under vacuum to give 3 g of a mixture of 2,6-difluoro-N-[5-(4-fluorophenyl)-1H-pyrazol-4-yl]benzamide and N-(1-(2,6-difluorobenzoyl)-5-(4-fluorophenyl)-1H-pyrazol-4-yl]-2,6-difluorobenzamide in the form of a beige solid, which is used as it is. The crude reaction product is treated to give solely the expected product: in a round-bottomed flask, 3 g of the mixture of 6-difluoro-N-[5-(4-fluorophenyl)-1H-pyrazol-4-yl]benzamide and N-[1-(2,6-difluorobenzoyl)-5-(4-fluorophenyl)-1H-pyrazol-4-yl]-2,6-difluorobenzamide are dissolved, at RT and under argon, in 20 ml of methanol and 12 ml of tetrahydrofuran, and then 6 ml of 5N aqueous sodium hydroxide solution are added. After 1 h at RT, the mixture is poured into 6 ml of 5N hydrochloric acid. It is extracted with AcOEt and the organic phases are washed with saturated NaCl solution, dried over MgSO$_4$ and then concentrated under RP. This gives 2.6 g of 2,6-difluoro-N-[5-(4-fluorophenyl)-1H-pyrazol-4-yl]benzamide (cream solid). MS (E/I): m/z=317 (M+); $^1$H NMR: 7.21 (t, J=7.8 Hz, 2 H) 7.26 (broad m, 2 H) 7.56 (m, 1 H) 7.73 (broad m, 2 H) 8.02 (broad m, 1 H) 10.21 (s, 1 H) 12.95-13.29 (broad m, 1H); m.p.=112° C.

Step 5: A 250 ml round-bottomed flask equipped with a magnetic stirrer and with a septum having a top-mounted argon intake is charged with 2.6 g of 2,6-difluoro-N-[5'(4-fluorophenyl)-1H-pyrazol-4-yl]benzamide, 60 ml of phenylphosphine dichloride and 17.5 g of phosphorus pentoxide. After 23 h of heating at 165° C., the mixture is cooled to RT and then poured into a mixture of 260 ml of water and 400 g of ice. The temperature rises to 40° C. The mixture is neutralized by slow addition of 120 ml of 28% aqueous ammonia. It is extracted with AcOEt, washed with saturated NaCl solution and dried over MgSO$_4$, then concentrated under RP. The product is purified by flash chromatography on silica gel (15-40 μm), eluting with a mixture of DCM and methanol (99/1 by vol.), to give 680 mg of 5-(2,6-difluorophenyl)-7-fluoro-1H-pyrazolo[4,3-c]isoquinoline (cream solid). MS (E/I): m/z=299 (M+); $^1$H NMR: 7.34 (t, J=7.8 Hz, 2 H) 7.38 (broad m, 1 H) 7.70 (m, 1 H) 7.96 (broad t, J=9.1 Hz, 1 H) 8.48 (broad s, 1 H) 8.63 (dd, J=9.1, 5.6 Hz, 1 H) 14.29 (broad s, 1 H).

Step 6; A 250 ml round-bottomed flask equipped with a magnetic stirrer and with a septum having a top-mounted argon intake is charged with 680 mg of 5-(2,6-difluorophenyl)-7-fluoro-1H-pyrazolo[4,3-c]isoquinoline in 10 ml of DMF, 0.21 ml of bromine and 344 mg of KOH. After 5 h at RT, the mixture is poured into ice-water. The aqueous phase is extracted with 3×150 ml of AcOEt. The organic extracts are combined, washed with saturated NaCl solution, dried over MgSO$_4$ and evaporated under RP. This gives 770 mg of 3-bromo-5-(2,6-difluorophenyl)-7-fluoro-1H-pyrazolo[4,3-c]isoquinoline (yellow solid), which is used as it is for the following step. MS (E/I): m/z=378 (M+); $^1$H NMR: 7.38 (t, J=8.1 Hz, 2 H) 7.45 (broad d, J=9.2 Hz, 1H) 7.74 (m, 1 H) 8.03 (broad td, J=9.2, 2.9 Hz, 1 H) 8.63 (dd, J=9.2, 5.4 Hz, 1 H) 14.69 (broad m, 1 H).

Step 7: A 50 ml round-bottomed flask equipped with a magnetic stirrer and with a septum having a top-mounted argon intake is charged with 770 mg of 3-bromo-5-(2,6-difluorophenyl)-7-fluoro-1H-pyrazolo[4,3-c]isoquinoline in 15 ml of DMF, 2.5 ml of N,N-diisopropylethylamine and 0.76 ml of 2-(trimethylsilyl)ethoxymethyl chloride. After 5 h at RT, the mixture is poured into 8 volumes of ice-water. The aqueous phase is extracted with 3 times 200 ml of AcOEt and the organic extracts are combined, washed with saturated NaCl solution, dried over MgSO$_4$ and concentrated under RP. This gives 520 mg of 3-bromo-5-(2,6-difluorophenyl)-7-fluoro-1-{[2-(trimethylsilyl)ethoxy]methyl}-1H-pyrazolo[4,3-c]isoquinoline (orange solid). MS (E/I): m/z=508 (M+); $^1$H NMR: 0.12 (s, 9 H) 0.85 (t, J=7.9 Hz, 2 H) 3.64 (t, J=7.9 Hz, 2 H) 6.13 (s, 2 H) 7.39 (t, J=7.8 Hz, 2 H) 7.51 (dd, J=9.2, 2.7 Hz, 1H) 7.75 (m, 1H) 8.06 (td, J=9.2; 2.7 Hz, 1H) 8.71 (dd, J=9.2, 5.4 Hz, 1H).

Step 8: A 50 ml round-bottomed flask equipped with a magnetic stirrer and with a septum having a top-mounted argon intake is charged with 520 mg of 3-bromo-5-(2,6-difluorophenyl)-7-fluoro-1-{[2-(trimethylsilyl)ethoxy]methyl}-1H-pyrazolo[4,3-c]isoquinoline in 14 ml of 1,4-dioxane. After argon has been bubbled through for 10 min, 225 mg of 1-methanesulphonylpiperidin-4-ylamine, 780 mg of caesium carbonate, 92 mg of 9,9-dimethyl-4,5-bis(diphenylphosphino)xanthene and 40 mg of palladium(II) acetate are added. The mixture is heated at reflux for 5 h. After cooling, the mixture is poured into water, extracted with AcOEt, washed with saturated NaCl solution, dried over MgSO$_4$, filtered and concentrated under RP. The product is purified by flash chromatography on silica gel (15-40 μm), eluting with a mixture of DCM and AcOEt (95/05 by vol.), to give 94 mg of 5-(2,6-difluorophenyl)-7-fluoro-3-{[1-(methylsulphonyl)piperidin-4-yl]amino}1-{[2-(trimethylsilyl)ethoxy]methyl}-1H-pyrazolo[4,3-c]isoquinoline (yellow solid). MS (E/I): m/z=605 (M+); $^1$H NMR: −0.13 (s, 9 H) 0.84 (m, 2 H) 1.69 (m, 2 H) 2.10 (m, 2 H) 2.88 (s, 3 H) 2.90 (partially masked m, 2 H) 3.57 (m, 2H) 3.62 (m, 2H) 3.77 (m, 1H) 5.89 (s, 2H) 6.28 (d, J=8.3 Hz, 1H) 7.28-7.40 (m, 3H) 7.69 (m, 1H) 7.91 (td, J=9.0, 2.9 Hz, 1H) 8.60 (dd, J=9.0, 5.4 Hz, 1H).

Step 9: A round-bottomed flask equipped with a septum having a top-mounted argon intake is charged with 95 mg of 5-(2,6-difluorophenyl)-7-fluoro-3-{[1-(methylsulphonyl)piperidin-4-yl]amino}1-([2-(trimethylsilyl)ethoxy]methyl}-1H-pyrazolo[4,3-c]isoquinoline in 10 ml of DCM. After cooling to 0° C. using an ice bath, 0.173 ml of TFA are added and the mixture is stirred at RT for 20 h. It is concentrated under RP and the solid obtained is taken up in 30 ml of water and 2 ml of 0.75M aqueous ammonia solution. The product is extracted with AcOEt, dried over MgSO$_4$, filtered and concentrated under RP. It is purified by flash chromatography on silica gel (15-40 μm), eluting with a mixture of DCM and methanol (95/05 by vol.), to give 6 mg of 5-(2,6-difluorophenyl)-7-fluoro-3-{[1-(methylsulphonyl)piperidin-4-yl]amino}-1H-pyrazolo[4,3-c]isoquinoline (yellow solid). MS (E/I): m/z=475 (M+); $^1$H NMR: 1.67 (m, 2 H) 2.10 (m, 2 H) 2.87 (s, 3 H) 2.90 (m, 2 H) 3.56 (m, 2 H) 3.79 (m, 1H) 6.08 (d, J=8.3 Hz, 1 H) 7.29 (m, 1 H) 7.33 (t, J=7.8 Hz, 2 H) 7.68 (m, 1 H) 7.88 (broad t, J=9.3 Hz, 1 H) 8.50 (dd, J=9.3, 5.4 Hz, 1 H) 12.80 (s, 1 H)*.

Example 7

5-(2,6-difluorophenyl)-3-{[1-(methylsulphonyl)piperidin-4-yl]amino}-7-ethynyl-1H-pyrazolo[4,3-c]isoquinoline Step 1: A 150 ml round-bottomed flask equipped with a magnetic stirrer and with a septum having a top-mounted argon intake is charged with 1.2 g of 3-bromo-5-(2,6-difluorophenyl)-7-iodo-1H-pyrazolo[4,3-c]isoquinoline, prepared in step 1 of example 6, in 24 ml of DMF, 3 ml of diisopropylethylamine and 0.92 ml of 2-(trimethylsilyl)ethoxymethyl chloride. The mixture is stirred at RT for 24 h and then poured into water, extracted with AcOEt, washed with saturated NaCl solution, dried over MgSO$_4$, filtered and concentrated under RP. This gives 1.52 g of crude product, which is purified by chromatography on silica gel (20-45 μm), eluting with a DCM/methanol mixture (99.5/0.5 by vol.), to give on one hand 832 mg of 3-bromo-5-(2,6-difluorophenyl)-1-(2-trimethylsilanyl ethoxymethyl)-7-iodo-1H-pyrazolo[4,3-c]isoquinoline in the form of a white solid. MS (E/I): m/z=616 (M+), and on the other hand 526 mg of 3-bromo-5-(2,6-difluorophenyl)-2-(2-trimethylsilanyl-ethoxymethyl)-7-iodo-2H-pyrazolo[4,3-c]isoquinoline (ochre oil), which is used as it is in the following step. MS (E/I): m/z=616 (M+).

Step 2: A 10 ml round-bottomed flask equipped with a magnetic stirrer and with a septum having a top-mounted argon intake is charged with 263 mg of 3-bromo-5-(2,6-difluorophenyl)-2-(2-trimethylsilanylethoxymethyl)-7-iodo-2H-pyrazolo[4,3-c]isoquinoline in 1.5 ml of DMF and then 1.5 ml of triethylamine. After argon has been bubbled through the mixture for 10 min, 30 mg of bis(triphenylphosphene)palladium(II) dichloride, 8.7 mg of copper(I) iodide and 118 µl of ethynyltrimethylsilane are added. The mixture is stirred at RT for 2 h, poured into water, extracted with AcOEt, washed with saturated NaCl solution, dried over MgSO$_4$, filtered and concentrated under RP. The product is purified by flash chromatography on silica gel (40-63 µm), eluting with a mixture of DCM and methanol (99.5/0.5 by vol.), to give 140 mg of 3-bromo-5-(2,6-difluorophenyl)-2-(2-trimethylsilanylethoxymethyl)-7-trimethylsilanylethynyl-2H-pyrazolo[4,3-c]isoquinoline (cream solid). MS (E/I): m/z=586 (M+) $^1$H NMR: −0.05 (s, 9 H) 0.23 (s, 9 H) 0.89 (m, 2 H) 3.72 (m, 2 H) 5.88 (s, 2 H) 7.4 (t, J=8.1 Hz, 2H) 7.6 (broad s, 1H) 7.75 (m, 1H) 8.01 (dd, J=8.3, 1.5 Hz, 1H) 8.52 (d, J=8.3 Hz, 1H).

Step 3: A 30 ml round-bottomed flask equipped with a magnetic stirrer and with a septum having a top-mounted argon intake is charged with 79 mg of 3-bromo-5-(2,6-difluorophenyl)-2-(2-trimethylsilanylethoxymethyl)-7-trimethylsilanylethynyl-2H-pyrazolo[4,3-c]isoquinoline in 5 ml of 1,4-dioxane. After argon has been bubbled through the reaction mixture for 10 min, 81 mg of 1-methanesulphonylpiperidin-4-ylamine, 282 mg of caesium carbonate, 16 mg of 9,9-dimethyl-4,5-bis(diphenylphosphino)xanthene and 5 mg of palladium(II) acetate are added. The mixture is heated at reflux for 5 h. After cooling, the mixture is poured into water, extracted with AcOEt, washed with saturated NaCl solution, dried over MgSO$_4$, filtered and concentrated under RP. The product is purified by flash chromatography on silica gel (40-63 µm), eluting with a DCM/methanol mixture (95/05 by vol.), to give 54 mg of 5-(2,6-difluorophenyl)-3-{[1-(methylsulphonyl)piperidin-4-yl]amino}-2-{[2-(trimethylsilyl)ethoxy]methyl}-7-trimethylsilanylethynyl-2H-pyrazolo[4,3-c]isoquinoline as a yellow solid. MS (E/I): m/z=683 (M+).

Step 4: A 30 ml round-bottomed flask equipped with a magnetic stirrer and with a septum having a top-mounted argon intake is charged with 74 mg of 5-(2,6-difluorophenyl)-3-{[1-(methylsulphonyl)piperidin-4-yl]amino}-2-{[2-(trimethylsilyl)ethoxy]methyl}-7-trimethylsilanylethynyl-2H-pyrazolo[4,3-c]isoquinoline in 5 ml of THF, 0.22 cm$^3$ of tetrabutylammonium fluoride is added, and the mixture is stirred at RT for 30 min. It is poured into water, extracted with AcOEt, washed with saturated NaCl solution, dried over MgSO$_4$, filtered and concentrated under RP. The product is purified by flash chromatography on silica gel (40-63 µm), eluting with a mixture of DCM and AcOEt (85/15 by vol.), to give 47 mg of 5-(2,6-difluorophenyl)-3-{[1-(methylsulphonyl)piperidin-4-yl]amino}-2-{[2-(trimethylsilyl)ethoxy]methyl}-7-ethynyl-2H-pyrazolo[4,3-c]isoquinoline (lemon yellow solid). MS (E/I): m/z=611 (M+).

Step 5: A 30 ml round-bottomed flask equipped with a septum having a top-mounted argon intake is charged with 47 mg of 5-(2,6-difluorophenyl)-3-({1-(methylsulphonyl)piperidin-4-yl]amino}-2-{[2-(trimethylsilyl)ethoxy]methyl}-7-ethynyl-2H-pyrazolo[4,3-c]isoquinoline in 4 ml of DCM. After cooling to 0° C. using an ice bath, 0.47 ml of TFA is added and the mixture is stirred at RT for 3 h. It is concentrated under RP and the solid obtained is taken up in 25 ml of water and 0.75 ml of 0.75M aqueous ammonia solution. It is extracted with AcOEt, dried over MgSO$_4$, filtered and concentrated under RP. The product is purified by flash chromatography on silica gel (15-40 µm), eluting with a mixture of DCM and methanol (92.5/7.5 by vol.). This gives 6 mg of 5-(2,6-difluorophenyl)-3-{[1-(methylsulphonyl)piperidin-4-yl]amino}-7-ethynyl-2H-pyrazolo[4,3-c]isoquinoline (yellow solid). MS (E/1); m/z=481 (M+); $^1$H NMR: 1.66 (m, 2 H) 2.11 (m, 2 H) 2.87 (s, 3 H) 2.91 (m, 2 H) 3.56 (m, 2 H) 3.79 (m, 1 H) 4.37 (s, 1 H) 6.10 (d, J=8.3 Hz, 1 H) 7.34 (t, J=7.9 Hz, 2 H) 7.65 (broad s, 1 H) 7.69 (m, 1 H) 7.97 (broad d, J=8.3 Hz, 1 H) 8.42 (d, J=8.3 Hz, 1 H) 12.88 (broad s, 1 H).

Example 8

Methyl 5-(2,6-difluorophenyl)-3-{[1-(methylsulphonyl)piperidin-4-yl]amino}-1H-pyrazolo[4,3-c]isoquinoline-7-carboxylate Step 1: A 250 ml three-necked flask equipped with a magnetic stirrer and an argon intake is charged with 4 g of 5-(2,6-difluorophenyl)-7-iodo-1H-pyrazolo[4,3-c]isoquinoline, prepared in step 6 of example 1, in 120 ml of THF and 3 ml of DMF. The mixture is cooled to 0° C. using an ice bath and then 952 mg of sodium hydride (60%) are added. After 15 min at 0° C., 1.3 ml of dimethylsulphamoyl chloride are added. After 16 h at RT, the mixture is poured into 300 ml of water and extracted with ethyl acetate. The organic phase is dried over MgSO$_4$, filtered and concentrated under RP. The solid obtained is triturated in diisopropyl ether. The insoluble material is filtered off under RP and dried under vacuum to give 2.94 g of 5-(2,6-difluorophenyl)-7-iodo-N,N-dimethyl-1H-pyrazolo[4,3-c]isoquinoline-1-sulphonamide (beige solid). LC-MS-DAD-ELSD: 515(+)=(M+H)(+).

Step 2: A 250 ml round-bottomed flask equipped with a magnetic stirrer and with a septum having a top-mounted argon intake is charged with 2.94 g of 5-(2,6-difluorophenyl)-7-iodo-N,N-dimethyl-1H-pyrazolo[4,3-c]isoquinoline-1-sulphonamide in 90 ml of DMF. After argon has been bubbled through for 10 min, 1.81 g of tributylvinylstannane and 331 mg of triphenylphosphine palladium(0) are added. The mixture is heated at reflux for 3 h and then, after cooling, the mixture is poured into water and extracted with ethyl acetate. The organic phase is dried over MgSO$_4$ and evaporated to dryness under RP. This gives 2.36 g of 5-(2,6-difluorophenyl)-7-ethenyl-N,N-dimethyl-1H-pyrazolo[4,3-c]isoquinoline-1-sulphonamide (brown solid). The product is used as it is. LC-MS-DAD-ELSD: 415 (+)=(M+H)(+).

Step 3: A 250 ml round-bottomed flask equipped with a magnetic stirrer and with a septum having a top-mounted argon intake is charged with 2.36 g of 5-(2,6-difluorophenyl)-7-ethenyl-N,N-dimethyl-1H-pyrazolo[4,3-c]isoquinoline-1-sulphonamide in 30 ml of THF and then 23 ml of water, 30 ml of tort-butanol, 2.14 ml of a solution of osmium tetroxide at 2.5% in 2-methyl-2-propanol, and 5.04 g of sodium periodate are added. The mixture is stirred at RT for 4 h and then poured into 100 ml of water and extracted with AcOEt. The organic phase is washed with saturated NaCl solution, dried over MgSO$_4$, filtered and concentrated under RP. The crude product is purified by chromatography on silica gel (15-40 µm), eluting with DCM, to give 1.92 g of 5-(2,6-difluorophenyl)-7-formyl-N,N-dimethyl-1H-pyrazolo[4,3-c]isoquinoline-1-sulphonamide (beige solid). LC-MS-DAD-ELSD: 417 (+)=(M+H)(+).

Step 4: A 250 ml round-bottomed flask is charged with 1.41 g of 5-(2,6-difluorophenyl)-7-formyl-N,N-dimethyl-1H-pyrazolo[4,3-c]isoquinoline-1-sulphonamide in 124 ml of acetone. 1.07 g of potassium permanganate in solution in 62 ml of water are added. After 1 h at RT, the acetone is evaporated and then the mixture is acidified to a pH of 1 by addition of 5N hydrochloric acid. The mixture is extracted with ethyl acetate and the organic phase is washed with saturated NaCl solution, dried over MgSO$_4$, filtered and concentrated under RP to give 1.46 g of 5-(2,6-difluorophenyl)-1-(dimethylsulphamoyl)-1H-pyrazolo[4,3-c]isoquinoline-7-carboxylic acid (yellow solid). LC-MS-DAD-ELSD: 433 (+)=(M+H) (+).

Step 5: A 250 ml round-bottomed flask is charged with 1.46 g of 5-(2,6-difluorophenyl)-1-(dimethylsulphamoyl)-1H-pyrazolo[4,3-c]isoquinoline-7-carboxylic acid in 100 ml of DCM and then 20 ml of TFA are added. The mixture is stirred at RT for 16 h. It is concentrated under RP and the solid obtained is taken up in 30 ml of saturated aqueous NaHCO$_3$ solution and extracted with three times 30 ml of AcOEt. The aqueous phase is acidified to a pH of 1 by addition of 37% HCl and extracted with AcOEt. The organic phase is washed with saturated NaCl solution, dried over MgSO$_4$, filtered and concentrated under RP to give 927 mg of 5-(2,6-difluorophenyl)-2H-pyrazolo[4,3-c]isoquinoline-7-carboxylic acid (beige solid), LC-MS-DAD-ELSD: 326(+)=(M+H)(+).

Step 6: A 100 ml round-bottomed flask is charged with 605 mg of 5-(2,6-difluorophenyl)-2H-pyrazolo[4,3-c]isoquinoline-7-carboxylic acid in 20 ml of DMF. 334 mg of potassium hydroxide and then 595 mg of bromine are added and the mixture is stirred at RT for 1 h. It is poured into 100 ml of water and extracted with ethyl acetate. The organic phase is washed with saturated NaCl solution, dried over MgSO$_4$, filtered and concentrated under RP to give 1.2 g of an orange oil, which is purified by flash chromatography on silica gel (15-40 µm), eluting with a mixture of DCM/methanol (80/20 by vol.) to give 562 mg of 3-bromo-5-(2,6-difluorophenyl)-2H-pyrazolo[4,3-c]isoquinoline-7-carboxylic acid (white solid). LC-MS-DAD-ELSD: 406(+)=(M+H)(+).

Step 7: A 25 ml three-necked flask equipped with a magnetic stirrer and an argon intake is charged with 562 mg of 3-bromo-5-(2,6-difluorophenyl)-2H-pyrazolo[4,3-c]isoquinoline-7-carboxylic acid in 11 ml of DMF, 1.38 ml of diisopropylethylamine and 740 µl of 2-(trimethylsilyl)ethoxymethyl chloride. After 2 h at RT, the reaction mixture is poured into 100 ml of water. The aqueous phase is extracted with 3 times 100 ml of AcOEt and the organic extracts are combined, washed with saturated NaCl solution, dried over MgSO$_4$ and concentrated under RP. The crude product is purified by flash chromatography on silica gel (15-40 µm), eluting with a cyclohexane/DCM mixture (50/50 by vol.) and then with DCM, to give 502 mg of a mixture of 3-bromo-5-(2,6-difluorophenyl)-2-{[2-(trimethylsilyl)ethoxy]methyl}-2H-pyrazolo[4,3-c]isoquinoline-7-carboxylic acid and 3-bromo-5'(2.6° difluorophenyl)-1-{[2-(trimethylsilyl)ethoxy]methyl}-1H-pyrazolo[4,3-c]isoquinoline-7-carboxylic acid (pale yellow oil). LC-MS-DAD-ELSD: 665 (+)=(M+H)(+).

Step 8: A 25 ml round-bottomed flask equipped with a magnetic stirrer is charged with 500 mg of the mixture of 3-bromo-5-(2,6-difluorophenyl)-2-{[2-(trimethylsilyl)ethoxy]methyl}-2H-pyrazolo[4,3-c]isoquinoline-7-carboxylic acid and 3-bromo-5-(2,6-difluorophenyl)-1-{[2-(trimethylsilyl)ethoxy]-methyl}-1H-pyrazolo[4,3-c]isoquinoline-7-carboxylic acid obtained in step 7 in 10 ml of methanol and 1 ml of 2N sodium hydroxide solution. After 5 min at RT, the mixture is poured into 10 ml of AcOEt and 5 ml of water. The organic phase is washed with saturated aqueous NaCl solution, dried over MgSO$_4$ and concentrated under RP to give 336 mg of a mixture of methyl 3-bromo-5'(2,6-difluorophenyl)-1-{[2-(trimethylsilyl)ethoxy]methyl}-1H-pyrazolo[4,3-c]isoquinoline-7-carboxylate and methyl 3-bromo-5-(2,6-difluorophenyl)-2-{[2-(trimethylsilyl)ethoxy]methyl}-2H-pyrazolo[4,3-c]-isoquinoline-7-carboxylate (beige solid). LC-MS-DAD-ELSD: 549 (+)=(M+H)(+).

Step 9: A 25 ml three-necked flask equipped with a magnetic stirrer and with an argon intake is charged with 113 mg of the mixture of methyl 3-bromo-5-(2,6-difluorophenyl)-1-{[2-(trimethylsilyl)ethoxy]methyl}-1H-pyrazolo[4,3-c]isoquinoline-7-carboxylate and methyl 3-bromo-5-(2,6-difluorophenyl)-2-{[2-(trimethylsilyl)ethoxy]methyl}-2H-pyrazolo[4,3-c]isoquinoline-7-carboxylate obtained in step 8 in 3 ml of 1,4-dioxane. After argon has been bubbled through the mixture for 10 min, 37 mg of 1-methanesulphonylpiperidin-4-ylamine, 255 mg of caesium carbonate, 18 mg of 9,9-dimethyl-4,5-bis(diphenylphosphino)xanthene and 5 mg of palladium(II) acetate are added. The mixture is heated at 110° C. for 4 h. After cooling, the mixture is poured into water and extracted with AcOEt. The organic phase is washed with saturated NaCl solution, dried over MgSO$_4$, filtered and concentrated under RP. The product is purified by flash chromatography on silica gel (15-40 µm), eluting with DCM and then with a mixture of DCM and AcOEt (80/20 by vol.) to give 46 mg of a mixture of methyl 5-(2,6-difluorophenyl)-3-{[1-(methylsulphonyl)piperidin-4-yl]amino}-1-{[2-(trimethylsilyl)ethoxy]methyl}-1H-pyrazolo[4,3-c]isoquinoline-7-carboxylate and methyl 5-(2,6-difluorophenyl)-3-{[1-(methylsulphonyl)piperidin-4-yl]amino}-2-{[2-(trimethylsilyl)ethoxy]methyl}-2H-pyrazolo[4,3-c]isoquinoline-7-carboxylate (yellow solid). LC-MS-DAD-ELSD: 646 (+)=(M+H)(+).

Step 10: A 25 ml round-bottomed flask equipped with a magnetic stirrer is charged with 46 mg of the mixture of methyl 5-(2,6-difluorophenyl)-3-{[1-(methylsulphonyl)piperidin-4-yl]amino}-1-{[2-(trimethylsilyl)ethoxy]methyl}-1H-pyrazolo[4,3-c]isoquinoline-7-carboxylate and methyl 5-(2,6-difluorophenyl)-3-{[1-(methylsulphonyl)piperidin-4-yl]amino}-2-{[2-(trimethylsilyl)ethoxy]methyl}-2H-pyrazolo[4,3-c]isoquinoline-7-carboxylate obtained in step 9 in 5 ml of DCM. After cooling to 0° C. using an ice bath, 0.5 ml of TFA are added and the mixture is stirred at RT for 18 h. It is concentrated under RP and the solid obtained is taken up in 20 ml of water and extracted with three times 20 ml of AcOEt. The organic phase is dried over MgSO$_4$, filtered and concentrated under RP. The product is purified by flash chromatography on silica gel (15-40 µm), eluting with DCM and then with a mixture of DCM/AcOEt (50/50 by vol.), to give 12 mg of methyl 5-(2,6-difluorophenyl)-3-{[1-(methylsulphonyl)piperidin-4-yl]amino}-1H-pyrazolo[4,3-c]isoquinoline-7-carboxylate (yellow solid). $^1$H NMR (400 MHz, DMSO-d6) δ ppm 1.67 (m, 2 H) 2.11 (m, 2 H) 2.88 (s, 3 H) 2.92 (m, 2 H) 3.56 (m, 2 H) 3.80 (m, 1 H) 3.87 (s, 3 H) 6.16 (d, J=7.7 Hz, 1 H) 7.37 (m, 2 H) 7.71 (m, 1 H) 8.23 (broad s, 1 H) 8.42 (broad d, J=8.5 Hz, 1 H) 8.54 (d, J=8.5 Hz, 1 H) 13.01 (s, 1 H). LC-MS-DAD-ELSD: 516 (+)=(M+H)(+).

Example 9

5-(2,6-difluorophenyl)-3-{[1-(methylsulphonyl)piperidin-4-yl]amino}-1H-pyrazolo[4,3-c]isoquinoline-7-carbothioamide A microwave tube with a 5 ml capacity is charged with 45 mg of 5-(2,6-difluorophenyl)-3-{[1-(methylsulphonyl)piperidin-4-yl]amino}-1H-pyrazolo[4,3-c]isoquinoline-7-carbonitrile, prepared in example 12, and 0.2 ml of a 20% aqueous solution of ammonium sulphide in 2 ml of methanol. The mixture is microwave-heated at 100° C. for 20 min (power set at 100 watts) and then poured into 50 ml of water and extracted with AcOEt. The organic phase is washed with saturated NaCl solution, dried over MgSO$_4$, filtered and concentrated under RP. The solid obtained is triturated in diisopropyl ether. The insolubles are filtered off under RP and dried under vacuum to give 36 mg of 5-(2,6-difluorophenyl)-

3-{[1-(methylsulphonyl)piperidin-4-yl]amino}-1H-pyrazolo[4,3-c]isoquinoline-7-carbothioamide (yellow solid). $^1$H NMR (400 MHz, DMSO-d6) δ ppm: 1.66 (m, 2 H) 2.11 (m, 2 H) 2.88 (s, 3 H) 2.90 (m, 2 H) 3.56 (m, 2 H) 3.79 (m, 1H) 6.10 (d, J=8.3 Hz, 1 H) 7.33 (t, J=7.8 Hz, 2 H) 7.68 (m, 1 H) 8.18 (broad s, 1 H) 8.34 (dd, J=8.3, 1.5 Hz, 1 H) 8.40 (d, J=8.3 Hz, 1 H) 9.74 (broad s, 1 H) 10.01 (broad s, 1 H) 12.87 (broad m, 1 H) LC-MS-DAD-ELSD: 517 (+)=(M+H)(+).

Example 10

5-(2,6-difluorophenyl)-3-{[1-(methylsulphonyl)piperidin-4-yl]amino}-1H-pyrazolo[4,3-c]isoquinoline Step 1: A 250 ml round-bottomed flask equipped with a magnetic stirrer is charged with 30 g of 2-chloroacetophenone and 36.3 g of potassium phthalimide in 120 ml of DMF. After 4 h at RT, the mixture is concentrated under vacuum. The solid obtained is taken up in 120 ml of DCM and 100 ml of 1 sodium hydroxide solution. The organic phase is washed with saturated aqueous NaCl solution, dried over MgSO$_4$, filtered and concentrated under vacuum. The solid obtained is triturated in diisopropyl ether. The insolubles are filtered off and dried under vacuum to give 42.6 g of 2-(2-oxo-2-phenylethyl)-1H-isoindole-1,3(2H)-dione in the form of a beige solid, which is used as it is in the following step.

Step 2: A 100 ml round-bottomed flask equipped with a magnetic stirrer is charged with 42.4 g of 2-(2-oxo-2-phenylethyl)-1H-isoindole-1,3(2H)dione in 105 ml of N,N-dimethylformamide diethyl acetal. The mixture is heated at reflux for 3 h and then concentrated under RP. The product is purified by flash chromatography on silica gel (15-40 μm), eluting with DCM and then with a mixture of DCM and methanol (90/10 by vol.), to give 40.69 g of a mixture of the E and Z isomers of 2-[1-(dimethylamino)-3-oxo-3-phenylprop-1-en-2-yl]-1H-isoindole-1,3(2H)dione in the form of a cream solid. LC-MS-DAD-ELSD: 321 (+)=(M+H)(+).

Step 3: A 250 ml round-bottomed flask is charged at RT with 20.5 g of a mixture of the E and Z isomers of 2-[1-(dimethylamino)-3-oxo-3-phenylprop-1-en-2-yl]-1H-isoindole-1,3(2H)dione in 75 ml of ethanol. 7.8 ml of hydrazine hydrate are added. The suspension is stirred at RT for 1 h 30 min and then heated to reflux. After 1 h 30 min of heating, a thickening of the mixture may be observed, and it takes on a yellow colour. The suspension is filtered off hot with suction on a frit and the precipitate is washed with ethanol. The filtrate is concentrated under RP. The product is purified by flash chromatography on silica gel (15-40 μm), eluting with DCM and with a DCM/methanol mixture (95/5 by vol.), to give 9.45 g of 5-phenyl-1H-pyrazol-4-amine (brown solid). LC-MS-DAD-ELSD: 163 (+)=(M+H)(+).

Step 4: A 250 ml round-bottomed flask equipped with a magnetic stirrer is charged with 10 g of 5-phenyl-1H-pyrazol-4-ylamine in 45 ml of DCM and 45 ml of pyridine. The reaction mixture is cooled to 0° C. using an ice bath, and 17.4 ml of 2,6-difluorobenzoic chloride are added. The mixture is stirred at RT for 3 h. After evaporation of the solvent under RP, 50 ml of water are added to the crude reaction product, and then the aqueous phase is extracted with two times 50 ml of AcOEt. The organic extracts are combined, washed with saturated NaCl solution and dried over MgSO$_4$. The AcOEt is then evaporated under vacuum to give a mixture of 2,6-difluoro-N-[5-phenyl-1H-pyrazol-4-yl]benzamide and N-[1-(2,6-difluorobenzoyl)-5-phenyl-1H-pyrazol-4-yl]-2,6-difluorobenzamide in the form of a brown oil. The crude reaction product is treated to give solely the expected product: in a 250 ml round-bottomed flask, the mixture of 2,6-difluoro-N-[5-phenyl-1H-pyrazol-4-yl]benzamide and N-[1-(2,6-difluorobenzoyl)-5-phenyl-1H-pyrazol-4-yl]-2,6-difluorobenzamide is dissolved, at RT and under argon, in 20 ml of methanol and 20 ml of 5N aqueous sodium hydroxide solution. After 30 min at RT, the mixture is poured into 50 ml of water and extracted with AcOEt and the organic phases are washed with saturated NaCl solution, dried over MgSO$_4$ and then concentrated under RP. This gives a crude product, which is suspended in DCM and stirred at the reflux of the DCM for 15 min. After cooling using an ice bath, the precipitate is filtered off with suction on a frit and washed twice with ice-cold DCM. This gives 7.7 g of 2,6-difluoro-N-(5-phenyl-1H-pyrazol-4-yl)benzamide (ochre solid). LC-MS-DAD-ELSD: 300 (+)=(M+H)(+).

Step 5: A 500 ml three-neck flask equipped with a magnetic stirrer and with an argon intake is charged with 12.5 g of 2,6-difluoro-N'(5-phenyl-1H-pyrazol-4-yl)benzamide, 218 ml of phosphorus oxychloride and 68.2 g of P$_2$O$_5$. After 30 min at reflux, the mixture solidifies. 20 ml of phosphorus oxychloride are added. After 5 h of reflux, the reaction mixture is cooled to RT and then poured slowly into 2 l of ice-water, with the temperature maintained at below 40° C. Neutralization is carried out by slow addition of potassium carbonate, and extraction takes place 3 times with 500 ml of AcOEt. The organic extracts are combined, washed with saturated NaCl solution and dried over MgSO$_4$, and then concentrated under RP. The solid obtained is purified by flash chromatography on silica gel (15-40 μm), eluting with DCM and with a DCM/AcOEt mixture (80/20 by vol.). This gives 6.4 g of 5-(2,6-difluorophenyl)-1H-pyrazolo[4,3-c]isoquinoline (yellow foam). LC-MS-DAD-ELSD: 282 (+)=(M+H)(+).

Step 6: A 50 ml round-bottomed flask equipped with a magnetic stirrer and with a septum having a top-mounted argon intake is charged with 700 mg of 5-(2,6-difluorophenyl)-1H-pyrazolo[4,3-c]isoquinoline in 25 ml of DMF. 447 mg of KOH and then 0.26 ml of bromine 447 mg of KOH are added. After 1 h at RT, the mixture is poured into 100 ml of ice-water. The aqueous phase is extracted with 3 times 100 ml of AcOEt. The organic extracts are combined, washed with saturated NaCl solution and dried over MgSO$_4$, and evaporated under RP. This gives 950 mg of 3-bromo-5-(2,6-difluorophenyl)-1H-pyrazolo[4,3-c]isoquinoline (orange solid). The product will be used as it is in the following step. LC-MS-DAD-ELSD: 362 (+)=(M+H)(+).

Step 7: A 50 ml round-bottomed flask equipped with a magnetic stirrer and with a septum having a top-mounted argon intake is charged with 890 mg of 3-bromo-5-(2,6-difluorophenyl)-1H-pyrazolo[4,3-c]isoquinoline in 20 ml of DMF, 2.46 ml of N,N-diisopropylethylamine and 658 μl of 2-(trimethylsilyl)ethoxymethyl chloride. After 16 h at RT, the mixture is poured into 50 ml of ice-water. The aqueous phase is extracted with 3 times 50 ml of AcOEt and the organic extracts are combined, washed with saturated NaCl solution, dried over MgSO$_4$ and concentrated under RP. The product is purified by flash chromatography on silica gel (15-40 μm), eluting with a mixture of cyclohexane and DCM (80/20 by vol.) then (50/50 by vol.), to give on one hand 498 mg of 3-bromo-5-(2,6-difluorophenyl)-1-{[2-(trimethylsilyl)ethoxy]methyl}-1H-pyrazolo[4,3-c]isoquinoline, in the form of a white gum, LC-MS-DAD-ELSD: 492 (+)=(M+H)(+), and on the other hand 200 mg of 3-bromo-5-(2,6-difluorophenyl)-2-{[2-(trimethylsilyl)ethoxy]methyl}-2H-pyrazolo[4,3-c]isoquinoline (white gum), LC-MS-DAD-ELSD: 492 (+)=(M+H)(+).

Step 8: A 25 ml three-necked flask equipped with a magnetic stirrer and with an argon intake is charged with 200 mg of 3-bromo-5-(2,6-difluorophenyl)-1-{[2-(trimethylsilyl)

ethoxy]methyl}-1H-pyrazolo[4,3-c]isoquinoline in 6 ml of 1,4-dioxane. After argon has been bubbled through the reaction mixture for 10 min, 73 mg of 1-methylsulphonylpiperidin-4-ylamine, 505 mg of caesium carbonate, 36 mg of 9,9-dimethyl-4,5-bis(diphenylphosphino)xanthene and 10 mg of palladium(II) acetate are added. The mixture is heated at 120° C. for 2 h. After cooling, the mixture is poured into water and extracted with AcOEt. The organic phase is washed with saturated NaCl solution, dried over MgSO$_4$, filtered and concentrated under RP. The product is purified by flash chromatography on silica gel (15-40 μm), eluting with a mixture of cyclohexane and AcOEt (50/50 by vol.), to give 71 mg of 5-(2,6-difluorophenyl)-3-{[1-(ethylsulphonyl)piperidin-4-yl]amino}-1-{[2-(trimethylsilyl)ethoxy]methyl}-1H-pyrazolo[4,3-c]isoquinoline (yellow gum). LC-MS-DAD-ELSD: 588 (+)=(M+H)(+).

Step 9: A 10 ml round-bottomed flask is charged with 71 mg of 5-(2,6-difluorophenyl)-3-{[1-(methylsulphonyl)piperidin-4-yl]amino}-1-{[2-(trimethylsilyl)ethoxy]methyl}-1H-pyrazolo[4,3-c]isoquinoline in 3 ml of DCM. After cooling to 0° C. using an ice bath, 0.3 ml of TFA is added and the reaction mixture is stirred at RT for 16 h. It is concentrated under RP and the solid obtained is taken up in 20 ml of water and extracted with three times 20 ml of AcOEt. The organic phase is dried over MgSO$_4$, filtered and concentrated under RP. The product is purified by flash chromatography on silica gel (15-40 μm), eluting with DCM and with a mixture of DCM and methanol (95/5 by vol.), to give 9 mg of 5-(2,6-difluorophenyl)-3-{[1-(methylsulphonyl)piperidin-4-yl]amino}-1H-pyrazolo[4,3-c]isoquinoline (beige solid). $^1$H NMR (400 MHz, DMSO-d6) δ ppm 1.67 (m, 2 H) 2.11 (m, 2 H) 2.88 (s, 3 H) 2.90 (m, 2 H) 3.56 (m, 2 H) 3.79 (broad s, 1 H) 6.04 (broad m, 1 H) 7.32 (m, 2 H) 7.52-7.74 (m, 3 H) 7.92 (m, 1 H) 8.40 (d, 1 H) 12.76 (broad s, 1 H); LC-MS-DAD-ELSD: 458 (+)=(M+H)(+).

Example 11

5-(2,6-difluorophenyl)-3-{[1-(cyclopropylsulphonyl)piperidin-4-yl]amino}-1H-pyrazolo[4,3-c]isoquinoline-7-carbonitrile Step 1: A 25 ml three-necked flask equipped with a magnetic stirrer and with an argon intake is charged with 150 mg of 3-bromo-5-(2,6-difluorophenyl)-1-{[2-(trimethylsilyl)ethoxy]methyl}-1H-pyrazolo[4,3-c]isoquinoline-7-carbonitrile, prepared in step 11 of example 1, in 4 ml of 1,4-dioxane. After argon has been bubbled through the mixture for 10 min, 60 mg of 1-cyclopropylsulphonylpiperidin-4-ylamine, 361 mg of caesium carbonate, 25 mg of 9,9-dimethyl-4,5-bis(diphenylphosphino)xanthene and 7 mg of palladium(II) acetate are added. The mixture is heated at 120° C. for 2 h. After cooling, the mixture is poured into water and extracted with AcOEt. The organic phase is washed with saturated NaCl solution, dried over MgSO$_4$, filtered and concentrated under RP. The product is purified by flash chromatography on silica gel (15-40 μm), eluting with a mixture of cyclohexane and AcOEt (50/50 by vol.), to give 57 mg of 5-(2,6-difluorophenyl)-3-{[1-(cyclopropylsulphonyl)piperidin-4-yl]amino}-1-{[2-(trimethylsilyl)ethoxy]methyl}-1H-pyrazolo[4,3-c]isoquinoline-7-carbonitrile (yellow solid). LC-MS-DAD-ELSD: 639 (+)=(M+H)(+).

Step 2: A 10 ml round-bottomed flask equipped with a magnetic stirrer is charged with 57 mg of 5-(2,6-difluorophenyl)-3-{[1-(cyclopropylsulphonyl)piperidin-4-yl]amino}-1-{[2-(trimethylsilyl)ethoxy]methyl}-1H-pyrazolo[4,3-c]isoquinoline-7-carbonitrile in 5 ml of DCM. After cooling to 0° C. using an ice bath, 0.3 ml of TFA is added and the mixture is stirred at RT for 3 h. It is concentrated under RP and the solid obtained is taken up in 20 ml of water and extracted with three times 20 ml of AcOEt, dried over MgSO$_4$, filtered and concentrated under RP. The product is purified by flash chromatography on silica gel (15-40 μm), eluting with a mixture of cyclohexane and AcOEt (80/20 by vol.), to give 16 mg of 5-(2,6-difluorophenyl)-3-{[1-(cyclopropylsulphonyl)piperidin-4-yl]amino}-1H-pyrazolo[4,3-c]isoquinoline-7-carbonitrile (yellow solid). $^1$H NMR (400 MHz, DMSO-d6) δ ppm 0.89-1.04 (m, 4 H) 1.67 (m, 2 H) 2.10 (m, 2 H) 2.58 (m, 1 H) 3.00 (m, 2 H) 3.62 (m, 2 H) 3.82 (m, 1 H) 6.21 (d, J=7.8 Hz, 1 H) 7.34 (t, J=7.8 Hz, 2 H) 7.70 (m, 1 H), 8.19 (broad s, 1 H) 8.27 (dd, J=8.5, 1.5 Hz, 1 H) 8.56 (d, J=8.5 Hz, 1 H) 13.07 (s, 1 H) LC-MS-DAD-ELSD: 509 (+)=(M+H)(+).

Example 12

5-(2,6-difluorophenyl)-3-{[1-(methylsulphonyl)piperidin-4-yl]amino}-1H-pyrazolo[4,3-c]isoquinoline-7-carbonitrile Step 1: A 25 ml three-necked flask equipped with a magnetic stirrer and an argon intake is charged with 525 mg of 3-bromo-5-(2,6-difluorophenyl)-1-{[2-(trimethylsilyl)ethoxy]methyl}-1H-pyrazolo[4,3-c]isoquinoline-7-carbonitrile, prepared in step 11 of example 1, in 12 ml of 1,4-dioxane. After argon has been bubbled through the reaction mixture for 10 min, 294 mg of 1-methylsulphonylpiperidin-4-ylamine, 1.26 g of caesium carbonate, 89 mg of 9,9-dimethyl-4,5-bis(diphenylphosphino)xanthene and 23 mg of palladium(II) acetate are added. The reaction mixture is heated at 120° C. for 2 h. After cooling, the mixture is poured into water and extracted with AcOEt. The organic phase is washed with saturated NaCl solution, dried over MgSO$_4$, filtered and concentrated under RP. The product is purified by flash chromatography on silica gel (15-40 μm), eluting with a cyclohexane/AcOEt mixture (80/20 by vol.) then (50/50 by vol.), to give 470 mg of 5-(2,6-difluorophenyl)-3-{[1-(ethylsulphonyl)piperidin-4-yl]amino}-1-{[2-(trimethylsilyl)ethoxy]methyl}-1H-pyrazolo[4,3-c]isoquinoline-7-carbonitrile (yellow solid). LC-MS-DAD-ELSD: 613 (+)=(M+H)(+).

Step 2: A microwave tube of maximum capacity 20 ml, equipped with a magnetic stirrer, is charged with 300 mg of 5-(2,6-difluorophenyl)-3-{[1-(methylsulphonyl)piperidin-4-yl]amino}-1-({2-(trimethylsilyl)ethoxy]methyl}-1H-pyrazolo[4,3-c]isoquinoline-7-carbonitrile in 12 ml of 5N hydrochloric acid. The reaction mixture is microwave-heated at 100° C. for 5 min and then poured into 20 ml of water, brought to a pH of 7 by addition of 9.3N sodium hydroxide solution, and extracted with three times 20 ml of AcOEt. The combined organic phases are dried over MgSO$_4$, filtered and concentrated under RP. The product is purified by flash chromatography on silica gel (15-40 μm), eluting with a mixture of DCM and AcOEt (50/50 by vol.), to give 130 mg of 5-(2,6-difluorophenyl)-3-{[1-(methylsulphonyl)piperidin-4-yl]amino}-1H-pyrazolo[4,3-c]isoquinoline-7-carbonitrile (yellow solid). $^1$H NMR (400 MHz, DMSO-d6) 1.67 (m, 2 H) 2.11 (m, 2 H) 2.87 (s, 3 H) 2.90 (m, 2 H) 3.56 (m, 2 H) 3.80 (m, 1 H) 6.20 (broad d, J=7.7 Hz, 1 H) 7.34 (m, 2 H) 7.70 (m, 1 H) 8.18 (broad s, 1 H) 8.28 (broad d, J=8.6 Hz, 1 H) 8.56 (d, J=8.6 Hz, 1 H) 13.07 (s, 1H) LC-MS-DAD-ELSD: 483 (+)=(M+H)(+).

Example 13

5-(2,6-difluorophenyl)-3-([1-(ethylsulphonyl)piperidin-4-yl]amino}-1H-pyrazolo[4,3-c]isoquinoline-7-carbonitrile Step 1: A 25 ml three-necked flask equipped with a magnetic stirrer and an argon intake is charged with 150 mg of 3-bromo-5-(2,6-difluorophenyl)-1-{[2-(trimethylsilyl)ethoxy]methyl}-1H-pyrazolo[4,3-c]isoquinoline-7-carbonitrile, prepared in step 11 of example 1, in 4 ml of 1,4-dioxane. After argon has been bubbled through the reaction mixture for 10 min, 56 mg of 1-ethylsulphonylpiperidin-4-ylamine, 361 mg of caesium carbonate, 25 mg of 9,9-dimethyl-4,5-bis (diphenylphosphino)xanthene and 7 mg of palladium(II) acetate are added. The mixture is heated at 120° C. for 2 h. After cooling, the mixture is poured into water and extracted with AcOEt. The organic phase is washed with saturated NaCl solution, dried over $MgSO_4$, filtered and concentrated under RP. The product is purified by flash chromatography on silica gel (15-40 µm), eluting with a cyclohexane/AcOEt mixture (80/20 by vol.) then (50/50 by vol.), to give 60 mg of 5-(2,6-difluorophenyl)-3-{[1-(ethylsulphonyl)piperidin-4-yl]amino}-1-{[2-(trimethylsilyl)ethoxy]methyl}-1H-pyrazolo[4,3-c]isoquinoline-7-carbonitrile (yellow solid). LC-MS-DAD-ELSD: 627 (+)=(M+H)(+).

Step 2: A 10 ml round-bottomed flask equipped with a magnetic stirrer is charged with 50 mg of 5-(2,6-difluorophenyl)-3-{[1-(ethylsulphonyl)piperidin-4-yl]amino}-1-{[2-(trimethylsilyl)ethoxy]methyl}-1H-pyrazolo[4,3-c]isoquinoline-7-carbonitrile in 5 ml of DCM. After cooling to 0° C. using an ice bath, 0.1 ml of TFA is added and the mixture is stirred at RT for 3 h. It is concentrated under RP and the solid obtained is taken up in 20 ml of water and extracted with three times 20 ml of AcOEt. The combined organic phases are dried over $MgSO_4$, filtered and concentrated under RP. The product is purified by flash chromatography on silica gel (15-40 µm), eluting with DCM and with a mixture of DCM and methanol (90/10 by vol.), to give 27 mg of 5-(2,6-difluorophenyl)-3-{[1-(ethylsulphonyl)piperidin-4-yl]amino}-1H-pyrazolo[4,3-c]isoquinoline-7-carbonitrile (yellow solid). $^1$H NMR (400 MHz, DMSO-d6) 1.23 (t, J=7.3 Hz, 3 H) 1.63 (m, 2 H) 2.09 (m, 2 H) 2.97 (m, 2 H) 3.05 (q, J=7.3 Hz, 2 H) 3.61 (m, 2 H) 3.81 (m, 1 H) 6.23 (broad m, 1 H) 7.34 (t, J=7.8 Hz, 2 H) 7.70 (m, 1 H) 8.18 (broad s, 1 H) 8.27 (broad d, J=8.5 Hz, 1 H) 8.56 (d, J=8.5 Hz, 1 H) 13.07 (broad s, 1 H) LC-MS-DAD-ELSD: 497 (+)=(M+H)(+).

Example 14

5-(2,6-difluorophenyl)-3-{[1-(cyclopropylsulphonyl)piperidin-4-yl]amino}-1H-pyrazolo[4,3-c]isoquinoline-7-carboxamide A 10 ml round-bottomed flask is charged with 29.7 mg of 5-(2,6-difluorophenyl)-3-{[1' (cyclopropylsulphonyl)piperidin-4-yl]amino}-1H-pyrazolo[4,3-c]isoquinoline-7-carbonitrile, prepared in example 11, 1.3 ml of ethanol and 125 µL of 9.3N sodium hydroxide. After 30 min at reflux, the mixture is concentrated under RP and the solid obtained is taken up in 10 ml of water and extracted with three times 10 ml of AcOEt. The combined organic phases are dried over $MgSO_4$, filtered and concentrated under RP to give 17 mg of 5-(2,6-difluorophenyl)-3-{[1-(cyclopropylsulphonyl)piperidin-4-yl]amino}-1H-pyrazolo[4,3-c]isoquinoline-7-carboxamide (yellow solid). $^1$H NMR (400 MHz, DMSO-d6) δ ppm 0.89-1.02 (m, 4 H) 1.67 (m, 2 H) 2.11 (m, 2 H) 2.58 (m, 1 H) 3.00 (m, 2 H) 3.63 (m, 2 H) 3.80 (m, 1 H) 6.09 (d, J=7.3 Hz, 1 H) 7.35 (d, J=7.8 Hz, 2 H) 7.56 (broad s, 1 H) 7.68 (m, 1 H) 817 (broad s, 1 H) 8.23 (broad s, 1 H) 8.35 (broad d, J=8.5 Hz, 1 H) 8.45 (d, J=8.5 Hz, 1 H) 12.87 (s, 1 H) LC-MS-DAD-ELSD: 527 (+)=(M+H)(+).

Example 15

5-(2,6-difluorophenyl)-3-{[1-(methylsulphonyl)piperidin-4-yl]amino}-1H-pyrazolo[4,3-c]isoquinoline-7-carbaldehyde A 10 ml round-bottomed flask is charged with 54 mg of 5-(2,6-difluorophenyl)-3-{[1-(methylsulphonyl)piperidin-4-yl]amino}-1-{[2-(trimethylsilyl)ethoxy]methyl}-1H-pyrazolo[4,3-c]isoquinoline-7-carbaldehyde, prepared in step 5 of example 2, in 5 ml of DCM. After cooling to 0° C. using an ice bath, 0.3 ml of TFA is added and the mixture is stirred at RT for 16 h. It is concentrated under RP and the solid obtained is taken up in 5 ml of saturated aqueous $NaHCO_3$ solution. It is extracted with AcOEt, dried over $MgSO_4$, filtered and concentrated under RP. The product is purified by flash chromatography on silica gel (15-40 µm), eluting with a mixture of DCM/AcOEt (50/50 by vol.). This gives 9 mg of 5-(2,6-difluorophenyl)-3-{[1-(methylsulphonyl)piperidin-4-yl]amino}-1H-pyrazolo[4,3-c]isoquinoline-7-carbaldehyde (yellow solid). $^1$H NMR (400 MHz, DMSO-d6) δ ppm 1.68 (m, 2 H) 2.11 (m, 2 H) 2.88 (s, 3 H) 2.90 (m, 2 H) 3.57 (m, 2 H) 3.81 (m, 1 H) 6.16 (broad m, 1 H) 7.36 (t, J=7.8 Hz, 2 H) 7.71 (m, 1 H) 8.23 (broad s, 1 H) 8.34 (broad d, J=8.5 Hz, 1 H) 8.57 (d, J=8.2 Hz, 1 H) 10.10 (s, 1 H) 13.02 (broad s, 1 H). LC-MS-DAD-ELSD: 486 (+)=(M+H)(+).

Example 16

5-(2,6-difluorophenyl)-N-hydroxy-3-{[1-(methylsulphonyl)piperidin-4-yl]amino}-1H-pyrazolo[4,3-c]isoquinoline-7-carboximidamide A 10 ml round-bottomed flask is charged with 30 mg of 5-(2,6-difluorophenyl)-3-{[1-(methylsulphonyl)piperidin-4-yl]amino}-1H-pyrazolo[4,3-c]isoquinoline-7-carbonitrile, prepared in example 12, 1.3 ml of methanol, 0.8 ml of THF and 62 mg of triethylamine. 44 mg of hydroxylamine as the hydrochloride are added. The mixture is heated at 65° C. for 3 h and then evaporated under RP. The solid obtained is taken up in 10 ml of water and extracted with AcOEt. The organic phase is dried over $MgSO_4$, filtered and concentrated under RP. It is purified by flash chromatography on silica gel (15-40 µm), eluting with DCM and then with a DCM/methanol mixture (80/20 by vol.), to give 9.7 mg of 5-(2,6-difluorophenyl)-N-hydroxy-3-{[1-(methylsulphonyl)piperidin-4-yl]amino}-1H-pyrazolo[4,3-c]isoquinoline-7-carboximidamide in the form of a yellow solid. $^1$H NMR (300 MHz, DMSO-d6) δ ppm 1.67 (m, 2 H) 2.11 (m, 2 H) 2.91 (m, 2 H) 2.87 (s, 3 H) 3.56 (m, 2 H) 3.79 (m, 1 H) 5.95 (broad s, 2 H) 6.03 (d, J=7.9 Hz, 1 H) 7.31 (m, 2 H) 7.66 (m, 1 H) 7.95 (broad s, 1 H) 8.18 (dd, J=8.5, 1,6 Hz, 1H) 8.39 (d, J=8.5 Hz, 1 H) 9.82 (s, 1 H) 12.76 (s, 1H). LC-MS-DAD-ELSD: 516 (+)=(M+H)(+).

Example 17

[5-(2,6-difluorophenyl)-7-(fluoromethyl)-N-[1-(methylsulphonyl)piperidin-4-yl]-1H-pyrazolo[4,3-c]isoquinolin-3-amine Step 1: Starting from 377 mg of [5-(2,6-difluorophenyl)-3-{[1-(methylsulphonyl)piperidin-4-yl]amino}-1-{[2-(trimethylsilyl)ethoxy]methyl}-1H-pyrazolo[4,3-c]isoquinolin-7-yl]methanol, prepared in step 1 of example 3, and 7 ml of DCM. The mixture is cooled to −70° C. using a dry-ice bath and admixed with 88 μL of diethylaminosulphur trifluoride (DAST). After 30 min the mixture is poured into saturated aqueous sodium bicarbonate solution, extracted with AcOEt, washed with saturated NaCl solution, dried over MgSO$_4$, filtered and concentrated under RP. The product is purified by flash chromatography on silica gel (40-63 μm), eluting with a DCM/AcOEt mixture (85/15 by vol.), to give 90 mg of [5-(2,6-difluorophenyl)-7-(fluoromethyl)-N-[1-(methylsulphonyl)piperidin-4-yl]-2-{[2-(trimethylsilyl)ethoxy]methyl}-2H-pyrazolo[4,3-c]isoquinolin-3-amine (yellow solid). MS (E/I): m/z=619 (M+); $^1$H NMR: −0.05 (s, 9 H) 0.88 (m, 2 H) 1.60 (m, 2 H) 2.10 (m, 2 H) 2.74 (m, 2 H) 2.84 (s, 3 H) 3.58 (m, 2H) 3.66 (m, 2H) 4.44 (broad m, 1H) 5.58 (d, J=47.4 Hz, 2H) 5.65 (s, 2H) 6.48 (d, J=7.6 Hz, 1H) 7.33 (t, J=7.5 Hz, 2H) 7.52 (broad s, 1H) 7.64 (m, 1H) 7.82 (broad d, J=8.1 Hz, 1H) 8.38 (d, J=8.1 Hz, 1H).

Step 2: A 30 ml round-bottomed flask equipped with a magnetic stirrer and with a septum having a top-mounted argon intake is charged with 87 mg of [5-(2,6-difluorophenyl)-7-(fluoromethyl)-N-[1-(methylsulphonyl)piperidin-4-yl]-2-{[2-(trimethylsilyl)ethoxy]methyl}-2H-pyrazolo[4,3-c]isoquinolin-3-amine in 7 ml of DCM. After cooling to 0° C. using an ice bath, 0.85 ml of TFA is added and the mixture is stirred at RT for 3 h. The mixture is concentrated under RP and the solid obtained is taken up in 24 ml of water and 1.1 ml of 0.75M aqueous ammonia solution. It is extracted with ethyl acetate, dried over MgSO$_4$, filtered and concentrated under RP. The product is purified by flash chromatography on silica gel (15-40 μm), eluting with a DCM/MeOH mixture (95/05 by vol.). This gives 27 mg of [5-(2,6-difluorophenyl)-7-(fluoromethyl)-N-[1-(methylsulphonyl)piperidin-4-yl]-1H-pyrazolo[4,3-c]isoquinolin-3-amine (yellow solid). $^1$H NMR: 1.67 (m, 2 H) 2.11 (m, 2 H) 2.87 (s, 3 H) 2.90 (m, 2 H) 3.56 (m, 2 H) 3.80 (broad m, 1 H) 5.58 (d, J=47.2 Hz, 2 H) 6.05 (broad d, J=8.0 Hz, 1 H) 7.33 (t, J=77 Hz, 2 H) 7.57-7.73 (m, 2 H) 7.95 (broad d, J=8.3 Hz, 1 H) 8.45 (d, J=8.3 Hz, 1 H) 12.81 (s, 1 H).

Example 18

5-(2,6-difluorophenyl)-3-{[1-(ethylsulphonyl)piperidin-4-yl]amino}-1H-pyrazolo[4,3-c]isoquinolin-7-carboxamide Step 1; A 100 ml round-bottomed flask equipped with a magnetic stirrer and with a septum having a top-mounted argon intake is charged with 600 mg of 3-bromo-5-(2,6-difluorophenyl)-1-{[2' (trimethylsilyl)ethoxy]methyl}-1H-pyrazolo[4,3-c]isoquinoline-7-carbonitrile in 15 ml of 1,4-dioxane. After argon has been bubbled through the reaction mixture for 10 min, 448 mg of 1-ethanesulphonylpiperidin-4-ylamine, 1.4 g of caesium carbonate, 80 mg of 9,9-dimethyl-4,5-bis(diphenylphosphino)xanthene and 26 mg of palladium(II) acetate are added. The mixture is heated at reflux for 4 h. After cooling, the mixture is poured into water, extracted with AcOEt, washed with saturated NaCl solution, dried over MgSO$_4$, filtered and concentrated under RP. The product is purified by flash chromatography on silica gel (40-63 μm), eluting with a mixture of DCM and AcOEt (95/05 by vol.), to give 436 mg of 5-(2,6-difluorophenyl)-3-{[1-(ethylsulphonyl)piperidin-4-yl]amino}-1-{[2-(trimethylsilyl)ethoxy]methyl}-1H-pyrazolo[4,3-c]isoquinoline-7-carbonitrile (yellow solid). MS (E/I): m/z=626 (M+); $^1$H NMR: −0.06 (s, 9H); 0.88 (m, 2H); 1.18 (t, J=7.3 Hz, 3H); 1.58 (m, 2H); 2.07 (m, 2H); 2.82 (m, 2H); 3.03 (q, J=7.3 Hz, 2H); 3.56-3.70 (m, 4H); 4.47 (m, 1H); 5.67 (s, 2H); 6.69 (d, J=8.1 Hz, 1H); 7.33 (t, J=7.8 Hz, 2H); 7.66 (m, 1H); 7.96 (d, J=1.7 Hz, 1H); 8.13 (dd, J=8.3 and 1.7 Hz, 1H); 8.47 (d, J=8.3 Hz, 1H).

Step 2: A 100 ml round-bottomed flask equipped with a magnetic stirrer and with a septum having a top-mounted argon intake is charged with 396 mg of 5-(2,6-difluorophenyl)-3-{[1-(ethylsulphonyl)piperidin-4-yl]amino}-1-{[2-(trimethylsilyl)ethoxy]methyl}-1H-pyrazolo[4,3-c]isoquinoline-7-carbonitrile in 4 ml of toluene. After cooling to 0° C. using an ice bath, 0.64 ml of 95% sulphuric acid is added and the mixture is stirred at RT for 15 h. It is cooled to 0° C. and neutralized with 9 ml of 7.5M aqueous NH$_3$ solution. The product is extracted with AcOEt, dried over MgSO$_4$, filtered and concentrated under RP. It is purified by flash chromatography on silica gel (15-40 μm), eluting with a mixture of DCM and MeOH (95/05 by vol.). This gives 174 mg of 5-(2,6-difluorophenyl)-3-{[1-(ethylsulphonyl)piperidin-4-yl]amino}-1H-pyrazolo[4,3-c]isoquinoline-7-carboxamide (yellow solid). MS (E/I): m/z=514 (M+); $^1$H NMR: 1.23 (t, J=7.4 Hz, 3H); 1.65 (m, 2H); 2.09 (m, 2H); 2.98 (m, 2H); 3.05 (q, J=7.4 Hz, 2H); 3.62 (m, 2H); 3.81 (m, 1H); 6.09 (d, J=8.3 Hz, 1H); 7.33 (m, 2H); 7.55 (broad s, 1H); 7.68 (m, 1H); 8.17 (broad s, 1H); 8.23 (broad s, 1H); 8.35 (broad d, J=8.8 Hz, 1H); 8.45 (d, J=8.8 Hz, 1H); 12.85 (s, 1H).

Example 19

5-(2,6-difluorophenyl)-3-{[1-(ethylsulphonyl)piperidin-4-yl]amino}-1H-pyrazolo[4,3-c]isoquinoline-7-carbaldehyde Step 1: A 50 ml three-necked flask equipped with a magnetic stirrer and with an argon intake is charged with 350 mg of 3-bromo-5-(2,6-difluorophenyl)-2-(2-trimethylsilanylethoxymethyl)-2H-pyrazolo[4,3-c]isoquinoline-7-carbaldehyde, prepared in step 5 of example 2, in 7.8 ml of 1,4-dioxane. 195 mg of 1-ethylsulphonylpiperidin-4-ylamine, 880 mg of caesium carbonate, 59 mg of 9,9-dimethyl-4,5-bis(diphenylphosphino)xanthene and 15 mg of palladium(II) acetate are added. The mixture is heated at reflux for 2 h. After cooling, the mixture is poured into water and extracted with AcOEt. The organic phase is washed with saturated NaCl solution, dried over MgSO$_4$, filtered and concentrated under RP. It is purified by flash chromatography on silica gel (15-40 μm), eluting with a mixture of cyclohexane and AcOEt (75/25 by vol.), to give 195 mg of 5-(2,6-difluorophenyl)-3-{[1-(ethylsulphonyl)piperidin-4-yl]amino}-1-{[2-(trimethylsilyl)ethoxy]methyl}-1H-pyrazolo[4,3-c]isoquinoline-7-carbaldehyde (yellow foam). LC-MS-DAD-ELSD 628=(M−H)(+).

Step 2: A microwave tube with a maximum capacity of 20 ml is charged with 195 mg of 5-(2,6-difluorophenyl)-3-{[1-(ethylsulphonyl)piperidin-4-yl]amino}-1-{[2-(trimethylsilyl)ethoxy]methyl}-1H-pyrazolo[4,3-c]isoquinoline-7-carbaldehyde, and 10 ml of 5N aqueous HCl solution. The mixture is microwave-heated at 100° C. for 20 min and then poured into water and extracted with AcOEt. The organic phase is washed with saturated NaCl solution, dried over MgSO$_4$, filtered and concentrated under RP. The product is purified by flash chromatography on silica gel (15-40 μm), eluting with a mixture of DCM and MeOH (95/5 by vol.). This gives 90 mg of 5-(2,6-difluorophenyl)-3-{[1-(ethylsulphonyl)piperidin-4-yl]amino}-1H-pyrazolo[4,3-c]isoquinoline-7-carbaldehyde in the form of a yellow foam. $^1$H NMR (500 MHz, DMSO-d6) δ ppm 1.23 (t, J=7.4 Hz, 3 H) 1.64 (m, 2 H) 2.10 (m, 2 H) 2.98 (m, 2H) 3.05 (q, J=7.4 Hz, 2 H) 3.62 (m, 2 H) 3.83 (m, 1 H) 6.18 (d, J=7.7 Hz, 1 H) 7.36 (t, J=7.8 Hz, 2 H) 7.71 (m, 1 H) 8.24 (broad s, 1 H) 8.34 (broad d, J=8.4 Hz, 1 H) 8.57 (d, J=8.4 Hz, 1 H) 10.11 (s, 1 H) 13.02 (s, 1 H). [M+H]+m/z=500.

Example 20

5-(2,6-difluorophenyl)-3-{[1-(ethylsulphonyl)piperidin-4-yl]amino}-1H-pyrazolo[4,3-c]isoquinoline-7-carbaldehyde oxime A 25 ml round-bottomed flask is charged with 30 mg of 5-(2,6-difluorophenyl)-3-{[1-(ethylsulphonyl)piperidin-4-yl]amino}-1H-pyrazolo[4,3-c]isoquinoline-7-carbaldehyde, prepared in example 19, in 2 ml of pyridine. 7 mg of hydroxylamine as the hydrochloride are added. After 1 h at RT, the mixture is evaporated under RP. The product is purified by flash chromatography on silica gel (15-40 μm), eluting with a DCM/methanol mixture (95/5 by vol.), to give 22 mg of 5-(2,6-difluorophenyl)-3-{[1-(ethylsulphonyl)piperidin-4-yl]amino}-1H-pyrazolo[4,3-c]isoquinoline-7-carbaldehyde oxime (yellow solid). $^1$H NMR (500 MHz, DMSO-d6) δ ppm with the E or Z isomerism: 1.23 (t, J=7.4 Hz, 3 H) 1.63 (m, 2 H) 2.09 (m, 2 H) 2.97 (m, 2 H) 3.05 (q, J=7.4 Hz, 2 H) 3.61 (m, 2 H) 3.80 (m, 1 H) 6.08 (broad m, 1 H) 7.33 (m, 2 H) 7.66 (m, 1 H) 7.86 (broad s, 1 H) 8.14 (broad d, J=8.3 Hz, 1 H) 8.30 (5, 1 H) 8.41 (d, J=8.3 Hz, 1 H) 11.45 (broad m, 1 H) 12.82 (broad m, 1 H). [M+H]+m/z=515.

Example 21

5-(2,6-difluorophenyl)-3-{[1-(ethylsulphonyl)piperidin-4-yl]amino}-1H-pyrazolo[4,3-c]isoquinolin-7-yl]methanol A 25 ml round-bottomed flask is charged with 30 mg of 5-(2,6-difluorophenyl)-3-{[1-(ethylsulphonyl)piperidin-4-yl]amino}-1H-pyrazolo[4,3-c]isoquinoline-7-carbaldehyde, prepared in example 19, in 2 ml of methanol. The mixture is cooled to 5° C. 12 mg of sodium borohydride are added. After 30 min at 5° C., the mixture is evaporated under RP. The solid obtained is taken up in 10 ml of 0.5M aqueous HCl solution. It is extracted with AcOEt and the organic phase is dried over MgSO$_4$, filtered and concentrated under RP. The product is purified by flash chromatography on silica gel (15-40 μm), eluting with a DCM/methanol mixture (95/5 by vol.), to give 12 mg of 5-(2,6-difluorophenyl)-3-{[1-(ethylsulphonyl)piperidin-4-yl]amino}-1H-pyrazolo[4,3-c]isoquinolin-7-yl]methanol (yellow solid). $^1$H NMR (500 MHz, DMSO-d6) δ ppm 1.23 (t, J=7.3 Hz, 3 H) 1.62 (m, 2 H) 2.09 (m, 2 H) 2.97 (m, 2 H) 3.05 (q, J=7.3 Hz, 2 H) 3.61 (m, 2 H) 3.79 (m, 1 H) 4.63 (d, J=5.5 Hz, 2 H) 5.36 (t, J=5.5 Hz, 1 H) 6.01 (d, J=7.8 Hz, 1 H) 7.32 (m, 2 H) 7.59 (broad s, 1 H) 7.66 (m, 1 H) 7.83 (broad d, J=8.3 Hz, 1 H) 8.35 (d, J=8.3 Hz, 1 H) 12.68 (s, 1 H). [M+H]+m/z=502.

Example 22

5-(2,6-difluorophenyl)-3-[(1-sulphamoylpiperidin-4-yl)amino]-2H-pyrazolo[4,3-c]isoquinoline-7-carboxamide Step 1: 707 mg of 3-bromo-5-(2,6-difluorophenyl)-1-{[2-(trimethylsilyl)ethoxy]methyl}-1H-pyrazolo[4,3-c]isoquinoline-7-carbonitrile are introduced into 17 ml of 1,4-dioxane. After argon has been bubbled through the mixture for 10 min, 846 mg of 4-aminopiperidine-1-sulphonamide, 2.15 g of caesium carbonate, 95 mg of 9,9-dimethyl-4,5-bis (diphenylphosphino)xanthene and 30 mg of palladium(II) acetate are added. The mixture is heated at reflux for 20 h. After cooling, the mixture is poured into water, extracted with AcOEt, washed with saturated NaCl solution, dried over MgSO$_4$, filtered and concentrated under RP. The product is purified by flash chromatography on silica gel (40-63 μm), eluting with a DCM/EtOH/NH3 (7N solution in MeOH) mixture (90/10/1 by vol.), to give 407 mg of 5-(2,6-difluorophenyl)-3-(piperidin-4-ylamino)-2-[2-(trimethylsilyl)ethoxy]methyl}-2H-pyrazolo[4,3-c]isoquinoline-7-carbonitrile (yellow oil). $^1$H NMR: −0.05 (broad s, 9 H) 0.88 (t, J=7.9 Hz, 2 H) 1.39 (m, 2 H) 1.93 (m, 2 H) 2.08 (broad m, 1 H) 2.39 (m, 2 H) 2.93 (m, 2 H) 3.71 (t, J=7.9 Hz, 2 H) 4.42 (m, 1H) 5.66 (s, 2 H) 6.58 (d, J=8.1 Hz, 1 H) 7.33 (t, J=7.9 Hz, 2 H) 7.66 (m, 1 H) 7.95 (broad s, 1 H) 8.12 (broad d, J=8.3 Hz, 1 H) 8.46 (d, J=8.3 Hz, 1 H).

Step 2: 375 mg of 5-(2,6-difluorophenyl)-3-(piperidin-4-ylamino)-2-[2-(trimethylsilyl)ethoxy]methyl}-2H-pyrazolo[4,3-c]isoquinoline-7-carbonitrile, 2 ml of DME and 84 mg of sulphamide are mixed and microwave-heated at 150° C. for 1 h. Following evaporation of the solvent, the excess sulphamide is precipitated by addition of ethyl ether, followed by filtration with suction on a frit and concentration of the filtrate under RP. This gives 439 mg of 4-{[7-cyano-5-(2,6-difluorophenyl)-2-{[2-(trimethylsilyl)ethoxy]methyl}-2H-pyrazolo[4,3-c]isoquinolin-3-yl]amino}piperidine-1-sulphonamide (yellow solid), $^1$H NMR: −0.05 (m, 9 H) 0.88 (t, J=7.9 Hz, 2 H) 1.61 (m, 2 H) 2.09 (m, 2 H) 2.53 (partially masked m, 2 H) 3.49 (m, 2 H) 3.67 (t, J=7.9 Hz, 2 H) 4.40 (m, 1H) 5.67 (s, 2 H) 6.67 (d, J=8.1 Hz, 1 H) 6.73 (s, 2 H) 7.34 (t, J=7.9 Hz, 2 H) 7.68 (m, 1 H) 7.95 (d, J=1.5 Hz, 1 H) 8.13 (dd, J=8.3, 1.5 Hz, 1 H) 8.47 (d, J=8.3 Hz, 1 H).

Step 3: 54 mg of 4-{[7-cyano-5-(2,6-difluorophenyl)-2-{[2-(trimethylsilyl)ethoxy]methyl}-2H-pyrazolo[4,3-c]isoquinolin-3-yl]amino}piperidine-1-sulphonamide are introduced into 0.5 ml of toluene. After cooling to 0° C. using an ice bath, 90 μl of 95% sulphuric acid are added and the mixture is stirred at RT for 24 h. It is cooled to 0° C. and neutralized with 9 ml of 7.5M aqueous ammonia solution. It is extracted with ethyl acetate, dried over MgSO$_4$, filtered and concentrated under RP. The product is purified by flash chromatography on silica gel (15-40 μm), eluting with a DCM/methanol mixture (95/05 by volume). This gives 7 mg of 5-(2,6-difluorophenyl)-3-[(1-sulphamoylpiperidin-4-yl) amino]-2H-pyrazolo[4,3-c]isoquinoline-7-carboxamide (yellow solid). $^1$H NMR: 1.67 (m, 2 H) 2.11 (m, 2 H) 2.67 (m, 2 H) 3.47 (m, 2 H) 3.71 (m, 1 H) 6.01 (d, J=8.2 Hz, 1 H) 6.70 (broad s, 2 H) 7.33 (t, J=7.7 Hz, 2 H) 7.55 (broad s, 1 H) 7.68 (m, 1 H) 8.17 (broad s, 1 H) 8.22 (broad s, 1 H) 8.35 (broad d, J=8.5 Hz, 1 H) 8.45 (d, J=8.5 Hz, 1 H) 12.84 (s, 1 H).

Example 23

4-({5-(2,6-difluorophenyl)-7-[(E/Z)-(hydroxyimino) methyl]-1H-pyrazolo[4,3-c]isoquinolin-3-yl}amino) piperidine-1-sulphonamide Step 1: Starting from 406 mg of 4-{[7-cyano-5-(2,6-difluorophenyl)-2-{[2-(trimethylsilyl)ethoxy]methyl}-2H-pyrazolo[4,3-c]isoquinolin-3-yl]amino}piperidine-1-sulphonamide, prepared in step 2 of example 22, and 4 ml of toluene, 3 ml of DCM are added and the mixture is cooled to 0° C. using an ice bath. 970 μl of diisobutylaluminium hydride are added dropwise and the mixture is stirred at 0° C. for 2 h. It is poured into 0.1M sodium hydroxide, extracted with AcOEt, washed with saturated NaCl solution, dried over MgSO$_4$, filtered and concentrated under RP. The product is purified by flash chromatography on silica gel (40-63 μm), eluting with a DCM/methanol mixture (90/10 by volume). This gives 251 mg of 4-{[5-(2,6-difluorophenyl)-7-formyl-2-{[2-(trimethylsilyl)ethoxy]methyl}-2H-pyrazolo[4,3-c]isoquinolin-3-yl]amino}piperidine-1-sulphonamide (yellow oil), which is used as it is in the following step.

Step 2: 250 mg of 4-{[5-(2,6-difluorophenyl)-7-formyl-2-{[2-(trimethylsilyl)ethoxy]methyl}-2H-pyrazolo[4,3-c]isoquinolin-3-yl]amino}piperidine-1-sulphonamide are introduced into 5 ml of toluene. After cooling to 0° C. using an ice bath, 206 μl of 95% sulphuric acid are added and stirring is continued at 0° C. for 1 h. The mixture is neutralized with 10 ml of 7.5M aqueous ammonia solution. It is extracted with ethyl acetate, dried over MgSO$_4$, filtered and concentrated under RP. The product is purified by flash chromatography on silica gel (15-40 μm), eluting with a DCM/ethanol mixture (90/10 by volume). This gives 38 mg of 4-{[5-(2,6-difluorophenyl)-7-formyl-1H-pyrazolo[4,3-c]isoquinolin-3-yl]amino}piperidine-1-sulphonamide (yellow solid). $^1$H NMR: 1.62-1.72 (m, 2 H) 2.11 (m, 2 H) 2.62-2.71 (m, 2 H) 3.47 (m, 2 H) 3.67-3.76 (m, 1 H) 6.14 (broad m, 1 H) 6.73 (s, 2 H) 7.36 (t, J=7.8 Hz, 2 H) 7.67-7.75 (m, 1 H) 8.23 (broad s, 1 H) 8.34 (broad d, J=8.3 Hz, 1 H) 8.57 (d, J=8.3 Hz, 1 H) 10.09 (s, 1 H) 13.04 (broad s, 1 H).

Step 3: 38 mg of 4-{[5-(2,6-difluorophenyl)-7-formyl-1H-pyrazolo[4,3-c]isoquinolin-3-yl]amino}piperidine-1-sulphonamide are introduced into 2 ml of pyridine and then 9 mg of hydroxylamine hydrochloride are added and the mixture is stirred at RT for 48 h. It is concentrated under RP and the solid obtained is taken up in AcOEt, washed with a 1M aqueous solution of potassium phosphate and then with saturated aqueous NaCl solution, dried over MgSO$_4$, filtered and concentrated under RP. The product is purified by flash chromatography on silica gel (20-45 μm), eluting with a DCM/EtOH mixture (80/20 by vol.), to give 19 mg of 4-({5-(2,6-difluorophenyl)-7-[(E/Z)-(hydroxyimino)methyl]-1H-pyrazolo[4,3-c]isoquinolin-3-yl}amino)piperidine-1-sulphonamide (yellow solid). $^1$H NMR: 1.60-1.73 (m, 2 H) 2.10 (m, 2 H) 2.68 (m, 2 H) 3.44-3.53 (m, 2 H) 3.70 (m, 1 H) 5.97 (broad d, J=6.4 Hz, 1 H) 6.70 (s, 2 H) 7.32 (t, J=7.9 Hz, 2 H) 7.68 (m, 1 H) 7.84 (broad s, 1 H) 8.14 (broad d, J=8.7 Hz, 1 H) 8.29 (s, 1 H) 8.41 (d, J=8.7 Hz, 1 H) 11.42 (broad s, 1 H) 12.79 (broad s, 1 H)

Example 24

5-(2,6-difluorophenyl)-N-[1-(methylsulphonyl)piperidin-4-yl]-7-(1H-pyrazol-4-yl)-1H-pyrazolo[4,3-c]isoquinolin-3-amine Step 1: 342 mg of 3-bromo-5-(2,6-difluorophenyl)-2-(2-trimethylsilanylethoxymethyl)-7-iodo-2H-pyrazolo[4,3-c]isoquinoline are introduced into 13 ml of 1,4-dioxane. 74 mg of 4-pyrazoleboronic acid, 77 mg of Pd(PPh$_3$)$_4$ and 165 mg of sodium carbonate are added. The mixture is heated at reflux for 4 h 30 min. After cooling, the mixture is poured into water, extracted with AcOEt, washed with saturated NaCl solution, dried over MgSO$_4$, filtered and concentrated under RP. The product is purified by flash chromatography on silica gel (15-40 μm), eluting with a DCM/methanol mixture (95/05 by vol.), to give 136 mg of 3-bromo-5-(2,6-difluorophenyl)-7-(1H-pyrazol-4-yl)-2-{[2-(trimethylsilyl)ethoxy]methyl}-2H-pyrazolo[4,3-c]isoquinoline (white foam), which is used as it is in the following step.

Step 2: 115 mg of 3-bromo-5-(2,6-difluorophenyl)-7-(1H-pyrazol-4-yl)-2-{[2-(trimethylsilyl)ethoxy]methyl}-2H-pyrazolo[4,3-c]isoquinoline are introduced into 2 ml of DMF, 0.26 ml of diisopropylethylamine and 77 μl of 2-(trimethylsilyl)ethoxymethyl chloride. The reaction mixture is stirred at RT for 18 h and then poured into water, extracted with AcOEt, washed with saturated NaCl solution, dried over MgSO$_4$, filtered and concentrated under RP. The product is purified by chromatography on silica gel (20-45 μm), eluting with a mixture of DCM and methanol (98/02 by vol.), to give 116 mg of 3-bromo-5-(2,6-difluorophenyl)-2-{[2-(trimethylsilyl)ethoxy]methyl}-7-(1-{[2-(trimethylsilyl)ethoxy]methyl}-1H-pyrazol-4-yl)-2H-pyrazolo[4,3-c]isoquinoline (yellow powder). $^1$H NMR: −0.01 (d, J=5.9 Hz, 4 H) 0.82-1.00 (m, 1 H) 3.60 (t, J=7.8 Hz, 1 H) 3.77 (t, 1 H) 5.46 (s, 1 H) 5.92 (s, 1 H) 7.42 (t, 1 H) 7.71-7.83 (m, 1 H) 8.03 (s, 1 H) 8.28 (dd, 1 H) 8.43 (s, 1 H) 8.58 (d, J=8.3 Hz, 1 H).

Step 3: 110 mg of 3-bromo-5-(2,6-difluorophenyl)-2-{[2-(trimethylsilyl)ethoxy]methyl}-7-(1-{[2-(trimethylsilyl)ethoxy]methyl}-1H-pyrazol-4-yl)-2H-pyrazolo[4,3-c]isoquinoline are introduced into 5 ml of 1,4-dioxane. After argon has been bubbled through the mixture for 10 min, 57 mg of 1-methanesulphonylpiperidin-4-ylamine, 199 mg of caesium carbonate, 16 mg of 9,9-dimethyl-4,5-bis(diphenylphosphino)xanthene and 5 mg of palladium(II) acetate are added. The mixture is heated at reflux for 2 h. After cooling, the mixture is poured into water, extracted with AcOEt, washed with saturated NaCl solution, dried over MgSO$_4$, filtered and concentrated under RP. The product is purified by flash chromatography on silica gel (40-63 μm), eluting with a DCM/methanol mixture (97.5/2.5 by vol.), to give 77 mg of 5-(2,6-difluorophenyl)-N-[1-(methylsulphonyl)piperidin-4-yl]-2-{[2-(trimethylsilyl)ethoxy]methyl}-7-(1-{[2-(trimethylsilyl)ethoxy]methyl}-1H-pyrazol-4-yl)-2H-pyrazolo[4,3-c]isoquinolin-3-amine (yellow foam). $^1$H NMR: −0.07 (s, 9 H)−0.02 (s, 9 H) 0.34 (t, J=8.3 Hz, 2 H) 0.90 (t, J=8.3 Hz, 2 H) 1.56-1.68 (m, 2 H) 2.11 (m, 2 H) 2.76 (m, 2 H) 2.86 (s, 3 H) 3.56 (t, J=8.3 Hz, 2 H) 3.61 (m, 2 H) 3.68 (t, J=8.3 Hz, 2 H) 4.47-4.57 (m, 1 H) 5.42 (s, 2 H) 5.65 (s, 2 H) 6.46 (d, J=8.0 Hz, 1 H) 7.34 (t, J=7.9 Hz, 2 H) 7.59 (broad s, 1 H) 7.66 (m, 1 H) 7.92 (s, 1 H) 8.05 (dd. J=8.3, 1.7 Hz, 1 H) 8.31 (s, 1 H) 8.34 (d, J=8.3 Hz, 1 H).

Step 4: 73 mg of 5-(2,6-difluorophenyl)-N-[1-(methylsulphonyl)piperidin-4-yl]-2-{[2-(trimethylsilyl)ethoxy]methyl}-7-(1-{[2-(trimethylsilyl)ethoxy]methyl}-1H-pyrazol-4-yl)-2H-pyrazolo[4,3-c]isoquinolin-3-amine are introduced into 5 ml of DCM. After cooling to 0° C. using an ice bath, 0.58 ml of TFA is added and the mixture is stirred at RT for 5 h. The reaction mixture is concentrated under RP and the solid obtained is taken up in 23 ml of water, neutralized with 7.5M aqueous ammonia solution. It is extracted with ethyl acetate, dried over MgSO$_4$, filtered and concentrated under RP. The product is purified by flash chromatography on silica gel (15-40 μm), eluting with DCM and then with a DCM/methanol mixture (90/10 by vol.), to give 5 mg of 5-(2,6-difluorophenyl)-N-[1-(methylsulphonyl)piperidin-4-yl]-7-(1H-pyrazol-4-yl)-1H-pyrazolo[4,3-c]isoquinolin-3-amine (yellow solid). $^1$H NMR: 1.61-1.74 (m, 2 H) 2.06-2.16 (m, 2 H) 2.87 (s, 3 H) 2.89-2.95 (m, 2 H) 3.52-3.60 (m, 2 H) 3.75-3.84 (m, 1 H) 5.98 (d, J=8.2 Hz, 1 H) 7.31 (t, J=8.0 Hz, 2 H) 7.65-7.71 (m, 2 H) 7.82-7.88 (broad m, 1 H) 8.15-8.24 (broad m, 1 H) 8.18 (broad d, J=8.3 Hz, 1 H) 8.40 (d, J=8.3 Hz, 1 H) 12.66 (s, 1 H) 13.05 (broad s, 1 H).

Example 25

5-(2,6-difluorophenyl)-N-[1-(methylsulphonyl)piperidin-4-yl]-7-(2H-1,2,3-triazol-4-yl)-1H-pyrazolo[4,3-c]isoquinolin-3-amine Step 1: 239 mg of 5-(2,6-difluorophenyl)-3-([1-(methylsulphonyl)piperidin-4-yl]amino}-2-{[2-(trimethylsilyl)ethoxy]methyl}-7-ethynyl-2H-pyrazolo[4,3-c]isoquinoline, prepared in step 4 of example 7, are introduced into 4 ml of methanol and 4 ml of DMF, and 208 µL of trimethylsilyl azide and 15 mg of copper(I) iodide are added. After 2 h of heating at 100° C., 104 µl of trimethylsilyl azide and 7 mg of copper(I) iodide are added and heating at 100° C. is continued for 2 h. After cooling, the mixture is poured into water, extracted with AcOEt, washed with saturated NaCl solution, dried over $MgSO_4$, filtered and concentrated under RP. The product is purified by flash chromatography on silica gel (40-63 µm), eluting with a DCM/methanol mixture (95/05 by vol.), to give 121 mg of 5-(2,6-difluorophenyl)-N-[1-(methylsulphonyl)piperidin-4-yl]-7-(2H-1,2,3-triazol-4-yl)-2-{[2-(trimethylsilyl)ethoxy]methyl}-2H-pyrazolo[4,3-c]isoquinolin-3-amine (yellow foam). $^1$H NMR: −0.04 (s, 9 H) 0.90 (m, 2 H) 1.61 (m, 2 H) 2.12 (m, 2 H) 275 (m, 2 H) 2.85 (s, 3 H) 3.57 (m, 2 H) 3.68 (m, 2 H) 4.47 (m, 1 H) 5.66 (s, 2 H) 6.49 (d, J=8.4 Hz, 1 H) 7.36 (t, J=8.0 Hz, 2 H) 7.67 (m, 1 H) 8.01 (broad s, 1 H) 8.25 (broad d, J=8.5 Hz, 1 H) 8.41 (d, J=8.5 Hz, 1 H) 8.43 (partially masked broad m, 1 H) 15.28 (broad m, 1 H).

Step 2; 116 mg of 5-(2,6-difluorophenyl)-N-[1-(methylsulphonyl)piperidin-4-yl]-7-(2H-1,2,3-triazol-4-yl)-2-{[2-(trimethylsilyl)ethoxy]methyl}-2H-pyrazolo[4,3-c]isoquinolin-3-amine are introduced into 10 ml of DCM. After cooling to 0° C. using an ice bath, 1.1 ml of TFA are added and the mixture is stirred at RT for 5 h. It is concentrated under RP and the solid obtained is taken up in 60 ml of water, neutralized with 7.5M aqueous ammonia solution. It is extracted with ethyl acetate, dried over $MgSO_4$, filtered and concentrated under RP. The product is purified by flash chromatography on silica gel (15-40 µm), eluting with a DCM/methanol mixture (92.5/7.5 by vol.), to give 10 mg of 5-(2,6-difluorophenyl)-N-[1-(methylsulphonyl)piperidin-4-yl]-7-(2H-1,2,3-triazol-4-yl)-1H-pyrazolo[4,3-c]isoquinolin-3-amine (yellow solid). $^1$H NMR: 1.62-1.75 (m, 2 H) 2.10 (m, 2 H) 2.82-2.97 (m, 5 H) 3.57 (m, 2 H) 3.74-3.86 (m, 1 H) 6.04 (d, J=8.0 Hz, 1 H) 7.35 (t, J=8.0 Hz, 2 H) 7.63-7.75 (m, 1H) 8.13 (broad s, 1 H) 8.39 (broad d, J=8.6 Hz, 1 H) 8.45 (broad m, 1 H) 8.49 (d, J=8.6 Hz, 1 H) 12.77 (s, 1 H) 15.23 (broad m, 1 H).

Example 26

4-{[7-cyano-5-(2,6-difluorophenyl)-1H-pyrazolo[4,3-c]isoquinolin-3-yl]amino}piperidine-1-sulphonamide 306 mg of 4-{[7-cyano-5-(2,6-difluorophenyl)-2-{[2-(trimethylsilyl)ethoxy]methyl}-2H-pyrazolo[4,3-c]isoquinolin-3-yl]amino}piperidine-1-sulphonamide are introduced into 20 ml of DCM. After cooling to 0° C. using an ice bath, 1.5 ml of TFA are added and the mixture is stirred at RT for 16 h. It is concentrated under RP and the solid obtained is taken up in 30 ml of water, neutralized with 2 ml of 7.5M aqueous ammonia solution. It is extracted with ethyl acetate, dried over $MgSO_4$, filtered and concentrated under RP. The product is purified by flash chromatography on silica gel (15-40 µm), eluting with a DCM/methanol/$NH_4OH$ mixture (92.5/7.5/0.75 by volume). This gives 8 mg of 4-{[7-cyano-5-(2,6-difluorophenyl)-1H-pyrazolo[4,3-c]isoquinolin-3-yl]amino}piperidine-1-sulphonamide. $^1$H NMR: 1.61-1.73 (m, 2 H) 2.09 (m, 2 H) 2.63-2.72 (m, 2 H) 3.47 (m, 2 H) 3.67-3.76 (m, 1 H) 6.13 (d, J=7.0 Hz, 1 H) 6.70 (s, 2 H) 7.34 (t, J=7.8 Hz, 2 H) 7.65-7.74 (m, 1 H) 8.18 (broad s, 1 H) 8.28 (broad d, J=8.6 Hz, 1 H) 8.56 (d, J=8.6 Hz, 1 H) 13.05 (s, 1 H).

Example 27

4-{[5-(2,6-difluorophenyl)-7-(hydroxymethyl)-1H-pyrazolo[4,3-c]isoquinolin-3-yl]amino}piperidine-1-sulphonamide Step 1: 449 mg of 4-{[5-(2,6-difluorophenyl)-7-formyl-2-{[2-(trimethylsilyl)ethoxy]methyl}-2H-pyrazolo[4,3-c]isoquinolin-3-yl]amino}piperidine-1-sulphonamide, prepared in step 1 in example 23, are introduced into 20 ml of methanol. After cooling to 0° C. using an ice bath, 34 mg of $NaBH_4$ are added and the mixture is stirred for 1 h. 3 ml of acetone are added and then the mixture is poured into saturated aqueous sodium bicarbonate solution. It is extracted with AcOEt, washed with saturated NaCl solution, dried over $MgSO_4$, filtered and concentrated under RP. The product is purified by flash chromatography on silica gel (15-40 µm), eluting with a DCM/methanol/$NH_4OH$ mixture (95/5/0.5 by volume). This gives 197 mg of 4-{[5-(2,6-difluorophenyl)-7-(hydroxymethyl)-2-{[2-(trimethylsilyl)ethoxy]methyl}-2H-pyrazolo[4,3-c]isoquinolin-3-yl]amino}piperidine-1-sulphonamide (yellow foam). $^1$H NMR: −0.05 (s, 9 H) 0.88 (t, J=8.3, 2 H) 158 (m, 2 H) 2.09 (m, 2 H) 2.52 (partially masked m, 2 H) 3.48 (m, 2 H) 3.66 (t, J=8.3 Hz, 2 H) 4.34-4.43 (m, 1 H) 4.58 (d, J=5.7 Hz, 2 H) 5.38 (t, J=57 Hz, 1 H) 5.62 (s, 2 H) 6.39 (d, J=8.3 Hz, 1 H) 6.70 (s, 2 H) 7.30 (t, J=7.8 Hz, 2 H) 7.43 (broad s, 1 H) 7.58-7.67 (m, 1 H) 7.70 (dd, J=8.3, 1.5 Hz, 1 H) 8.33 (d, J=8.3 Hz, 1 H).

Step 2: 194 mg of 4-{[5-(2,6-difluorophenyl)-7-(hydroxymethyl)-2-{[2-(trimethylsilyl)ethoxy]methyl}-2H-pyrazolo[4,3-c]isoquinolin-3-yl]amino}piperidine-1-sulphonamide are introduced into 25 ml of DCM. After cooling to 0° C. using an ice bath, 1.9 ml of TFA are added and the mixture is stirred at RT for 2 h 30 min. It is concentrated under RP and the solid obtained is taken up in 50 ml of water, neutralized with 2.5 ml of 7.5M aqueous ammonia solution. It is extracted with ethyl acetate, dried over $MgSO_4$, filtered and concentrated under RP. The product is purified by flash chromatography on silica gel (15-40 µm), eluting with a DCM/methanol/$NH_4OH$ mixture (90/10/1 by volume). This gives 28 mg of 4-{[5-(2,6-difluorophenyl)-7-(hydroxymethyl)-1H-pyrazolo[4,3-c]isoquinolin-3-yl]amino}piperidine-1-sulphonamide. $^1$H NMR: 1.60-1.73 (m, 2 H) 2.05-2.16 (m, 2 H) 2.62-2.73 (m, 2 H) 3.46 (d, J=11.2 Hz, 2 H) 3.64-3.76 (m, 1 H) 4.63 (d, J=5.4 Hz, 2 H) 5.34 (t, J=5.9 Hz, 1 H) 5.75 (s, 1 H) 5.91 (d, 1 H) 6.70 (s, 2 H) 7.32 (t, 2 H) 7.59 (s, 1 H) 7.61-7.71 (m, 1 H) 7.84 (dd, 1 H) 8.35 (d, J=8.3 Hz, 1 H) 12.66 (s, 1 H).

Example 28

4-{[5-(2,6-difluorophenyl)-7-fluoro-1H-pyrazolo[4,3-c]isoquinolin-3-yl]amino}piperidine-1-sulphonamide Step 1: Using the procedure of step 3 of example 24, 310 mg of 3-bromo-5-(2,6-difluorophenyl)-7-fluoro-2-{[2-(trimethylsilyl)ethoxy]methyl}-1H-pyrazolo[4,3-c]isoquinoline are introduced into 8 ml of 1,4-dioxane. After argon has been bubbled through the mixture for 10 min, 244 mg of 2-methylpropan-2-yl 4-aminopiperidine-1-carboxylate, 755 mg of caesium carbonate, 63 mg of 9,9-dimethyl-4,5-bis(diphenylphosphino)xanthene and 20 mg of palladium(II) acetate are added. The mixture is heated at reflux for 3 h. After cooling, the mixture is poured into water, extracted with AcOEt, washed with saturated NaCl solution, dried over $MgSO_4$, filtered and concentrated under RP. The product is purified by flash chromatography on silica gel (15-40 μm), eluting with a DCM/methanol mixture (90/10 by vol.), to give 340 mg of 2-methylpropan-2-yl 4-{[5-(2,6-difluorophenyl)-7-fluoro-2-{[2-(trimethylsilyl)ethoxy]methyl}-2H-pyrazolo[4,3-c]isoquinolin-3-yl]amino}piperidine-1-carboxylate (yellow solid). LC-MS-DAD-ELSD: 628=(M+H).

Step 2: 340 mg of 2-methylpropan-2-yl 4-{[5-(2,6-difluorophenyl)-7-fluoro-2-{[2-(trimethylsilyl)ethoxy]methyl}-2H-pyrazolo[4,3-c]isoquinolin-3-yl]amino}piperidine-1-carboxylate are introduced into 16 ml of methanol and 1.5 ml of THF. After cooling to 0° C. using an ice bath, 2.7 ml of a 4N solution of hydrochloric acid in dioxane are added and the mixture is stirred at RT for 5 h. It is poured into 200 ml of saturated sodium bicarbonate solution and then extracted with ethyl acetate, dried over $MgSO_4$, filtered and concentrated under RP. The product is purified by flash chromatography on silica gel (15-40 μm), eluting with a DCM/methanol/aqueous ammonia mixture (90/10/1 by vol.), to give 180 mg of 5-(2,6-difluorophenyl)-7-fluoro-N-(piperidin-4-yl)-2-{[2-(trimethylsilyl)ethoxy]methyl}-2H-pyrazolo[4,3-c]isoquinolin-3-amine (yellow solid), LC-MS-DAD-ELSD: 528=(M+H).

Step 3: 180 mg of 5-(2,6-difluorophenyl)-7-fluoro-N-(piperidin-4-yl)-2-([2-(trimethylsilyl)ethoxy]methyl}-2H-pyrazolo[4,3-c]isoquinolin-3-amine, 2 ml of DME and 41 mg of sulphamide are mixed and microwave-heated at 150° C. for 1 h. The mixture is poured into water, extracted with AcOEt, washed with saturated NaCl solution, dried over $MgSO_4$, filtered and concentrated under RP. The product is purified by flash chromatography on silica gel (15-40 μm), eluting with a DCM/methanol/aqueous ammonia mixture (95/05/0.5 by vol.), to give 183 mg of 4-{[5-(2,6-difluorophenyl)-7-fluoro-2-{[2-(trimethylsilyl)ethoxy]methyl}-2H-pyrazolo[4,3-c]isoquinolin-3-yl]amino}piperidine-1-sulphonamide (yellow solid). LC-MS-DAD-ELSD: 607=(M+H).

Step 4:
183 mg of 4-O-(2,6-difluorophenyl)-7-fluoro-2-{[2-(trimethylsilyl)ethoxy]methyl}-2H-pyrazolo[4,3-c]isoquinolin-3-yl]amino}piperidine-1-sulphonamide are introduced into 24 ml of DCM. After cooling to 0° C. using an ice bath, 1.9 ml of TFA are added and the mixture is stirred at RT for 2 h 30 min. It is concentrated under RP and the solid obtained is taken up in 50 ml of water, neutralized with 2.5 ml of 7.5M aqueous ammonia solution. It is extracted with ethyl acetate, dried over $MgSO_4$, filtered and concentrated under RP. The product is purified by flash chromatography on silica gel (15-40 μm), eluting with a DCM/methanol/aqueous ammonia mixture (90/10/1 by volume). This gives 28 mg of 4-{[5-(2,6-difluorophenyl)-7-fluoro-1H-pyrazolo[4,3-c]isoquinolin-3-yl]amino}piperidine-1-sulphonamide (pale yellow solid). LC-MS-DAD-ELSD: 477=(M+H) $^1$H NMR: 1.66 (m, 2 H) 2.11 (m, 2 H) 2.67 (m, 2H) 3.46 (m, 2 H) 370 (m, 1 H) 6.03 (d, J=77 Hz, 1 H) 6.72 (s, 2 H) 7.26-7.40 (m, 3 H) 7.68 (m, 1H) 7.88 (td J=9.0, 2.5 Hz, 1 H) 8.50 (dd, J=9.0, 5.5 Hz, 1 H) 12.79 (s, 1 H).

Determination of $IC_{50}$ for HeLa Cells (ATCC CCL-2)

This test is carried out using adherent tumour cell lines. Their proliferation is measured via the amount of $^{14}$C-thymidine incorporated within the cells. These cells are placed in 96-well Cytostar plates with the culture medium and are incubated for 4 h at 37° C.-5% $CO_2$. The products under test are then added and the plates are replaced in the incubator. $^{14}$C-thymidine is added to the medium after 72 h of treatment and the cells are then incubated for 24 h. The incorporation of $^{14}$C-thymidine is measured using a MicroBeta reader (Perkin Elmer) after these 24 h of "pulse". The total time of treatment of the cells with the product under test is 96 h.

For each assay, the plates are prepared at the cell concentrations employed. The products are tested at 10 concentrations in duplicate. The first concentration is usually 10 μM, but it may vary, as may the degree of dilution, depending on the activity level of the products. The serial dilutions are made in pure DMSO and then each concentration is diluted in the culture medium. All of the products are tested in two independent assays.

Materials Used

Dulbecco (Gibco 11960-044)

Inactivated foetal calf serum (FCS) (Gibco 10500-056)

Penicillin-Streptomycin-Glutamine (PSG) (Gibco 10378-016)

96-well Cytostar plate (Amersham RPNQ0162)

DMSO (Sigma D2650)

$^{14}$C-Thymidine (NEN NEC-568)

TABLE I

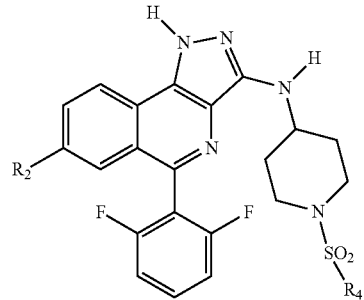

(II)

| example | synthesis scheme | $R_2$ | $R_4$ | $IC_{50}$ HeLa [nM] |
|---|---|---|---|---|
| 1 | 1 - route 3 | —C(=O)NH$_2$ | —Me | 259 |
| 2 | 1 - route 2 | —CH=N—OH | —Me | 100 |
| 3 | 1 - route 2 | —CH$_2$OH | —Me | 248 |
| 4 | 1 - route 2 | —C(=O)NH$_2$ | —CF$_3$ | 789 |
| 5 | 1 - route 1 | —CH=CH$_2$ | —Me | 2580 |
| 6 | 1 - route 1 | —F | —Me | 890 |
| 7 | 1 - route 2 | —C≡CH | —Me | 1500 |
| 8 | 1 - route 1 | —C(=O)OMe | —Me | 7285 |
| 9 | 1 - route 3 | —C(=S)NH$_2$ | —Me | 597 |
| 10 | 1 - route 1 | —H | —Me | 2044 |
| 11 | 1 - route 1 | —CN | —Cy | 909 |
| 12 | 1 - route 1 | —CN | —Me | 899 |
| 13 | 1 - route 1 | —CN | —Et | 954 |
| 14 | 1 - route 3 | —C(=O)NH$_2$ | —Cy | 413 |
| 15 | 1 - route 2 | —C(=O)H | —Me | 488 |
| 16 | 1 - route 3 | HO—N(H)—C(NH)— (substructure) | —Me | 2350 |
| 17 | 1 - route 2 | —CH$_2$F | —Me | 263 |
| 18 | 1 - route 2 | —C(=O)NH$_2$ | —Et | 554 |
| 19 | 1 - route 1 | —C(=O)H | —Et | 451 |
| 20 | 1 - route 2 | —CH=N—OH | —Et | 138 |
| 21 | 1 - route 2 | —CH$_2$OH | —Et | 338 |
| 22 | 1 - route 2 | —C(=O)NH$_2$ | —NH$_2$ | 411 |
| 23 | 1 - route 3 | —CH=N—OH | —NH$_2$ | 126 |

TABLE I-continued

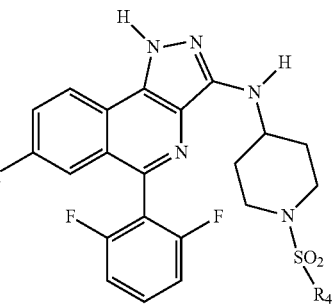

| example | synthesis scheme | R₂ | R₄ | IC₅₀ HeLa [nM] |
|---|---|---|---|---|
| 24 | 1 - route 2 | 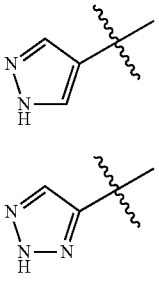 | —Me | 2125 |
| 25 | 1 - route 2 | 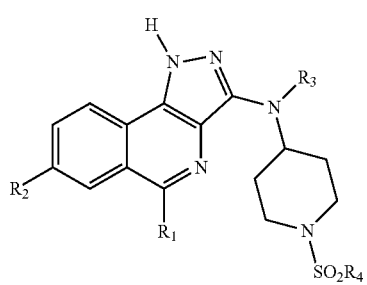 | —Me | 2283 |
| 26 | 1 - route 1 | —CN | —NH₂ | 1660 |
| 27 | 1 - route 2 | —CH₂OH | —NH₂ | 456 |
| 28 | 6 | —F | —NH₂ | 230 |

Me: methyl,
Et: ethyl,
Cy: cyclopropyl

The invention claimed is:

1. A compound of formula (I):

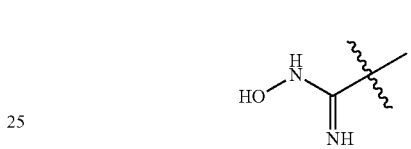

in which:
R₁ represents a phenyl group which is optionally substituted by one or more halogen atoms;
R₂ represents:
a hydrogen or halogen atom or a cyano group;
a group —C(=O)Y in which Y represents a hydrogen atom or a group —NH₂ or —OR$_a$;
a group —C(=S)NH₂;
a group —C(=NH)NH—OH;
a group —CH₂OH or —CH₂F;
a group —CH=N—OH;
a group —CH=CH₂ or —C≡C—R$_a$;
a group

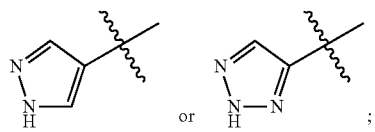

where R$_a$ represents a hydrogen atom or a (C₁-C₄)alkyl group;
R₃ represents a hydrogen atom or a (C₁-C₄)alkyl group;
R₄ represents an —NH₂, (C₁-C₄)alkyl, (C₁-C₄)fluoroalkyl or (C₃-C₇)cycloalkyl group.

2. The compound according to claim 1, wherein R₁ represents a 2,6-difluoro-phenyl group and R₃ represents a hydrogen atom.

3. The compound according to claim 1, wherein R₂ is selected from: H, —C(=O)H, —C(=O)NH₂, —CH=N—OH, —CH₂OH, —CH=CH₂, —F, —C≡CH, —C(=O)OCH₃, —C(=S)NH₂, —CN, 4. The compound according to claim 1, wherein R₄ is selected from: —CH₃, —CH₂CH₃, —CF₃ or the cyclopropyl group.

5. The compound according to claim 1 selected from the following list:
5-(2,6-difluorophenyl)-3-{[1-(methylsulphonyl)piperidin-4-yl]amino}-1H-pyrazolo[4,3-c]isoquinoline-7-carboxamide;
5-(2,6-difluorophenyl)-3-{[1-(methylsulphonyl)piperidin-4-yl]amino}1-1H-pyrazolo[4,3-c]isoquinoline-7-carbaldehyde oxime;
5-(2,6-difluorophenyl)-3-{[1-(methylsulphonyl)piperidin-4-yl]amino}-1H-pyrazolo[4,3-c]isoquinolin-7-yl] methanol;
5-(2,6-difluorophenyl)-3-{[1-(trifluoromethanesulphonyl)piperidin-4-yl]amino}-1H-pyrazolo[4,3-c]isoquinoline-7-carboxamide;
5-(2,6-difluorophenyl)-3-{[1-(methylsulphonyl)piperidin-4-yl]amino }-7-vinyl-1H-pyrazolo[4,3-c]isoquinoline;
5-(2,6-difluorophenyl)-7-fluoro-3-{[1-(methyl sulphonyl)piperidin-4-yl]amino}-1H-pyrazolo[4,3-c]isoquinoline;
5-(2,6-difluorophenyl)-3-{[1-(methylsulphonyl)piperidin-4-yl]amino }-7-ethynyl-1H-pyrazolo[4,3-c]isoquinoline;
methyl 5-(2,6-difluorophenyl)-3-{[1-(methylsulphonyl) piperidin-4-yl]amino}-1H-pyrazolo[4,3c] isoquinoline-7-carboxylate;
5-(2,6-difluorophenyl)-3-{[1-(methylsulphonyl)piperidin-4-yl]amino}-1H-pyrazolo[4,3-c]isoquinoline-7-carbothioamide;
5-(2,6-difluorophenyl)-3-{[1-(methylsulphonyl)piperidin-4-yl]amino}-1H-pyrazolo[4,3-c]isoquinoline;
5-(2,6-difluorophenyl)-3-{[1-(cyclopropylsulphonyl)piperidin-4-yl]amino}-1H-pyrazolo[4,3-c] isoquinoline-7-carbonitrile;
5-(2,6-difluorophenyl)-3-{[1-(methylsulphonyl)piperidin-4-yl]amino}-1H-pyrazolo[4,3-c]isoquinoline-7-carbonitrile;

5-(2,6-difluorophenyl)-3-[1-(ethylsulphonyl)piperidin-4-yl]amino-1H-pyrazolo[4,3-c]isoquinoline-7-carbonitrile;
5-(2,6-difluorophenyl)-3-{[1-(cyclopropylsulphonyl)piperidin-4-yl]amino}-1H-pyrazolo[4,3-c]isoquinoline-7-carboxamide;
5-(2,6-difluorophenyl)-3-{[1-(methylsulphonyl)piperidin-4-yl]amino}-1H-pyrazolo[4,3-c]isoquinoline-7-carbaldehyde;
5-(2,6-difluorophenyl)-N-hydroxy-3{[1-(methylsulphonyl)piperidin-4-yl]amino}-1H-pyrazolo[4,3-c]isoquinoline-7-carboximidamide;
[5-(2,6-difluorophenyl)-7-(fluoromethyl)-N-[1-(methylsulphonyl)piperidin-4-yl]-1H-pyrazolo[4,3-c]isoquinolin-3-amine;
5-(2,6-difluorophenyl)-3-{[1-(ethylsulphonyl)piperidin-4-yl]amino}-1H-pyrazolo[4,3-c]isoquinoline-7-carboxamide;
5-(2,6-difluorophenyl)-3-{[1-(ethylsulphonyl)piperidin-4-yl]amino}-1H-pyrazolo[4,3-c]isoquinoline-7-carbaldehyde;
5-(2,6-difluorophenyl)-3-{[1-(ethylsulphonyl)piperidin-4-yl]amino}-1H-pyrazolo[4,3-c]isoquinoline-7-carbaldehyde oxime;
5-(2,6-difluorophenyl)-3-{[1-(ethylsulphonyl)piperidin-4-yl]amino}-1H-pyrazolo[4,3-c]isoquinolin-7-yl] methanol;
5-(2,6-difluorophenyl)-3-[(1-sulphamoylpiperidin-4-yl)amino]-2H-pyrazolo[4,3-c]isoquinoline-7-carboxamide;
4-({5-(2,6-difluorophenyl)-7-[(E/Z)-(hydroxyimino)methyl]-1H-pyrazolo[4,3-c]isoquinolin-3-yl}amino)piperidine-1-sulphonamide;
5-(2,6-difluorophenyl)-N-[1-(methylsulphonyl)piperidin-4-yl]-7-(1H-pyrazol-4-yl)-1H-pyrazolo[4,3-c]isoquinolin-3-amine;
5-(2,6-difluorophenyl)-N-[1-(methylsulphonyl)piperidin-4-yl]-7-(2H-1,2,3-triazol-4-yl)-1H-pyrazolo[4,3-c]isoquinolin-3-amine;
4-{[7-cyano-5-(2,6-difluorophenyl)-1H-pyrazolo[4,3-c]isoquinolin-3-yl]amino}piperidine-1-sulphonamide;
4-{[5-(2,6-difluorophenyl)-7-(hydroxymethyl)-1H-pyrazolo[4,3-c]isoquinolin-3-yl]amino}piperidine-1-sulphonamide;
4-{[5-(2,6-difluorophenyl)-7-fluoro-1H-pyrazolo[4,3-c]isoquinolin-3-yl]amino}piperidine-1-sulphonamide.

6. The compound according to claim 1, in the form of a base or an acid addition salt.

7. A process for preparing a compound of formula:

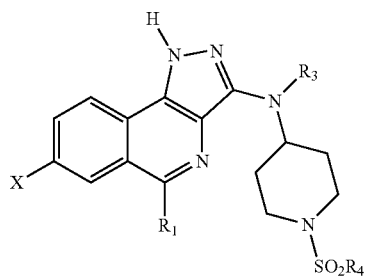

in which:
$R_1$ represents a phenyl group which is optionally substituted by one or more halogen atoms;
$R_3$ represents a hydrogen atom or a $(C_1-C_4)$alkyl group;
$R_4$ represents an $—NH_2$, $(C_1-C_4)$alkyl, $(C_1-C_4)$fluoroalkyl or $(C_3-C_7)$cycloalkyl group, and X represents a hydrogen or fluorine atom or a group cyano; $—C(=O)H$; $—CH=CH_2$; $—C\equiv C—SiMe_3$; $—COOR_a$, $R_a$ representing a hydrogen atom or a $(C_1-C_4)$alkyl group; or the group

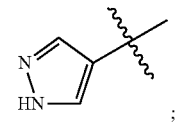

comprising:
(i) coupling the compounds $P_1$ and $P_2$ in the presence of a palladium complex and optionally of a base:

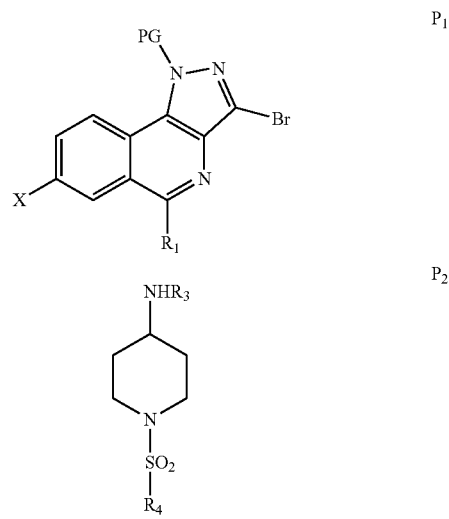

(ii) deprotecting the product obtained in the preceding step (i), or else comprising:
(i') reacting the compound $P'_4$ of formula:

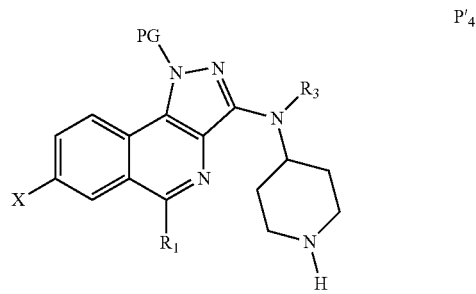

with $R_4SO_2Cl$,
(ii') deprotecting the product obtained in the preceding step (i),
where PG represents a protective group for the NH function of the pyrazole ring.

8. A process for preparing a compound of formula (I):

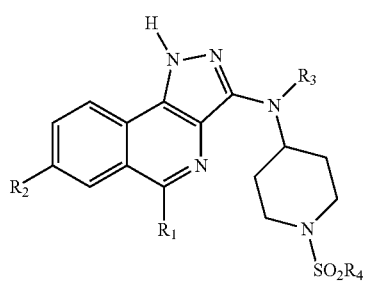

(I)

in which R₁, R₃ and R₄ are as defined in claim 1, and R₂ represents one of the following groups: —C(=O)NH₂, —C(=S)NH₂, —C(O)H, —CH=N—OH, —CH₂OH, —CH₂F, —C≡CH,

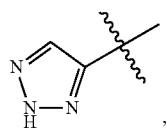

, from a compound of formula:

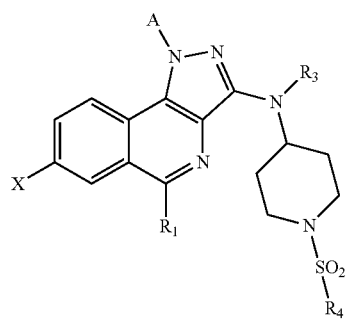

in which X represents a group —CN, —CHO, —CH₂OH, —C≡CH or —C≡C—SiMe₃ and A represents a hydrogen atom or a protective group PG protecting the NH function of the pyrazole ring, comprising:

(i)

hydrolyzing the group X=—CN to group R₂=—C(=O)NH₂ or —C(=O)OH; or converting the group X=—CN to group R₂=—C(=S)NH₂ in the presence of ammonium sulphide with microwaves; or reducing the group X=—CN to group R₂=—C(O)H; or converting the group X=—C(=O)H to group R₂=—CH=N—OH in the presence of NH₂OH; or reducing the group X=—C(=O)H to group R₂=—CH₂OH; or converting the group X=—C≡C—SiMe₃ to group R₂=—C≡CH; or fluorinating the group X=—CH₂OH to group R₂=—CH₂F; or converting the group X=—C≡CH to group

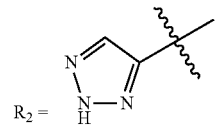 [SMILES: *c1cn[nH]n1]

R₂ = by cycloaddition in the presence of trimethylsilyl azide N₃SiMe₃; and (ii) where appropriate, deprotecting the product obtained in the preceding step (i).

9. A pharmaceutical composition comprising the compound according to claim 1 and at least one pharmaceutically acceptable excipient.

10. An anticancer agent comprising the compound of claim 1.

11. A compound of formula:

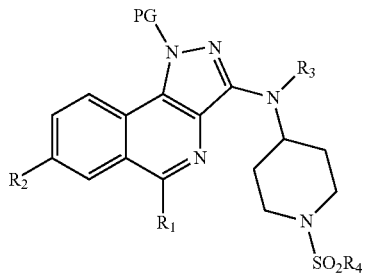

or of formula

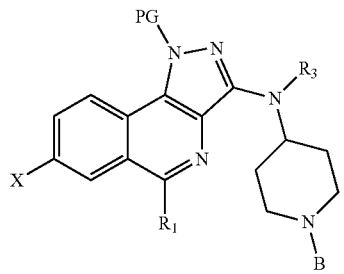

in which:
R₁ represents a phenyl group which is optionally substituted by one or more halogen atoms;
R₂ represents:
a hydrogen or halogen atom or a cyano group;
a group —C(=O)Y in which Y represents a hydrogen atom or a group —NH₂ or OR_a;
a group —C(=S)NH₂;
a group —C(=NH)NH—OH;
a group —CH₂OH or —CH₂F;
a group —CH=N—OH;
a group —CH=CH₂ or —C≡C—R_a;
a group

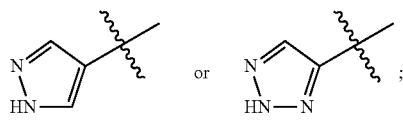

;

where $R_a$ represents a hydrogen atom or a $(C_1-C_4)$alkyl group;

$R_3$ represents a hydrogen atom or a $(C_1-C_4)$alkyl group;

$R_4$ represents an —$NH_2$, $(C_1-C_4)$alkyl, $(C_1-C_4)$fluoroalkyl or $(C_3-C_7)$cycloalkyl group;

X represents a hydrogen or fluorine atom, a group cyano; —C(=O)H; —CH=$CH_2$; —C≡C—$SiMe_3$; —C≡CH, —$COOR_a$, where $R_a$ represents a hydrogen atom or a $(C_1-C_4)$alkyl group, or the group

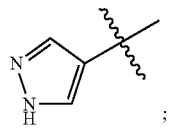

PG represents a protective group for the NH function of the pyrazole group;

B represents a hydrogen atom or a protective group PG' for the amine function.

12. The compound according to claim 11, in which PG represents SEM or $SO_2NMe_2$ and PG' represents BOC.

13. The compound according to claim 11, in which PG' represents BOC.

* * * * *

UNITED STATES PATENT AND TRADEMARK OFFICE
CERTIFICATE OF CORRECTION

PATENT NO. : 8,461,175 B2  Page 1 of 1
APPLICATION NO. : 13/265981
DATED : June 11, 2013
INVENTOR(S) : Delettre et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 53 days.

Signed and Sealed this
Eighth Day of September, 2015

Michelle K. Lee
*Director of the United States Patent and Trademark Office*